(12) United States Patent
Fujiwara et al.

(10) Patent No.: US 6,376,189 B1
(45) Date of Patent: *Apr. 23, 2002

(54) METHOD FOR DETECTING EXPRESSION OF HUMAN SKELETAL MUSCLE-SPECIFIC UNBIQUITIN-CONJUGATED ENZYME

(75) Inventors: Tsutomu Fujiwara; Takeshi Watanabe, both of Tokushima-ken (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/661,468

(22) Filed: Sep. 13, 2000

Related U.S. Application Data

(62) Division of application No. 09/273,565, filed on Mar. 22, 1999, now Pat. No. 6,166,190, which is a division of application No. 09/055,699, filed on Apr. 7, 1998, now Pat. No. 6,005,088, which is a division of application No. 08/820,170, filed on Mar. 19, 1997, now Pat. No. 5,831,058.

(30) Foreign Application Priority Data

Mar. 19, 1996 (JP) ............................................. 8-63410
Mar. 5, 1997 (JP) ............................................. 9-69163

(51) Int. Cl.⁷ .......................... C07H 21/04; C12Q 1/68
(52) U.S. Cl. ................. 435/6; 536/23.1; 536/23.2; 536/23.5; 536/24.3; 536/24.31; 536/24.33
(58) Field of Search ............................ 435/6; 536/23.1, 536/23.2, 23.5, 24.3, 24.31, 24.33

(56) References Cited

U.S. PATENT DOCUMENTS

| 5,863,779 A | 1/1999 | Lai ............................. 435/193 |
| 5,952,181 A | 9/1999 | Lai ................................. 435/6 |
| 6,166,190 A | * 12/2000 | Fujiwara et al. ............ 536/23.2 |

OTHER PUBLICATIONS

Clone GEN–501D08, *EMBO J.*, 12:339–347 (1993), Abstract.
Clone Gene–080G1, GeneBank Database Accession No. D49738.
Clone GEN–025F07, GeneBank Database Accession Nos. Z4991, L34070, U18530 and X59720.
Clone GEN–076C09, *Genomics*, 9(4):728–736 (1991), Abstract.
Clone GEN–331G07, *Nature*, 357(6380):700–702 (1992), Abstract.
Clone GEN–163D09, GeneBank Database Accession No. Z49154.
Clone GEN–078D05, *Biochem. J.*, 297(Pt2):389–397 (1994), Abstract.
Clone GEN–432A12, *Mol. Gen. Genet.*, 244(5):548–556 (1994), Abstract.
Clone GEN–092E10, GeneBank Database Accession No. U19878.
Clone GEN–428B12, *Mol. Cell Biol.*, 15(1):5645–565 (1995), Abstract.
Clone GEN–073E05, *Genomics*, 22(2):425–430 (1994), Abstract.
Clone GEN–093E05, *Dev. Dyn.*, 203(2):212–222 (1995), Abstract.
Clone GEN–077A09, *EMBO J.*, 8(12):3807–3814 (1989), Abstract.
*Hum. Genet.*, 86:14–16 (1990).
*Proc. Natl. Sci., USA*, 87:6634–6638 (1990).
*DNA Research*, 2:107–111 (1995).
*Human Genet.*, 88:119–121 (1991).
Peterson et al, *J. Biol. Chem.*, 271(47):29903–29908 (1996).

* cited by examiner

*Primary Examiner*—Sean McGarry
(74) *Attorney, Agent, or Firm*—Sughrue Mion, PLLC

(57) ABSTRACT

An isolated nucleic acid molecule encoding human skeletal muscle-specific ubiquitin-conjugating enzyme and comprising a nucleotide sequence coding for the amino acid sequence shown in SEQ ID NO:22 is disclosed. The isolation of this molecule makes it possible to detect its expression in various tissues, analyze its structure and function, and produce the human proteins encoded by this molecule by the technology of genetic engineering. In this way, it is possible to analyze the corresponding expression products, elucidate the pathology of diseases associated with the molecule, for example hereditary diseases and cancer, and diagnose and treat such diseases.

2 Claims, 2 Drawing Sheets

1  2

SEQUENCE LISTING

```
<160> NUMBER OF SEQ ID NOS:  95

<210> SEQ ID NO 1
<211> LENGTH: 122
<212> TYPE: PRT
<213> ORGANISM: Homo sapiens

<400> SEQUENCE: 1

Met Glu Leu Gly Glu Asp Gly Ser Val Tyr Lys Ser Ile Leu Val Thr
      1               5                   10                  15
      Ser Gln Asp Lys Ala Pro Ser Val Ile Ser Arg Val Leu Lys Lys Asn
                  20                  25                  30
      Asn Arg Asp Ser Ala Val Ala Ser Glu Tyr Glu Leu Val Gln Leu Leu
              35                  40                  45
      Pro Gly Glu Arg Glu Leu Thr Ile Pro Ala Ser Ala Asn Val Phe Tyr
          50                  55                  60
      Pro Met Asp Gly Ala Ser His Asp Phe Leu Leu Arg Gln Arg Arg
      65                  70                  75                  80
      Ser Ser Thr Ala Thr Pro Gly Val Thr Ser Gly Pro Ser Ala Ser Gly
                      85                  90                  95
      Thr Pro Pro Ser Glu Gly Gly Gly Ser Phe Pro Arg Ile Lys Ala
                  100                 105                 110
      Thr Gly Arg Lys Ile Ala Arg Ala Leu Phe
```

<210> SEQ ID NO 2
<211> LENGTH: 366
<212> TYPE: DNA
<213> ORGANISM: Homo sapiens

<400> SEQUENCE: 2

```
atggagttgg gggaagatgg cagtgtctat aagagcattt tggtgacaag ccaggacaag   60
gctccaagtg tcatcagtcg tgtccttaag aaaaacaatc gtgactctgc agtggcttca  120
gagtatgagc tggtacagct gctaccaggg gagcgagagc tgactatccc agcctcggct  180
aatgtattct accccatgga tggagcttca cacgatttcc tcctgcggca gcggcgaagg  240
tcctctactg ctacacctgg cgtcaccagt ggcccgtctg cctcaggaac tcctccgagt  300
gagggaggag ggggctcctt cccaggatc aaggccacag ggaggaagat tgcacgggca  360
ctgttc                                                              366
```

<210> SEQ ID NO 3
<211> LENGTH: 842
<212> TYPE: DNA
<213> ORGANISM: Homo sapiens
<220> FEATURE:
<221> NAME/KEY: CDS
<222> LOCATION: (28)..(393)

<400> SEQUENCE: 3

```
cccacgagcc gtatcatccg agtccag atg gag ttg ggg gaa gat ggc agt gtc    54
                             Met Glu Leu Gly Glu Asp Gly Ser Val
                               1               5
tat aag agc att ttg gtg aca agc cag gac aag gct cca agt gtc atc    102
Tyr Lys Ser Ile Leu Val Thr Ser Gln Asp Lys Ala Pro Ser Val Ile
 10                  15                  20                  25
agt cgt gtc ctt aag aaa aac aat cgt gac tct gca gtg gct tca gag   150
Ser Arg Val Leu Lys Lys Asn Asn Arg Asp Ser Ala Val Ala Ser Glu
                 30                  35                  40
tat gag ctg gta cag ctg cta cca ggg gag cga gag ctg act atc cca   198
Tyr Glu Leu Val Gln Leu Leu Pro Gly Glu Arg Glu Leu Thr Ile Pro
             45                  50                  55
gcc tcg gct aat gta ttc tac ccc atg gat gga gct tca cac gat ttc   246
Ala Ser Ala Asn Val Phe Tyr Pro Met Asp Gly Ala Ser His Asp Phe
         60                  65                  70
ctc ctg cgg cag cgg cga agg tcc tct act gct aca cct ggc gtc acc   294
Leu Leu Arg Gln Arg Arg Arg Ser Ser Thr Ala Thr Pro Gly Val Thr
     75                  80                  85
agt ggc ccg tct gcc tca gga act cct ccg agt gag gga gga ggg ggc   342
Ser Gly Pro Ser Ala Ser Gly Thr Pro Pro Ser Glu Gly Gly Gly Gly
 90                  95                 100                 105
tcc ttt ccc agg atc aag gcc aca ggg agg aag att gca cgg gca ctg   390
Ser Phe Pro Arg Ile Lys Ala Thr Gly Arg Lys Ile Ala Arg Ala Leu
                110                 115                 120
ttc tgaggaggaa gccccttttt ttacagaagt catggtgttc ataccagatg          443
Phe
tgggtagcca tcctgaatgg tggcaattat atcacattga acagaaatt cagaaaggga   503
gccagccacc ctggggcagt gaagtgccac tggtttacca gacagctgag aaatccagcc   563
ctgtcggaac tggtgtctta taaccaagtt ggatacctgt gtatagcttg ccaccttcca   623
tgagtgcagc acacaggtag tgctggaaaa acgcatcagt ttctgattct tggccatatc   683
ctaacatgca agggccaagc aaaggcttca aggctctgag ccccagggca gaggggaatg   743
gcaaaatgta ggtcctggca ggagctcttc ttcccactct gggggtttct atcactgtga   803
caacactaag ataataaacc aaaacactac ctgaattct                           842
```

<210> SEQ ID NO 4
<211> LENGTH: 193
<212> TYPE: PRT
<213> ORGANISM: Homo sapiens

<400> SEQUENCE: 4

```
Met Glu Leu Glu Leu Tyr Gly Val Asp Asp Lys Phe Tyr Ser Lys Leu
  1               5                  10                  15
Asp Gln Glu Asp Ala Leu Leu Gly Ser Tyr Pro Val Asp Asp Gly Cys
             20                  25                  30
Arg Ile His Val Ile Asp His Ser Gly Ala Arg Leu Gly Glu Tyr Glu
         35                  40                  45
Asp Val Ser Arg Val Glu Lys Tyr Thr Ile Ser Gln Glu Ala Tyr Asp
     50                  55                  60
```

```
       Gln Arg Gln Asp Thr Val Arg Ser Phe Leu Lys Arg Ser Lys Leu Gly
        65                  70                  75                  80
       Arg Tyr Asn Glu Glu Glu Arg Ala Gln Gln Glu Ala Glu Ala Ala Gln
                        85                  90                  95
       Arg Leu Ala Glu Glu Lys Ala Gln Ala Ser Ser Ile Pro Val Gly Ser
                   100                 105                 110
       Arg Cys Glu Val Arg Ala Ala Gly Gln Ser Pro Arg Arg Gly Thr Val
                   115                 120                 125
       Met Tyr Val Gly Leu Thr Asp Phe Lys Pro Gly Tyr Trp Ile Gly Val
               130                 135                 140
       Arg Tyr Asp Glu Pro Leu Gly Lys Asn Asp Gly Ser Val Asn Gly Lys
       145                 150                 155                 160
       Arg Tyr Phe Glu Cys Gln Ala Lys Tyr Gly Ala Phe Val Lys Pro Ala
                       165                 170                 175
       Val Val Thr Val Gly Asp Phe Pro Glu Glu Asp Tyr Gly Leu Asp Glu
                   180                 185                 190
       Ile
```

<210> SEQ ID NO 5
<211> LENGTH: 579
<212> TYPE: DNA
<213> ORGANISM: Homo sapiens

<400> SEQUENCE: 5

```
atggaactgg agctgtatgg agttgacgac aagttctaca gcaagctgga tcaagaggat    60
gcgctcctgg gctcctaccc tgtagatgac ggctgccgca tccacgtcat tgaccacagt   120
ggcgcccgcc ttggtgagta tgaggacgtg tcccgggtgg agaagtacac gatctcacaa   180
gaagcctacg accagaggca agacacggtc cgctcttttcc tgaagcgcag caagctcggc   240
cggtacaacg aggaggagcg ggctcagcag gaggccgagg ccgcccagcg cctggccgag   300
gagaaggccc aggccagctc catcccctg ggcagccgct gtgaggtgcg ggcggcgcgg   360
caatcccctc gccggggcac cgtcatgtat gtaggtctca cagatttcaa gcctggctac   420
tggattggtg tccgctatga tgagccactg gggaaaaatg atggcagtgt gaatgggaaa   480
cgctacttcg aatgccaggc caagtatggc gcctttgtca agccagcagt cgtgacggtg   540
ggggacttcc cggaggagga ctacgggttg acgagata                            579
```

<210> SEQ ID NO 6
<211> LENGTH: 1015
<212> TYPE: DNA
<213> ORGANISM: Homo sapiens
<220> FEATURE:
<221> NAME/KEY: CDS
<222> LOCATION: (274)..(852)

<400> SEQUENCE: 6

```
tgattggtca ggcacggagc aggaggcggg ctgatagccc agcagcagca gcggcggcgg    60
cggctgcgga gcgggtgtga ggcggctgga ccgcgctgca ggcatccgcg ggcgcggcaa   120
gatggaggtg acgggggtgt cggcaccacg tgaccgtttt catcagcag ctccctcagc   180
accttccgct ccgagaagcg atacagccgc agcctcacca tcgctgagtt caagtgtaaa   240
ctggagttgc tggtgggcag ccctgcttcc tgc atg gaa ctg gag ctg tat gga   294
                                    Met Glu Leu Glu Leu Tyr Gly
                                     1               5
gtt gac gac aag ttc tac agc aag ctg gat caa gag gat gcg ctc ctg     342
Val Asp Asp Lys Phe Tyr Ser Lys Leu Asp Gln Glu Asp Ala Leu Leu
            10                  15                  20
ggc tcc tac cct gta gat gac ggc tgc cgc atc cac gtc att gac cac     390
Gly Ser Tyr Pro Val Asp Asp Gly Cys Arg Ile His Val Ile Asp His
        25                  30                  35
agt ggc gcc cgc ctt ggt gag tat gag gac gtg tcc cgg gtg gag aag     438
Ser Gly Ala Arg Leu Gly Glu Tyr Glu Asp Val Ser Arg Val Glu Lys
 40                  45                  50                  55
tac acg atc tca caa gaa gcc tac gac cag agg caa gac acg gtc cgc     486
Tyr Thr Ile Ser Gln Glu Ala Tyr Asp Gln Arg Gln Asp Thr Val Arg
                60                  65                  70
tct ttc ctg aag cgc agc aag ctc ggc cgg tac aac gag gag gag cgg     534
Ser Phe Leu Lys Arg Ser Lys Leu Gly Arg Tyr Asn Glu Glu Glu Arg
            75                  80                  85
gct cag cag gag gcc gag gcc gcc cag cgc ctg gcc gag gag aag gcc     582
Ala Gln Gln Glu Ala Glu Ala Ala Gln Arg Leu Ala Glu Glu Lys Ala
        90                  95                 100
cag gcc agc tcc atc ccc gtg ggc agc cgc tgt gag gtg cgg gcg gcg     630
Gln Ala Ser Ser Ile Pro Val Gly Ser Arg Cys Glu Val Arg Ala Ala
    105                 110                 115
gga caa tcc cct cgc cgg ggc acc gtc atg tat gta ggt ctc aca gat     678
Gly Gln Ser Pro Arg Arg Gly Thr Val Met Tyr Val Gly Leu Thr Asp
120                 125                 130                 135
```

```
        ttc aag cct ggc tac tgg att ggt gtc cgc tat gat gag cca ctg ggg    726
        Phe Lys Pro Gly Tyr Trp Ile Gly Val Arg Tyr Asp Glu Pro Leu Gly
                        140                 145                 150
        aaa aat gat ggc agt gtg aat ggg aaa cgc tac ttc gaa tgc cag gcc    774
        Lys Asn Asp Gly Ser Val Asn Gly Lys Arg Tyr Phe Glu Cys Gln Ala
                    155                 160                 165
        aag tat ggc gcc ttt gtc aag cca gca gtc gtg acg gtg ggg gac ttc    822
        Lys Tyr Gly Ala Phe Val Lys Pro Ala Val Val Thr Val Gly Asp Phe
                170                 175                 180
        ccg gag gag gac tac ggg ttg gac gag ata tgacacctaa ggaattcccc      872
        Pro Glu Glu Asp Tyr Gly Leu Asp Glu Ile
            185                 190
        tgcttcagct cctagctcag ccactgactg cccctcctgt gtgtgcccat ggcccttttc   932
        tcctgacccc attttaattt tattcattttt ttcctttgcc attgattttt gagactcatg  992
        cattaaattc actagaaacc cag                                         1015

<210> SEQ ID NO 7
<211> LENGTH: 128
<212> TYPE: PRT
<213> ORGANISM: Homo sapiens

<400> SEQUENCE: 7

Met Thr Glu Ala Asp Val Asn Pro Lys Ala Tyr Pro Leu Ala Asp Ala
        1               5                   10                  15
        His Leu Thr Lys Lys Leu Leu Asp Leu Val Gln Gln Ser Cys Asn Tyr
                        20                  25                  30
        Lys Gln Leu Arg Lys Gly Ala Asn Glu Ala Thr Lys Thr Leu Asn Arg
                    35                  40                  45
        Gly Ile Ser Glu Phe Ile Val Met Ala Ala Asp Ala Glu Pro Leu Glu
                50                  55                  60
        Ile Ile Leu His Leu Pro Leu Leu Cys Glu Asp Lys Asn Val Pro Tyr
        65                  70                  75                  80
        Val Phe Val Arg Ser Lys Gln Ala Leu Gly Arg Ala Cys Gly Val Ser
                        85                  90                  95
        Arg Pro Val Ile Ala Cys Ser Val Thr Ile Lys Glu Gly Ser Gln Leu
                        100                 105                 110
        Lys Gln Gln Ile Gln Ser Ile Gln Gln Ser Ile Glu Arg Leu Leu Val
                    115                 120                 125

<210> SEQ ID NO 8
<211> LENGTH: 384
<212> TYPE: DNA
<213> ORGANISM: Homo sapiens

<400> SEQUENCE: 8
atgactgagg ctgatgtgaa tccaaaggcc tatccccttg ccgatgccca cctcaccaag    60
        aagctactgg acctcgttca gcagtcatgt aactataagc agcttcggaa aggagccaat    120
        gaggccacca aaaccctcaa caggggcatc tctgagttca tcgtgatggc tgcagacgcc    180
        gagccactgg agatcattct gcacctgccg ctgctgtgta agacaagaa tgtgcccaac    240
        gtgtttgtgc gctccaagca ggccctgggg agagcctgtg gggtctccag gcctgtcatc    300
        gcctgttctg tcaccatcaa agaaggctcg cagctgaaac agcagatcca atccattcag    360
        cagtccattg aaaggctctt agtc                                         384

<210> SEQ ID NO 9
<211> LENGTH: 1493
<212> TYPE: DNA
<213> ORGANISM: Homo sapiens
<220> FEATURE:
<221> NAME/KEY: CDS
<222> LOCATION: (95)..(478)

<400> SEQUENCE: 9
atccgtgtcc ttgcggtgct gggcagcaga ccgtccaaac cgacacgcgt ggtatcctcg    60
        cggtgtccgg caagagacta ccaagacaga cgct atg act gag gct gat gtg aat   115
                                           Met Thr Glu Ala Asp Val Asn
                                           1               5
        cca aag gcc tat ccc ctt gcc gat gcc cac ctc acc aag aag cta ctg    163
        Pro Lys Ala Tyr Pro Leu Ala Asp Ala His Leu Thr Lys Lys Leu Leu
                    10                  15                  20
        gac ctc gtt cag cag tca tgt aac tat aag cag ctt cgg aaa gga gcc    211
        Asp Leu Val Gln Gln Ser Cys Asn Tyr Lys Gln Leu Arg Lys Gly Ala
                25                  30                  35
        aat gag gcc acc aaa acc ctc aac agg ggc atc tct gag ttc atc gtg    259
        Asn Glu Ala Thr Lys Thr Leu Asn Arg Gly Ile Ser Glu Phe Ile Val
```

```
           Asn Glu Ala Thr Lys Thr Leu Asn Arg Gly Ile Ser Glu Phe Ile Val
           40                  45                  50                  55
atg gct gca gac gcc gag cca ctg gag atc att ctg cac ctg ccg ctg         307
Met Ala Ala Asp Ala Glu Pro Leu Glu Ile Ile Leu His Leu Pro Leu
                    60                  65                  70
ctg tgt gaa gac aag aat gtg ccc tac gtg ttt gtg cgc tcc aag cag         355
Leu Cys Glu Asp Lys Asn Val Pro Tyr Val Phe Val Arg Ser Lys Gln
                75                  80                  85
gcc ctg ggg aga gcc tgt ggg gtc tcc agg cct gtc atc gcc tgt tct         403
Ala Leu Gly Arg Ala Cys Gly Val Ser Arg Pro Val Ile Ala Cys Ser
            90                  95                  100
gtc acc atc aaa gaa ggc tcg cag ctg aaa cag cag atc caa tcc att         451
Val Thr Ile Lys Glu Gly Ser Gln Leu Lys Gln Gln Ile Gln Ser Ile
        105                 110                 115
cag cag tcc att gaa agg ctc tta gtc taaacctgtg gcctctgcca              498
Gln Gln Ser Ile Glu Arg Leu Leu Val
120                 125
cgtgctccct gccagcttcc cccctgaggt tgtgtatcat attatctgtg ttagcatgta       558
gtattttcag ctactctcta ttgttataaa atgtagtact aaatctggtt tctggatttt       618
tgtgttgttt ttgttctgtt ttacagggtt gctatccccc ttcctttcct ccctccctct       678
gccatcctte atccttttat cctcccttt tggaacaagt gttcagagca gacagaagca        738
gggtggtggc accgttgaaa ggcagaaaga gccaggagaa agctgatgga gccaggacag       798
agatctggtt ccagctttca gccactagct tcctgttgtg tgcggggtgt ggtggaatta      858
aacagcattc attgtgtgtc cctgtgcctg gcacacagaa tcattcatac gtgttcaagt       918
gatcaagggg tttcatttgc tcttggggga ttaggtatca tttggggagg aagcatgtgt      978
tctgtgaggt tgttcggcta tgtccaagtg tcgtttacta atgtaccct gctgtttgct       1038
tttggtaatg tgatgttgat gttctccccc tacccacaac catgcccttg agggtagcag       1098
ggcagcagca taccaaagag atgtgctgca ggactccgga gcagcctgga gtgggtgagc       1158
catggggcag ttgacctggg tcttgaaaga gtcggagtg acaagctcag agagcatgaa       1218
ctgatgctgg catgaaggat tccaggaaga tcatgagac ctggctggta gctgtaacag        1278
agatggtgga gtccaaggaa acagcctgtc tctggtgaat gggacttct ttggtggaca       1338
cttggcacca gctctgagag cccttccct gtgtcctgcc accatgtggg tcagatgtac       1398
tctctgtcac atgaggagag tgctagttca tgtgttctcc attcttgtga gcatcctaat      1458
aaatctgttc cattttgaaa aaaaaaaaa aaaaa                                   1493

<210> SEQ ID NO 10
<211> LENGTH: 711
<212> TYPE: PRT
<213> ORGANISM: Homo sapiens

<400> SEQUENCE: 10

Met Pro Ala Asp Val Asn Leu Ser Gln Lys Pro Gln Val Leu Gly Pro
        1               5                   10                  15
        Glu Lys Gln Asp Gly Ser Cys Glu Ala Ser Val Ser Phe Glu Asp Val
                        20                  25                  30
        Thr Val Asp Phe Ser Arg Glu Glu Trp Gln Gln Leu Asp Pro Ala Gln
                    35                  40                  45
        Arg Cys Leu Tyr Arg Asp Val Met Leu Glu Leu Tyr Ser His Leu Phe
             50                  55                  60
        Ala Val Gly Tyr His Ile Pro Asn Pro Glu Val Ile Phe Arg Met Leu
        65                  70                  75                  80
        Lys Glu Lys Glu Pro Arg Val Glu Glu Ala Glu Val Ser His Gln Arg
                        85                  90                  95
        Cys Gln Glu Arg Glu Phe Gly Leu Glu Ile Pro Gln Lys Glu Ile Ser
                    100                 105                 110
        Lys Lys Ala Ser Phe Gln Lys Asp Met Val Gly Glu Phe Thr Arg Asp
               115                  120                 125
        Gly Ser Trp Cys Ser Ile Leu Glu Glu Leu Arg Leu Asp Ala Asp Arg
        130                 135                 140
        Thr Lys Lys Asp Glu Gln Asn Gln Ile Gln Pro Met Ser His Ser Ala
        145                 150                 155                 160
        Phe Phe Asn Lys Lys Thr Leu Asn Thr Glu Ser Asn Cys Glu Tyr Lys
                        165                 170                 175
        Asp Pro Gly Lys Met Ile Arg Thr Arg Pro His Leu Ala Ser Ser Gln
                    180                 185                 190
        Lys Gln Pro Gln Lys Cys Cys Leu Phe Thr Glu Ser Leu Lys Leu Asn
                195                 200                 205
        Leu Glu Val Asn Gly Gln Asn Glu Ser Asn Asp Thr Glu Gln Leu Asp
            210                 215                 220
        Asp Val Val Gly Ser Gly Gln Leu Phe Ser His Ser Ser Asp Ala
        225                 230                 235                 240
        Cys Ser Lys Asn Ile His Thr Gly Glu Thr Phe Cys Lys Gly Asn Gln
                        245                 250                 255
        Cys Arg Lys Val Cys Gly His Lys Gln Ser Leu Lys Gln His Gln Ile
                    260                 265                 270
        His Thr Gln Lys Lys Pro Asp Gly Cys Ser Glu Cys Gly Gly Ser Phe
                275                 280                 285
```

-continued

```
        Thr Gln Lys Ser His Leu Phe Ala Gln Arg Ile His Ser Val Gly
            290                 295                 300
        Asn Leu His Glu Cys Gly Lys Cys Gly Lys Ala Phe Met Pro Gln Leu
        305                 310                 315                 320
        Lys Leu Ser Val Tyr Leu Thr Asp His Thr Gly Asp Ile Pro Cys Ile
                        325                 330                 335
        Cys Lys Glu Cys Gly Lys Val Phe Ile Gln Arg Ser Glu Leu Leu Thr
                    340                 345                 350
        His Gln Lys Thr His Thr Arg Lys Lys Pro Tyr Lys Cys His Asp Cys
                355                 360                 365
        Gly Lys Ala Phe Phe Gln Met Leu Ser Leu Phe Arg His Gln Arg Thr
            370                 375                 380
        His Ser Arg Glu Lys Leu Tyr Glu Cys Ser Glu Cys Gly Lys Gly Phe
        385                 390                 395                 400
        Ser Gln Asn Ser Thr Leu Ile Ile His Gln Lys Ile His Thr Gly Glu
                        405                 410                 415
        Arg Gln Tyr Ala Cys Ser Glu Cys Gly Lys Ala Phe Thr Gln Lys Ser
                    420                 425                 430
        Thr Leu Ser Leu His Gln Arg Ile His Ser Gly Gln Lys Ser Tyr Val
                435                 440                 445
        Cys Ile Glu Cys Gly Gln Ala Phe Ile Gln Lys Ala His Leu Ile Val
            450                 455                 460
        His Gln Arg Ser His Thr Gly Glu Lys Pro Tyr Gln Cys His Asn Cys
        465                 470                 475                 480
        Gly Lys Ser Phe Ile Ser Lys Ser Gln Leu Asp Ile His His Arg Ile
                        485                 490                 495
        His Thr Gly Glu Lys Pro Tyr Glu Cys Ser Asp Cys Gly Lys Thr Phe
                    500                 505                 510
        Thr Gln Lys Ser His Leu Asn Ile His Gln Lys Ile His Thr Gly Glu
                515                 520                 525
        Arg His His Val Cys Ser Glu Cys Gly Lys Ala Phe Asn Gln Lys Ser
            530                 535                 540
        Ile Leu Ser Met His Gln Arg Ile His Thr Gly Glu Lys Pro Tyr Lys
        545                 550                 555                 560
        Cys Ser Glu Cys Gly Lys Ala Phe Thr Ser Lys Ser Gln Phe Lys Glu
                        565                 570                 575
        His Gln Arg Ile His Thr Gly Glu Lys Pro Tyr Val Cys Thr Glu Cys
                    580                 585                 590
        Gly Lys Ala Phe Asn Gly Arg Ser Asn Phe His Lys His Gln Ile Thr
                595                 600                 605
        His Thr Arg Glu Arg Pro Phe Val Cys Tyr Lys Cys Gly Lys Ala Phe
            610                 615                 620
        Val Gln Lys Ser Glu Leu Ile Thr His Gln Arg Thr His Met Gly Glu
        625                 630                 635                 640
        Lys Pro Tyr Glu Cys Leu Asp Cys Gly Lys Ser Phe Ser Lys Lys Pro
                        645                 650                 655
        Gln Leu Lys Val His Gln Arg Ile His Thr Gly Glu Arg Pro Tyr Val
                    660                 665                 670
        Cys Ser Glu Cys Gly Lys Ala Phe Asn Asn Arg Ser Asn Phe Asn Lys
                675                 680                 685
        His Gln Thr Thr His Thr Arg Asp Lys Ser Tyr Lys Cys Ser Tyr Ser
            690                 695                 700
        Val Lys Gly Phe Thr Lys Gln
        705                 710

<210> SEQ ID NO 11
<211> LENGTH: 2133
<212> TYPE: DNA
<213> ORGANISM: Homo sapiens

<400> SEQUENCE: 11
atgcctgctg atgtgaattt atcccagaag cctcaggtcc tgggtccaga gaagcaggat   60
    ggatcttgcg aggcatcagt gtcatttgag gacgtgaccg tggacttcag cagggaggag  120
    tggcagcaac tggaccctgc ccagagatgc ctgtaccggg atgtgatgct ggagctctat  180
    agccatctct tcgcagtggg gtatcacatt cccaacccag aggtcatctt cagaatgcta  240
    aaagaaaagg agccgcgtgt ggaggaggct gaagtctcac atcagaggtc tcaagaaagg  300
    gagtttgggc ttgaaatccc acaaaaggag atttctaaga aagcttcatt tcaaaaggat  360
    atggtaggtg agttcacaag agatggttca tggtgttcca ttttagaaga actgaggctg  420
    gatgctgacc gcacaaagaa agatgagcaa aatcaaattc aacccatgag tcacagtgct  480
    ttcttcaaca agaaaacatt gaacacagaa agcaattgtg aatataagga ccctgggaaa  540
    atgattcgca cgaggcccca ccttgcttct tcacagaaac aacctcagaa atgttgctta  600
    tttacagaaa gtttgaagct gaacctagaa gtgaacggtc agaatgaaag caatgcacaca  660
    gaacagcctg atgacgttgt tgggtctggt cagctattca gccatagctc ttctgatgcc  720
    tgcagcaaga atattcatac aggagacaca ttttgcaaag gtaaccagtg tagaaaagtc  780
    tgtggccata acagtcactc aagcaacatc aaattcata ctcagaagaa accagatgga  840
    tgttctgaat gtgggggag cttcacccag aagtcacacc tctttgccca acagagaatt  900
    catagtgtag gaaaccctcca tgaatgtggc aaatgtggaa aagccttcat gccacaacta  960
```

-continued

```
aaactcagtg tatatctgac agatcataca ggtgatatac cctgtatatg caaggaatgt 1020
gggaaggtct ttattcagag atcagaattg cttacgcacc agaaaacaca cactagaaag 1080
aagccctata aatgccatga ctgtggaaaa gccttttcc agatgttatc tctcttcaga 1140
catcagagaa ctcacagtag agaaaaactc tatgaatgca gtgaatgtgg caaaggcttc 1200
tcccaaaact caaccctcat tatacatcag aaaattcata ctggtgagag acagtatgca 1260
tgcagtgaat gtgggaaagc ctttacccag aagtcaacac tcagcttgca ccagagaatc 1320
cactcagggc agaagtccta tgtgtgtatc gaatgcgggc aggccttcat ccagaaggca 1380
cacctgattg tccatcaaag aagccacaca ggagaaaaac cttatcagtg ccacaactgt 1440
gggaaatcct tcatttccaa gtcacagctt gatatacatc atcgaattca tacaggggag 1500
aaaccttatg aatgcagtga ctgtggaaaa accttcaccc aaagtcaca cctgaatata 1560
caccagaaaa ttcatactgg agaaagacac catgtatgca gtgaatgcgg gaaagccttc 1620
aaccagaagt caatactcag catgcatcag agaattcaca ccggagagaa gccttacaaa 1680
tgcagtgaat gtgggaaagc cttcacttct aagtctcaat tcaaagagca tcagcgaatt 1740
cacacgggtg agaaaccta tgtgtgcact gaatgtggga aggccttcaa cggcaggtca 1800
aatttccata aacatcaaat aactcacact agagaggcc ttttgtctg ttacaaatgt 1860
gggaaggctt ttgtccagaa atcagagttg attacccatc aaagaactca catgggagag 1920
aaaccctatg aatgccttga ctgtgggaaa tcgttcagta agaaaccaca actcaaggtg 1980
catcagcgaa ttcacacggg agaaagacct tatgtgtgtt ctgaatgtgg aaaggccttc 2040
aacaacaggt caaacttcaa taaacaccaa acaactcata ccagagacaa atcttacaaa 2100
tgcagttatt ctgtgaaagg ctttaccaag caa 2133
```

<210> SEQ ID NO 12
<211> LENGTH: 3754
<212> TYPE: DNA
<213> ORGANISM: Homo sapiens
<220> FEATURE:
<221> NAME/KEY: CDS
<222> LOCATION: (346)..(2478)

<400> SEQUENCE: 12

```
gctaagccta tgtcgcttac tggacgctga agtgattggg aatattagca gtggggttc   60
tgtagggtca ggaaggggcg gctggctttg gggagtgat gaggggcttg ttggggtgg   120
gggtgcgtga taagggatt tctcggctga agacgaggct gtgaggcttg tgcagaaccc  180
ccaggtcagg ccacatcatt gaggctgcag gatctctctc catagcccag tacgactctg  240
cgccgtgtcc ctggttggaa aatccaaaca cctatccagc ttctggctcc tgggaaaagt  300
ggagttgtca gcaagagaga ccgagagtag aagcccagag tggag atg cct gct gat  357
                                                    Met Pro Ala Asp
                                                      1 gtg aat tta tcc cag aag cct cag gtc ctg ggt cca gag aag cag gat   405
Val Asn Leu Ser Gln Lys Pro Gln Val Leu Gly Pro Glu Lys Gln Asp
  5                  10                  15                  20 gga tct tgc gag gca tca gtg tca ttt gag gac gtg acc gtg gac ttc   453
Gly Ser Cys Glu Ala Ser Val Ser Phe Glu Asp Val Thr Val Asp Phe
             25                  30                  35 agc agg gag gag tgg cag caa ctg gac cct gcc cag aga tgc ctg tac   501
Ser Arg Glu Glu Trp Gln Gln Leu Asp Pro Ala Gln Arg Cys Leu Tyr
         40                  45                  50 cgg gat gtg atg ctg gag ctc tat agc cat ctc ttc gca gtg ggg tat   549
Arg Asp Val Met Leu Glu Leu Tyr Ser His Leu Phe Ala Val Gly Tyr
     55                  60                  65 cac att ccc aac cca gag gtc atc ttc aga atg cta aaa gaa aag gag   597
His Ile Pro Asn Pro Glu Val Ile Phe Arg Met Leu Lys Glu Lys Glu
 70                  75                  80 ccg cgt gtg gag gag gct gaa gtc tca cat cag agg tgt caa gaa agg   645
Pro Arg Val Glu Glu Ala Glu Val Ser His Gln Arg Cys Gln Glu Arg
 85                  90                  95                 100 gag ttt ggg ctt gaa atc cca caa aag gag att tct aag aaa gct tca   693
Glu Phe Gly Leu Glu Ile Pro Gln Lys Glu Ile Ser Lys Lys Ala Ser
                 105                 110                 115 ttt caa aag gat atg gta ggt gag ttc aca aga gat ggt tca tgg tgt   741
Phe Gln Lys Asp Met Val Gly Glu Phe Thr Arg Asp Gly Ser Trp Cys
             120                 125                 130 tcc att tta gaa gaa ctg agg ctg gat gct gac cgc aca aag aaa gat   789
Ser Ile Leu Glu Glu Leu Arg Leu Asp Ala Asp Arg Thr Lys Lys Asp
         135                 140                 145 gag caa aat caa att caa ccc atg agt cac agt gct ttc ttc aac aag   837
Glu Gln Asn Gln Ile Gln Pro Met Ser His Ser Ala Phe Phe Asn Lys
     150                 155                 160 aaa aca ttg aac aca gaa agc aat tgt gaa tat aag gac cct ggg aaa   885
Lys Thr Leu Asn Thr Glu Ser Asn Cys Glu Tyr Lys Asp Pro Gly Lys
165                 170                 175                 180 atg att cgc acg agg ccc cac ctt gct tct tca cag aaa caa cct cag   933
Met Ile Arg Thr Arg Pro His Leu Ala Ser Ser Gln Lys Gln Pro Gln
                 185                 190                 195 aaa tgt tgc tta ttt aca gaa agt ttg aag ctg aac cta gaa gtg aac   981
Lys Cys Cys Leu Phe Thr Glu Ser Leu Lys Leu Asn Leu Glu Val Asn
             200                 205                 210
```

-continued

```
ggt cag aat gaa agc aat gac aca gaa cag ctt gat gac gtt gtt ggg    1029
Gly Gln Asn Glu Ser Asn Asp Thr Glu Gln Leu Asp Asp Val Val Gly
            215                 220                 225
tct ggt cag cta ttc agc cat agc tct tct gat gcc tgc agc aag aat    1077
Ser Gly Gln Leu Phe Ser His Ser Ser Ser Asp Ala Cys Ser Lys Asn
        230                 235                 240
att cat aca gga gag aca ttt tgc aaa ggt aac caa tgt aga aaa gtc    1125
Ile His Thr Gly Glu Thr Phe Cys Lys Gly Asn Gln Cys Arg Lys Val
245                 250                 255                 260
tgt ggc cat aaa cag tca ctc aag caa cat caa att cat act cag aag    1173
Cys Gly His Lys Gln Ser Leu Lys Gln His Gln Ile His Thr Gln Lys
                265                 270                 275
aaa cca gat gga tgt tct gaa tgt ggg ggg agc ttc acc cag aag tca    1221
Lys Pro Asp Gly Cys Ser Glu Cys Gly Gly Ser Phe Thr Gln Lys Ser
            280                 285                 290
cac ctc ttt gcc caa cag aga att cat agt gta gga aac ctc cat gaa    1269
His Leu Phe Ala Gln Gln Arg Ile His Ser Val Gly Asn Leu His Glu
        295                 300                 305
tgt ggc aaa tgt gga aaa gcc ttc atg cca caa cta aaa ctc agt gta    1317
Cys Gly Lys Cys Gly Lys Ala Phe Met Pro Gln Leu Lys Leu Ser Val
310                 315                 320
tat ctg aca gat cat aca ggt gat ata ccc tgt ata tgc aag gaa tgt    1365
Tyr Leu Thr Asp His Thr Gly Asp Ile Pro Cys Ile Cys Lys Glu Cys
325                 330                 335                 340
ggg aag gtc ttt att cag aga tca gaa ttg ctt acg cac cag aaa aca    1413
Gly Lys Val Phe Ile Gln Arg Ser Glu Leu Leu Thr His Gln Lys Thr
                345                 350                 355
cac act aga aag aag ccc tat aaa tgc cat gac tgt gga aaa gcc ttt    1461
His Thr Arg Lys Lys Pro Tyr Lys Cys His Asp Cys Gly Lys Ala Phe
            360                 365                 370
ttc cag atg tta tct ctc ttc aga cat cag aga act cac agt aga gaa    1509
Phe Gln Met Leu Ser Leu Phe Arg His Gln Arg Thr His Ser Arg Glu
        375                 380                 385
aaa ctc tat gaa tgc agt gaa tgt ggc aaa ggc ttc tcc caa aac tca    1557
Lys Leu Tyr Glu Cys Ser Glu Cys Gly Lys Gly Phe Ser Gln Asn Ser
390                 395                 400
acc ctc att ata cat cag aaa att cat act ggt gag aga cag tat gca    1605
Thr Leu Ile Ile His Gln Lys Ile His Thr Gly Glu Arg Gln Tyr Ala
405                 410                 415                 420
tgc agt gaa tgt ggg aaa gcc ttt acc cag aag tca aca ctc agc ttg    1653
Cys Ser Glu Cys Gly Lys Ala Phe Thr Gln Lys Ser Thr Leu Ser Leu
                425                 430                 435
cac cag aga atc cac tca ggg cag aag tcc tat gtg tgt atc gaa tgc    1701
His Gln Arg Ile His Ser Gly Gln Lys Ser Tyr Val Cys Ile Glu Cys
            440                 445                 450
ggg cag gcc ttc atc cag aag gca cac ctg att gtc cat caa aga agc    1749
Gly Gln Ala Phe Ile Gln Lys Ala His Leu Ile Val His Gln Arg Ser
        455                 460                 465
cac aca gga gaa aaa cct tat cag tgc cac aac tgt ggg aaa tcc ttc    1797
His Thr Gly Glu Lys Pro Tyr Gln Cys His Asn Cys Gly Lys Ser Phe
        470                 475                 480
att tcc aag tca cag ctt gat ata cat cat cga att cat aca ggg gag    1845
Ile Ser Lys Ser Gln Leu Asp Ile His His Arg Ile His Thr Gly Glu
485                 490                 495                 500
aaa cct tat gaa tgc agt gac tgt gga aaa acc ttc acc caa aag tca    1893
Lys Pro Tyr Glu Cys Ser Asp Cys Gly Lys Thr Phe Thr Gln Lys Ser
                505                 510                 515
cac ctg aat ata cac cag aaa att cat act gga gaa aga cac cat gta    1941
His Leu Asn Ile His Gln Lys Ile His Thr Gly Glu Arg His His Val
            520                 525                 530
tgc agt gaa tgc ggg aaa gcc ttc aac cag aag tca ata ctc agc atg    1989
Cys Ser Glu Cys Gly Lys Ala Phe Asn Gln Lys Ser Ile Leu Ser Met
        535                 540                 545
cat cag aga att cac acc gga gag aag cct tac aaa tgc agt gaa tgt    2037
His Gln Arg Ile His Thr Gly Glu Lys Pro Tyr Lys Cys Ser Glu Cys
550                 555                 560
ggg aaa gcc ttc act tct aag tct caa ttc aaa gag cat cag cga att    2085
Gly Lys Ala Phe Thr Ser Lys Ser Gln Phe Lys Glu His Gln Arg Ile
565                 570                 575                 580
cac acg ggt gag aaa ccc tat gtg tgc act gaa tgt ggg aag gcc ttc    2133
His Thr Gly Glu Lys Pro Tyr Val Cys Thr Glu Cys Gly Lys Ala Phe
                585                 590                 595
aac ggc agg tca aat ttc cat aaa cat caa ata act cac act aga gag    2181
Asn Gly Arg Ser Asn Phe His Lys His Gln Ile Thr His Thr Arg Glu
            600                 605                 610
agg cct ttt gtc tgt tac aaa tgt ggg aag gct ttc gtc cag aaa tca    2229
Arg Pro Phe Val Cys Tyr Lys Cys Gly Lys Ala Phe Val Gln Lys Ser
        615                 620                 625
gag ttg att acc cat caa aga act cac atg gga gag aaa ccc tat gaa    2277
```

```
        Glu Leu Ile Thr His Gln Arg Thr His Met Gly Glu Lys Pro Tyr Glu
                    630                 635                 640
        tgc ctt gac tgt ggg aaa tcg ttc agt aag aaa cca caa ctc aag gtg     2325
        Cys Leu Asp Cys Gly Lys Ser Phe Ser Lys Lys Pro Gln Leu Lys Val
        645                 650                 655                 660
        cat cag cga att cac acg gga gaa aga cct tat gtg tgt tct gaa tgt     2373
        His Gln Arg Ile His Thr Gly Glu Arg Pro Tyr Val Cys Ser Glu Cys
                            665                 670                 675
        gga aag gcc ttc aac aac agg tca aac ttc aat aaa cac caa aca act     2421
        Gly Lys Ala Phe Asn Asn Arg Ser Asn Phe Asn Lys His Gln Thr Thr
                        680                 685                 690
        cat acc aga gac aaa tct tac aaa tgc agt tat tct gtg aaa ggc ttt     2469
        His Thr Arg Asp Lys Ser Tyr Lys Cys Ser Tyr Ser Val Lys Gly Phe
                    695                 700                 705
        acc aag caa tgaattccta gtgcatcagc atattcataa atgaaatata             2518
        Thr Lys Gln
                710
        ctccgagttt cttgaagaag agaacatctt ctcagaatca ggtctaatta tatgttattg  2578
        aattcatgct tcagaaaaac tctagggatg cactgcatgt gtgaacacat gataaaaaag  2638
        tcatgcttta ttttagtgag ggcaattaca gagaaaagag taagcagaaa tgtccttctg  2698
        agtactggcc tcattaagga ttataaattt tctccccggg aagaaaccct gactaacgca  2758
        ttgagaaaag cctttctgta agaatggta caagacaggt tgttactcga ttatttatag   2818
        taaaatatgt gggaaattat atcaatgata accctgttta ttgtgggata tcaatatttt  2878
        taaagtgcca acacagtcat gataggacaa tattttaagt gtgtgtgtgc gccttatgta  2938
        tataagcata tatataatat ataagcatat tattatatac aggttgagta tcccttctcc  2998
        aaaatgcctg ggatcagaag catttttggat ttcagatact tacagatttt ggaatatttg 3058
        cattatattt attggttgag catccctaat ctgaaaatcc aagattaaat gctccaatta  3118
        gcatttcctt tgagcgtcat gttagagttc aaaaagtttc agattttcag ttttcagatt  3178
        aggaataccc aacctgtatg tacgtatatt tctgtatcta tgtatgtata tatatgcata  3238
        tgcagacata tgtatatggt ctggtcagca tatgtgtatg tatgcgtatg tatgtatgta  3298
        tgtatgccct cagtgcagtg gggtttgctg cagaattcac tgcatagcag gagatgtaag  3358
        cagatgagtt attttttaag agaatctaat ctaattgttt ttataaaaat tattccctat  3418
        tgaatattta tataatgagg ttgtatcaac aatgattaac tcctttatta tacatacaca  3478
        tgaatgtgca ttttttggtaa atgcataaat gagattctat aatgtttact gatctttata 3538
        ttacagattt tctcttcttt taggattagc tcagcttgcc cccccttttcc atctccacca 3598
        tctatagtga gcctctccat aattagtgcc aaccattagt ctcgttcata tttttacacc  3658
        aggagtcaac aaactgtgcc attggccaaa tatggcctcc caactgtttt tttaaaataa  3718
        agttttattg gaacacaaaa aaaaaaaaaa aaaaaa                              3754

<210> SEQ ID NO 13
<211> LENGTH: 389
<212> TYPE: PRT
<213> ORGANISM: Homo sapiens

<400> SEQUENCE: 13

Met Ala Asp Pro Arg Asp Lys Ala Leu Gln Asp Tyr Arg Lys Lys Leu
        1               5                   10                  15
        Leu Glu His Lys Glu Ile Asp Gly Arg Leu Lys Glu Leu Arg Glu Gln
                    20                  25                  30
        Leu Lys Glu Leu Thr Lys Gln Tyr Glu Lys Ser Glu Asn Asp Leu Lys
                35                  40                  45
        Ala Leu Gln Ser Val Gly Gln Ile Val Gly Glu Val Leu Lys Gln Leu
            50                  55                  60
        Thr Glu Glu Lys Phe Ile Val Lys Ala Thr Asn Gly Pro Arg Tyr Val
        65                  70                  75                  80
        Val Gly Cys Arg Arg Gln Leu Asp Lys Ser Lys Leu Lys Pro Gly Thr
                        85                  90                  95
        Arg Val Ala Leu Asp Met Thr Thr Leu Thr Ile Met Arg Tyr Leu Pro
                    100                 105                 110
        Arg Glu Val Asp Pro Leu Val Tyr Asn Met Ser His Glu Asp Pro Gly
                115                 120                 125
        Asn Val Ser Tyr Ser Glu Ile Gly Gly Leu Ser Glu Gln Ile Arg Glu
            130                 135                 140
        Leu Arg Glu Val Ile Glu Leu Pro Leu Thr Asn Pro Glu Leu Phe Gln
        145                 150                 155                 160
        Arg Val Gly Ile Ile Pro Pro Lys Gly Cys Leu Leu Tyr Gly Pro Pro
                        165                 170                 175
        Gly Thr Gly Lys Thr Leu Leu Ala Arg Ala Val Ala Ser Gln Leu Asp
                    180                 185                 190
        Cys Asn Phe Leu Lys Val Val Ser Ser Ser Ile Val Asp Lys Tyr Ile
                195                 200                 205
        Gly Glu Ser Ala Arg Leu Ile Arg Glu Met Phe Asn Tyr Ala Arg Asp
            210                 215                 220
        His Gln Pro Cys Ile Ile Phe Met Asp Glu Ile Asp Ala Ile Gly Gly
        225                 230                 235                 240
        Arg Arg Phe Ser Glu Gly Thr Ser Ala Asp Arg Glu Ile Gln Arg Thr
                        245                 250                 255
```

```
      Leu Met Glu Leu Leu Asn Gln Met Asp Gly Phe Asp Thr Leu His Arg
                      260                 265                 270
      Val Lys Met Thr Met Ala Thr Asn Arg Pro Asp Thr Leu Asp Pro Ala
                  275                 280                 285
      Leu Leu Arg Pro Gly Arg Leu Asp Arg Lys Ile His Ile Asp Leu Pro
              290                 295                 300
      Asn Glu Gln Ala Arg Leu Asp Ile Leu Lys Ile His Ala Gly Pro Ile
      305                 310                 315                 320
      Thr Lys His Gly Glu Ile Asp Tyr Glu Ala Ile Val Lys Leu Ser Asp
                      325                 330                 335
      Gly Phe Asn Gly Ala Asp Leu Arg Asn Val Cys Thr Glu Ala Gly Met
                  340                 345                 350
      Phe Ala Ile Arg Ala Asp His Asp Phe Val Val Gln Glu Asp Phe Met
              355                 360                 365
      Lys Ala Val Arg Lys Val Ala Asp Ser Lys Lys Leu Glu Ser Lys Leu
      370                 375                 380
      Asp Tyr Lys Pro Val
      385

<210> SEQ ID NO 14
<211> LENGTH: 1167
<212> TYPE: DNA
<213> ORGANISM: Homo sapiens

<400> SEQUENCE: 14
atggcggacc ctagagataa ggcgcttcag gactaccgca agaagttgct tgaacacaag    60
      gagatcgacg gccgtcttaa ggagttaagg gaacaattaa aagaacttac caagcagtat   120
      gaaaagtctg aaaatgatct gaaggcccta cagagtgttg ggcagatcgt gggtgaagtg   180
      cttaaacagt taactgaaga aaaattcatt gttaaagcta ccaatggacc aagatatgtt   240
      gtgggttgtc gtcgacagct tgacaaaagt aagctgaagc caggaacaag agttgcttg    300
      gatatgacta cactaactat catgagatat ttgccgagag aggtggatcc actggtttat   360
      aacatgtctc atgaggaccc tgggaatgtt tcttattctg agattggagg gctatcagaa   420
      cagatccggg aattaagaga ggtgataaga ttacctctta caaacccaga gttatttcag   480
      cgtgtaggaa taatacctcc aaaaggctgt ttgttatatg gaccaccagg tacgggaaaa   540
      acactcttgg cacgagccgt tgctagccag ctggactgca atttcttaaa ggttgtatct   600
      agttctattg tagacaagta cattggtgaa agtgctcgtt tgatcagaga aatgtttaat   660
      tatgctagag atcatcaacc atgcatcatt tttatggatg aaatagatgc tattggtggt   720
      cgtcggtttt ctgagggtac ttcagctgac agagagattc agagaacgtt aatggagtta   780
      ctgaatcaaa tggatggatt tgatactctg catagagtta aaatgaccat ggctacaaac   840
      agaccagata cactggatcc tgctttgctg cgtccaggaa gattagatag aaaaatacat   900
      attgatttgc caaatgaaca agcaagatta gacatactga aaatccatgc aggtcccatt   960
      acaaagcatg gtgaaataga ttatgaagca attgtgaagc tttcggatgg ctttaatgga  1020
      gcagatctga gaaatgtttg tactgaagca ggtatgttcg caattcgtgc tgatcatgat  1080
      tttgtagtac aggaagactt catgaaagca gtcagaaaag tggctgattc taagaagctg  1140
      gagtctaaat tggactacaa acctgtg                                      1167

<210> SEQ ID NO 15
<211> LENGTH: 1566
<212> TYPE: DNA
<213> ORGANISM: Homo sapiens
<220> FEATURE:
<221> NAME/KEY: CDS
<222> LOCATION: (17)..(1183)

<400> SEQUENCE: 15
gagacggctt ctcatc atg gcg gac cct aga gat aag gcg ctt cag gac tac    52
                       Met Ala Asp Pro Arg Asp Lys Ala Leu Gln Asp Tyr
                        1               5                  10
      cgc aag aag ttg ctt gaa cac aag gag atc gac ggc cgt ctt aag gag     100
      Arg Lys Lys Leu Leu Glu His Lys Glu Ile Asp Gly Arg Leu Lys Glu
                  15                  20                  25
      tta agg gaa caa tta aaa gaa ctt acc aag cag tat gaa aag tct gaa     148
      Leu Arg Glu Gln Leu Lys Glu Leu Thr Lys Gln Tyr Glu Lys Ser Glu
              30                  35                  40
      aat gat ctg aag gcc cta cag agt gtt ggg cag atc gtg ggt gaa gtg     196
      Asn Asp Leu Lys Ala Leu Gln Ser Val Gly Gln Ile Val Gly Glu Val
      45                  50                  55                  60
      ctt aaa cag tta act gaa gaa aaa ttc att gtt aaa gct acc aat gga     244
      Leu Lys Gln Leu Thr Glu Glu Lys Phe Ile Val Lys Ala Thr Asn Gly
                      65                  70                  75
      cca aga tat gtt gtg ggt tgt cgt cga cag ctt gac aaa agt aag ctg     292
      Pro Arg Tyr Val Val Gly Cys Arg Arg Gln Leu Asp Lys Ser Lys Leu
                  80                  85                  90
      aag cca gga aca aga gtt gct ttg gat atg act aca cta act atc atg     340
      Lys Pro Gly Thr Arg Val Ala Leu Asp Met Thr Thr Leu Thr Ile Met
```

```
                        95                      100                     105
        aga tat ttg ccg aga gag gtg gat cca ctg gtt tat aac atg tct cat    388
        Arg Tyr Leu Pro Arg Glu Val Asp Pro Leu Val Tyr Asn Met Ser His
                110                     115                     120
        gag gac cct ggg aat gtt tct tat tct gag att gga ggg cta tca gaa    436
        Glu Asp Pro Gly Asn Val Ser Tyr Ser Glu Ile Gly Gly Leu Ser Glu
        125                     130                     135                 140
        cag atc cgg gaa tta aga gag gtg ata gaa tta cct ctt aca aac cca    484
        Gln Ile Arg Glu Leu Arg Glu Val Ile Glu Leu Pro Leu Thr Asn Pro
                    145                     150                     155
        gag tta ttt cag cgt gta gga ata ata cct aaa ggc tgt ttg tta        532
        Glu Leu Phe Gln Arg Val Gly Ile Ile Pro Pro Lys Gly Cys Leu Leu
                160                     165                     170
        tat gga cca cca ggt acg gga aaa aca ctc ttg gca cga gcc gtt gct    580
        Tyr Gly Pro Pro Gly Thr Gly Lys Thr Leu Leu Ala Arg Ala Val Ala
                175                     180                     185
        agc cag ctg gac tgc aat ttc tta aag gtt gta tct agt tct att gta    628
        Ser Gln Leu Asp Cys Asn Phe Leu Lys Val Val Ser Ser Ser Ile Val
        190                     195                     200
        gac aag tac att ggt gaa agt gct cgt ttg atc aga gaa atg ttt aat    676
        Asp Lys Tyr Ile Gly Glu Ser Ala Arg Leu Ile Arg Glu Met Phe Asn
        205                     210                     215                 220
        tat gct aga gat cat caa cca tgc atc att ttt atg gat gaa ata gat    724
        Tyr Ala Arg Asp His Gln Pro Cys Ile Ile Phe Met Asp Glu Ile Asp
                    225                     230                     235
        gct att ggt ggt cgt cgg ttt tct gag ggt act tca gct gac aga gag    772
        Ala Ile Gly Gly Arg Arg Phe Ser Glu Gly Thr Ser Ala Asp Arg Glu
                240                     245                     250
        att cag aga acg tta atg gag tta ctg aat caa atg gat gga ttt gat    820
        Ile Gln Arg Thr Leu Met Glu Leu Leu Asn Gln Met Asp Gly Phe Asp
        255                     260                     265
        act ctg cat aga gtt aaa atg acc atg gct aca aac aga cca gat aca    868
        Thr Leu His Arg Val Lys Met Thr Met Ala Thr Asn Arg Pro Asp Thr
            270                     275                     280
        ctg gat cct gct ttg ctg cgt cca gga aga tta gat aga aaa ata cat    916
        Leu Asp Pro Ala Leu Leu Arg Pro Gly Arg Leu Asp Arg Lys Ile His
        285                     290                     295                 300
        att gat ttg cca aat gaa caa gca aga tta gac ata ctg aaa atc cat    964
        Ile Asp Leu Pro Asn Glu Gln Ala Arg Leu Asp Ile Leu Lys Ile His
                    305                     310                     315
        gca ggt ccc att aca aag cat ggt gaa ata gat tat gaa gca att gtg   1012
        Ala Gly Pro Ile Thr Lys His Gly Glu Ile Asp Tyr Glu Ala Ile Val
                320                     325                     330
        aag ctt tcg gat ggc ttt aat gga gca gat ctg aga aat gtt tgt act   1060
        Lys Leu Ser Asp Gly Phe Asn Gly Ala Asp Leu Arg Asn Val Cys Thr
                335                     340                     345
        gaa gca ggt atg ttc gca att cgt gct gat cat gat ttt gta gta cag   1108
        Glu Ala Gly Met Phe Ala Ile Arg Ala Asp His Asp Phe Val Val Gln
        350                     355                     360
        gaa gac ttc atg aaa gca gtc aga aaa gtg gct gat tct aag aag ctg   1156
        Glu Asp Phe Met Lys Ala Val Arg Lys Val Ala Asp Ser Lys Lys Leu
        365                     370                     375                 380
        gag tct aaa ttg gac tac aaa cct gtg taatttactg taagatttttt         1203
        Glu Ser Lys Leu Asp Tyr Lys Pro Val
                    385
        gatggctgca tgacagatgt tggcttattg taaaaataaa gttaaagaaa ataatgtatg  1263
        tattggcaat gatgtcatta aaagtatatg aataaaaata tgagtaacat cataaaaatt  1323
        agtaattcaa cttttaagat acagaagaaa tttgtatgtt tgttaaagtt gcatttattg  1383
        cagcaagtta caaagggaaa gtgttgaagc ttttcatatt tgctgcgtga gcattttgta  1443
        aaatattgaa agtggtttga gatagtggta taagaaagca tttcttatga cttattttgt  1503
        atcatttgtt ttcctcatct aaaaagttga ataaaatctg tttgattcag ttctcctaaa  1563
        aaa                                                               1566
```

<210> SEQ ID NO 16
<211> LENGTH: 223
<212> TYPE: PRT
<213> ORGANISM: Homo sapiens

<400> SEQUENCE: 16

```
        Met Ser Asp Glu Glu Ala Arg Gln Ser Gly Gly Ser Ser Gln Ala Gly
        1               5                   10                  15
        Val Val Thr Val Ser Asp Val Gln Leu Met Arg Arg Lys Glu Glu
                    20                  25                  30
        Ile Glu Ala Gln Ile Lys Ala Asn Tyr Asp Val Leu Glu Ser Gln Lys
                35                  40                  45
        Gly Ile Gly Met Asn Glu Pro Leu Val Asp Cys Glu Gly Tyr Pro Arg
            50                  55                  60
```

```
            Ser Asp Val Asp Leu Tyr Gln Val Arg Thr Ala Arg His Asn Ile Ile
            65                  70                  75                  80
            Cys Leu Gln Asn Asp His Lys Ala Val Met Lys Gln Val Glu Glu Ala
                            85                  90                  95
            Leu His Gln Leu His Ala Arg Asp Lys Glu Lys Gln Ala Arg Asp Met
                        100                 105                 110
            Ala Glu Ala His Lys Glu Ala Met Ser Arg Lys Leu Gly Gln Ser Glu
                    115                 120                 125
            Ser Gln Gly Pro Pro Arg Ala Phe Ala Lys Val Asn Ser Ile Ser Pro
                130                 135                 140
            Gly Ser Pro Ala Ser Ile Ala Gly Leu Gln Val Asp Glu Ile Val
            145                 150                 155                 160
            Glu Phe Gly Ser Val Asn Thr Gln Asn Phe Gln Ser Leu His Asn Ile
                            165                 170                 175
            Gly Ser Val Val Gln His Ser Glu Gly Lys Pro Leu Asn Val Thr Val
                        180                 185                 190
            Ile Arg Arg Gly Glu Lys His Gln Leu Arg Leu Val Pro Thr Arg Trp
                    195                 200                 205
            Ala Gly Lys Gly Leu Leu Gly Cys Asn Ile Ile Pro Leu Gln Arg
                210                 215                 220

<210> SEQ ID NO 17
<211> LENGTH: 669
<212> TYPE: DNA
<213> ORGANISM: Homo sapiens

<400> SEQUENCE: 17
atgtccgacg aggaagcgag gcagagcgga ggctcctcgc aggccggcgt cgtgactgtc    60
     agcgacgtcc aggagctgat gcggcgcaag gaggagatag aagcgcagat caaggccaac   120
     tatgacgtgc tggaaagcca aaaaggcatt gggatgaacg agccgctggt ggactgtgag   180
     ggctaccccc ggtcagacgt ggacctgtac caagtccgca ccgccaggca caacatcata   240
     tgcctgcaga atgatcacaa ggcagtgatg aagcaggtgg aggaggccct gcaccagctg   300
     cacgctcgcg acaaggagaa gcaggcccgg gacatggctg aggcccacaa gagggccatg   360
     agccgcaaac tgggtcagag tgagagccaa ggccctccac gggccttcgc caaagtgaac   420
     agcatcagcc ccggctcccc agccagcatc gcgggtctgc aagtggatga tgagattgtg   480
     gagttcggct ctgtgaacac ccagaacttc cagtcactgc ataacattgg cagtgtggtg   540
     cagcacagtg aggggaagcc cctgaatgtg acagtgatcc gcagggggga aaaacaccag   600
     cttagacttg ttccaacacg ctgggcagga aaaggactgc tgggctgcaa cattattcct   660
     ctgcaaaga                                                           669

<210> SEQ ID NO 18
<211> LENGTH: 1128
<212> TYPE: DNA
<213> ORGANISM: Homo sapiens
<220> FEATURE:
<221> NAME/KEY: CDS
<222> LOCATION: (125)..(793)

<400> SEQUENCE: 18
actgttctcg cgttcgcgga cggctgtggt gttttggcgc atgggcggag cgtagttacg    60
     gtcgactggg gcgtcgtccc tagcccggga gccgggtctc tggagtcgcg gcccggggtt   120
     cacg atg tcc gac gag gaa gcg agg cag agc gga ggc tcc tcg cag gcc   169
          Met Ser Asp Glu Glu Ala Arg Gln Ser Gly Gly Ser Ser Gln Ala
          1               5                   10                  15
     ggc gtc gtg act gtc agc gac gtc cag gag ctg atg cgg cgc aag gag   217
     Gly Val Val Thr Val Ser Asp Val Gln Glu Leu Met Arg Arg Lys Glu
                     20                  25                  30
     gag ata gaa gcg cag atc aag gcc aac tat gac gtg ctg gaa agc caa   265
     Glu Ile Glu Ala Gln Ile Lys Ala Asn Tyr Asp Val Leu Glu Ser Gln
                 35                  40                  45
     aaa ggc att ggg atg aac gag ccg ctg gtg gac tgt gag ggc tac ccc   313
     Lys Gly Ile Gly Met Asn Glu Pro Leu Val Asp Cys Glu Gly Tyr Pro
             50                  55                  60
     cgg tca gac gtg gac ctg tac caa gtc cgc acc gcc agg cac aac atc   361
     Arg Ser Asp Val Asp Leu Tyr Gln Val Arg Thr Ala Arg His Asn Ile
     65                  70                  75
     ata tgc ctg cag aat gat cac aag gca gtg atg aag cag gtg gag gag   409
     Ile Cys Leu Gln Asn Asp His Lys Ala Val Met Lys Gln Val Glu Glu
         80                  85                  90                  95
     gcc ctg cac cag ctg cac gct cgc gac aag gag aag cag gcc cgg gac   457
     Ala Leu His Gln Leu His Ala Arg Asp Lys Glu Lys Gln Ala Arg Asp
                     100                 105                 110
     atg gct gag gcc cac aaa gag gcc atg agc cgc aaa ctg ggt cag agt   505
     Met Ala Glu Ala His Lys Glu Ala Met Ser Arg Lys Leu Gly Gln Ser
                 115                 120                 125
```

-continued

```
gag agc cag ggc cct cca cgg gcc ttc gcc aaa gtg aac agc atc agc    553
Glu Ser Gln Gly Pro Pro Arg Ala Phe Ala Lys Val Asn Ser Ile Ser
            130                 135                 140
ccc ggc tcc cca gcc agc atc gcg ggt ctg caa gtg gat gat gag att    601
Pro Gly Ser Pro Ala Ser Ile Ala Gly Leu Gln Val Asp Asp Glu Ile
145                 150                 155
gtg gag ttc ggc tct gtg aac acc cag aac ttc cag tca ctg cat aac    649
Val Glu Phe Gly Ser Val Asn Thr Gln Asn Phe Gln Ser Leu His Asn
    160                 165                 170                 175
att ggc agt gtg gtg cag cac agt gag ggg aag ccc ctg aat gtg aca    697
Ile Gly Ser Val Val Gln His Ser Glu Gly Lys Pro Leu Asn Val Thr
                180                 185                 190
gtg atc cgc agg ggg gaa aaa cac cag ctt aga ctt gtt cca aca cgc    745
Val Ile Arg Arg Gly Glu Lys His Gln Leu Arg Leu Val Pro Thr Arg
            195                 200                 205
tgg gca gga aaa gga ctg ctg ggc tgc aac att att cct ctg caa aga    793
Trp Ala Gly Lys Gly Leu Leu Gly Cys Asn Ile Ile Pro Leu Gln Arg
        210                 215                 220
tgattgtccc tgggaacag taacaggaaa gcatcttccc ttgccctgga cttgggtcta    853
gggatttcca acttgtcttc tctccctgaa gcataaggat ctggaagagg cttgtaacct    913
gaacttctgt gtggtggcag tactgtggcc caccagtgta atctccctgg attaaggcat    973
tcttaaaaac ttaggcttgg cctctttcac aaattaggcc acggccctaa ataggaattc   1033
cctggattgt gggcaagtgg gcggaagtta ttctggcagg tactggtgtg attattatta   1093
ttatttttaa taaagagttt tacagtgctg atatg                              1128
```

<210> SEQ ID NO 19
<211> LENGTH: 506
<212> TYPE: PRT
<213> ORGANISM: Homo sapiens

<400> SEQUENCE: 19

```
Met Ala Glu Ala Asp Phe Lys Met Val Ser Glu Pro Val Ala His Gly
1               5                   10                  15
Val Ala Glu Glu Met Ala Ser Ser Thr Ser Asp Ser Gly Glu Glu
            20                  25                  30
Ser Asp Ser Ser Ser Ser Ser Ser Thr Ser Asp Ser Ser Ser
        35                  40                  45
Ser Ser Thr Ser Gly Ser Ser Gly Ser Gly Ser Ser Ser Ser
    50                  55                  60
Ser Gly Ser Thr Ser Ser Arg Ser Arg Leu Tyr Arg Lys Lys Arg Val
65                  70                  75                  80
Pro Glu Pro Ser Arg Arg Ala Arg Arg Ala Pro Leu Gly Thr Asn Phe
                85                  90                  95
Val Asp Arg Leu Pro Gln Ala Val Arg Asn Arg Val Gln Ala Leu Arg
            100                 105                 110
Asn Ile Gln Asp Glu Cys Asp Lys Val Asp Thr Leu Phe Leu Lys Ala
        115                 120                 125
Ile His Asp Leu Glu Arg Lys Tyr Ala Glu Leu Asn Lys Pro Leu Tyr
    130                 135                 140
Asp Arg Arg Phe Gln Ile Ile Asn Ala Glu Tyr Glu Pro Thr Glu Glu
145                 150                 155                 160
Glu Cys Glu Trp Asn Ser Glu Asp Glu Phe Ser Ser Asp Glu
                165                 170                 175
Val Gln Asp Asn Thr Pro Ser Glu Met Pro Pro Leu Glu Gly Glu Glu
            180                 185                 190
Glu Glu Asn Pro Lys Glu Asn Pro Glu Val Lys Ala Glu Glu Lys Glu
        195                 200                 205
Val Pro Lys Glu Ile Pro Glu Val Lys Asp Glu Glu Lys Glu Val Ala
    210                 215                 220
Lys Glu Ile Pro Glu Val Lys Ala Glu Lys Ala Asp Ser Lys Asp
225                 230                 235                 240
Cys Met Glu Ala Thr Pro Glu Val Lys Glu Asp Pro Lys Glu Val Pro
                245                 250                 255
Gln Val Lys Ala Asp Asp Lys Glu Gln Pro Lys Ala Thr Glu Ala Lys
            260                 265                 270
Ala Arg Ala Ala Val Arg Glu Thr His Lys Arg Val Pro Glu Glu Arg
        275                 280                 285
Leu Arg Asp Ser Val Asp Leu Lys Arg Ala Arg Lys Gly Lys Pro Lys
    290                 295                 300
Arg Glu Asp Pro Lys Gly Ile Pro Asp Tyr Trp Leu Ile Val Leu Lys
305                 310                 315                 320
Asn Val Asp Lys Leu Gly Pro Met Ile Gln Lys Tyr Asp Glu Pro Ile
                325                 330                 335
Leu Lys Phe Leu Ser Asp Val Ser Leu Lys Phe Ser Lys Pro Gly Gln
            340                 345                 350
Pro Val Ser Tyr Thr Phe Glu Phe His Phe Leu Pro Asn Pro Tyr Phe
        355                 360                 365
```

-continued

```
        Arg Asn Glu Val Leu Val Lys Thr Tyr Ile Ile Lys Ala Lys Pro Asp
            370                 375                 380
        His Asn Asp Pro Phe Phe Ser Trp Gly Trp Glu Ile Glu Asp Cys Lys
        385                 390                 395                 400
        Gly Cys Lys Ile Asp Arg Arg Gly Lys Asp Val Thr Val Thr Thr
                        405                 410                 415
        Thr Gln Ser Arg Thr Ala Thr Gly Glu Ile Glu Ile Gln Pro Arg
                    420                 425                 430
        Val Val Pro Asn Ala Ser Phe Phe Asn Phe Phe Ser Pro Pro Glu Ile
                435                 440                 445
        Pro Met Ile Gly Lys Leu Glu Pro Arg Glu Asp Ala Ile Leu Asp Glu
            450                 455                 460
        Asp Phe Glu Ile Gly Gln Ile Leu His Asp Asn Val Ile Leu Lys Ser
        465                 470                 475                 480
        Ile Tyr Tyr Tyr Thr Gly Glu Val Asn Gly Thr Tyr Tyr Gln Phe Gly
                        485                 490                 495
        Lys His Tyr Gly Asn Lys Lys Tyr Arg Lys
                    500                 505
```

<210> SEQ ID NO 20
<211> LENGTH: 1518
<212> TYPE: DNA
<213> ORGANISM: Homo sapiens

<400> SEQUENCE: 20

```
    atggcagaag cagattttaa aatggtctcg gaacctgtcg cccatggggt tgccgaagag    60
    gagatggcta gctcgactag tgattctggg gaagaatctg acagcagtag ctctagcagc   120
    agcactagtg acagcagcag cagcagcagc actagtggca gcagcagcgg cagcggcagc   180
    agcagcagca gcagcggcag cactagcagc cgcagccgct tgtatagaaa aagagggta    240
    cctgagcctt ccagaagggc gcggcgggcc ccgttgggaa caatttcgt ggataggctg    300
    cctcaggcag ttagaaatcg tgtgcaagcg cttagaaaca ttcaagatga atgtgacaag   360
    gtagataccc tgttcttaaa agcaattcat gatcttgaaa gaaaatatgc tgaactcaac   420
    aagcctctgt atgataggcg gtttcaaatc atcaatgcag aatacgagct tacagaagaa   480
    gaatgtgaat ggaattcaga ggatgaggag ttcagcagtg atgaggaggt gcagataac   540
    accctagtg aaatgcctcc cttagagggt gaggaagaag aaacccctaa agaaacccca   600
    gaggtgaaag ctgaagagaa ggaagttcct aaagaaattc ctgaggtgaa ggatgaagaa   660
    aaggaagttg ctaaagaaat tcctgaggta aaggctgaag aaaaagcaga ttctaaagac   720
    tgtatgggag caaccctga agtaaagaa gatcctaaga agtccccca ggtaaaggca   780
    gatgataaag aacagctaa agcaacagag gctaaggcaa gggctgcagt aagagagact   840
    cataaaagag ttcctgagga aaggcttcgg gacagtgtag atcttaaaag agctaggaag   900
    ggaaagccta aagagaaga cccctaaggc attcctgact attggctgat tgttttaaag   960
    aatgttgaca agctcgggcc tatgattcag aagtatgatg agcccattct gaagtttctg  1020
    tcggatgtta gcctgaagtt ctcaaaaacct ggccagcctg taagttacac cttttgaattt  1080
    cattttctac caacccata cttcagaaat gaggtgctgg tgaagacata tataataaag  1140
    gcaaaaccag atcacaatga tccctctttt tcttgggat gggaaattga agattgcaaa  1200
    ggctgcaaga tagaccggag aagaggaaaa gatgttactg tgacaactac ccagagtcgc  1260
    acaactgcta ctggagaaat tgaaatccag ccaagagtga ttcctaatgc atcattcttc  1320
    aacttcttta gtcctcctga gattcctatg attgggaagc tggaaccacg agaagatgct  1380
    atcctggatg aggactttga aattgggcag attttacatg ataatgtcat cctgaaatca  1440
    atctattact atactggaga agtcaatggt acctactatc aatttggcaa acattatgga  1500
    aacaagaaat acagaaaa                                                1518
```

<210> SEQ ID NO 21
<211> LENGTH: 2636
<212> TYPE: DNA
<213> ORGANISM: Homo sapiens
<220> FEATURE:
<221> NAME/KEY: CDS
<222> LOCATION: (266)..(1783)

<400> SEQUENCE: 21

```
    gattcggctg cggtacatct cggcactcta gctgcagccg ggagaggcct tgccgccacc    60
    gctgtcgccc aagcctccac tgccgctgcc acctcagcgc cggcctctgc atcccagct   120
    ccagctccgc tctgcgccgc tgctgccatc gccgctgcca cctccgcagc ccgggcctcc   180
    gccgccgcca cccaagcatc cgtgagtcat tttctgccca tctctggtcg cgcggtctcc   240
    ctggtagagt ttgtaggctt gcaag atg gca gaa gca gat ttt aaa atg gtc    292
                             Met Ala Glu Ala Asp Phe Lys Met Val
                               1               5
    tcg gaa cct gtc gcc cat ggg gtt gcc gaa gag gag atg gct agc tcg    340
    Ser Glu Pro Val Ala His Gly Val Ala Glu Glu Glu Met Ala Ser Ser
     10                  15                  20                  25
    act agt gat tct ggg gaa gaa tct gac agc agt agc tct agc agc agc    388
    Thr Ser Asp Ser Gly Glu Glu Ser Asp Ser Ser Ser Ser Ser Ser
                     30                  35                  40
    act agt gac agc agc agc agc agc agc act agt ggc agc agc agc ggc    436
```

```
                Thr Ser Asp Ser Ser Ser Ser Ser Thr Ser Gly Ser Ser Ser Gly
                            45                  50                  55
agc ggc agc agc agc agc agc ggc agc act agc agc agc cgc              484
Ser Gly Ser Ser Ser Ser Ser Gly Ser Thr Ser Ser Arg Ser Arg
                60                  65                  70
ttg tat aga aag aag agg gta cct gag cct tcc aga agg gcg cgg cgg      532
Leu Tyr Arg Lys Lys Arg Val Pro Glu Pro Ser Arg Arg Ala Arg Arg
            75                  80                  85
gcc ccg ttg gga aca aat ttc gtg gat agg ctg cct cag gca gtt aga      580
Ala Pro Leu Gly Thr Asn Phe Val Asp Arg Leu Pro Gln Ala Val Arg
90                  95                  100                 105
aat cgt gtg caa gcg ctt aga aac att caa gat gaa tgt gac aag gta      628
Asn Arg Val Gln Ala Leu Arg Asn Ile Gln Asp Glu Cys Asp Lys Val
                110                 115                 120
gat acc ctg ttc tta aaa gca att cat gat ctt gaa aga aaa tat gct      676
Asp Thr Leu Phe Leu Lys Ala Ile His Asp Leu Glu Arg Lys Tyr Ala
            125                 130                 135
gaa ctc aac aag cct ctg tat gat agg cgg ttt caa atc atc aat gca      724
Glu Leu Asn Lys Pro Leu Tyr Asp Arg Arg Phe Gln Ile Ile Asn Ala
        140                 145                 150
gaa tac gag cct aca gaa gaa gaa tgt gaa tgg aat tca gag gat gag      772
Glu Tyr Glu Pro Thr Glu Glu Glu Cys Glu Trp Asn Ser Glu Asp Glu
        155                 160                 165
gag ttc agc agt gat gag gag gtg cag gat aac acc cct agt gaa atg      820
Glu Phe Ser Ser Asp Glu Glu Val Gln Asp Asn Thr Pro Ser Glu Met
170                 175                 180                 185
cct ccc tta gag ggt gag gaa gaa gaa aac cct aaa gaa aac cca gag      868
Pro Pro Leu Glu Gly Glu Glu Glu Glu Asn Pro Lys Glu Asn Pro Glu
                190                 195                 200
gtg aaa gct gaa gag aag gaa gtt cct aaa gaa att cct gag gtg aag      916
Val Lys Ala Glu Glu Lys Glu Val Pro Lys Glu Ile Pro Glu Val Lys
            205                 210                 215
gat gaa gaa aag gaa gtt gct aaa gaa att cct gag gta aag gct gaa      964
Asp Glu Glu Lys Glu Val Ala Lys Glu Ile Pro Glu Val Lys Ala Glu
        220                 225                 230
gaa aaa gca gat tct aaa gac tgt atg gag gca acc cct gaa gta aaa     1012
Glu Lys Ala Asp Ser Lys Asp Cys Met Glu Ala Thr Pro Glu Val Lys
        235                 240                 245
gaa gat cct aaa gaa gtc ccc cag gta aag gca gat gat aaa gaa cag     1060
Glu Asp Pro Lys Glu Val Pro Gln Val Lys Ala Asp Asp Lys Glu Gln
250                 255                 260                 265
cct aaa gca aca gag gct aag gca agg gct gca gta aga gag act cat     1108
Pro Lys Ala Thr Glu Ala Lys Ala Arg Ala Ala Val Arg Glu Thr His
                270                 275                 280
aaa aga gtt cct gag gaa agg ctt cgg gac agt gta gat ctt aaa aga     1156
Lys Arg Val Pro Glu Glu Arg Leu Arg Asp Ser Val Asp Leu Lys Arg
            285                 290                 295
gct agg aag gga aag cct aaa aga gaa gac cct aaa ggc att cct gac     1204
Ala Arg Lys Gly Lys Pro Lys Arg Glu Asp Pro Lys Gly Ile Pro Asp
        300                 305                 310
tat tgg ctg att gtt tta aag aat gtt gac aag ctc ggg cct atg att     1252
Tyr Trp Leu Ile Val Leu Lys Asn Val Asp Lys Leu Gly Pro Met Ile
        315                 320                 325
cag aag tat gat gag ccc att ctg aag ttc ttg tcg gat gtt agc ctg     1300
Gln Lys Tyr Asp Glu Pro Ile Leu Lys Phe Leu Ser Asp Val Ser Leu
330                 335                 340                 345
aag ttc tca aaa cct ggc cag cct gta agt tac acc ttt gaa ttt cat     1348
Lys Phe Ser Lys Pro Gly Gln Pro Val Ser Tyr Thr Phe Glu Phe His
                350                 355                 360
ttt cta ccc aac cca tac ttc aga aat gag gtg ctg gtg aag aca tat     1396
Phe Leu Pro Asn Pro Tyr Phe Arg Asn Glu Val Leu Val Lys Thr Tyr
            365                 370                 375
ata ata aag gca aaa cca gat cac aat gat ccc ttc ttt tct tgg gga     1444
Ile Ile Lys Ala Lys Pro Asp His Asn Asp Pro Phe Phe Ser Trp Gly
        380                 385                 390
tgg gaa att gaa gat tgc aaa ggc tgc aag ata gac cgg aga aga gga     1492
Trp Glu Ile Glu Asp Cys Lys Gly Cys Lys Ile Asp Arg Arg Arg Gly
        395                 400                 405
aaa gat gtt act gtg aca act acc cag agt cgc aca act gct act gga     1540
Lys Asp Val Thr Val Thr Thr Thr Gln Ser Arg Thr Thr Ala Thr Gly
410                 415                 420                 425
gaa att gaa atc cag cca aga gtg gtt cct aat gca tca ttc ttc aac     1588
Glu Ile Glu Ile Gln Pro Arg Val Val Pro Asn Ala Ser Phe Phe Asn
                430                 435                 440
ttc ttt agt cct cct gag att cct atg att ggg aag ctg gaa cca cga     1636
Phe Phe Ser Pro Pro Glu Ile Pro Met Ile Gly Lys Leu Glu Pro Arg
            445                 450                 455
gaa gat gct atc ctg gat gag gac ttt gaa att ggg cag att tta cat     1684
Glu Asp Ala Ile Leu Asp Glu Asp Phe Glu Ile Gly Gln Ile Leu His
```

-continued

```
                       460                 465                 470
        gat aat gtc atc ctg aaa tca atc tat tac tat act gga gaa gtc aat      1732
        Asp Asn Val Ile Leu Lys Ser Ile Tyr Tyr Tyr Thr Gly Glu Val Asn
                       475                 480                 485
        ggt acc tac tat caa ttt ggc aaa cat tat gga aac aag aaa tac aga      1780
        Gly Thr Tyr Tyr Gln Phe Gly Lys His Tyr Gly Asn Lys Lys Tyr Arg
        490                 495                 500                 505
        aaa taagtcaatc tgaaagattt ttcaagaatc ttaaaatctc aagaagtgaa           1833
        Lys
        gcagattcat acagccttga aaaaagtaaa accctgacct gtaacctgaa cactattatt    1893
        ccttatagtc aagtttttgt ggtttcttgg tagtctatat tttaaaaata gtcctaaaaa    1953
        gtgtctaagt gccagttttat tctatctagg ctgttgtagt ataatattct tcaaaatatg   2013
        taagctgttg tcaattatct aaagcatgtt agtttggtgc tacacagtgt tgattttgt     2073
        gatgtccttt ggtcatgttt ctgttagact gtagctgtga aactgtcaga attgttaact    2133
        gaaacaaata tttgcttgaa aaaaaaagtt catgaagtac caatgcaagt gtttttatttt   2193
        ttttcttttt tccagcccat aagactaagg gtttaaatct gcttgcacta gctgtgccttt   2253
        cattagtttg ctatagaaat ccagtactta tagtaaataa aacagtgtat tttgaagttt    2313
        gactgcttga aaaagattag catacatcta atgtgaaaag accacatttg attcaactga    2373
        gaccttgtgt atgtgacata tagtggccta taaatttaat cataatgatg ttattgttta    2433
        ccactgaggt gttaaataaa catagtattt ttgaaaaagt ttcttcatct tatattgtgt    2493
        aattgtaaac taaagatacc gtgttttctt tgtattgtgt tctaccttcc ctttcactga    2553
        aaatgatcac ttcatttgat actgtttttc atgttcttgt attgcaacct aaaataaata    2613
        aatattaaag tgtgttatac tat                                            2636
```

<210> SEQ ID NO 22
<211> LENGTH: 170
<212> TYPE: PRT
<213> ORGANISM: Homo sapiens

<400> SEQUENCE: 22

```
        Met Thr Glu Leu Gln Ser Ala Leu Leu Arg Arg Gln Leu Ala Glu
        1               5                  10                  15
        Leu Asn Lys Asn Pro Val Glu Gly Phe Ser Ala Gly Leu Ile Asp Asp
                        20                  25                  30
        Asn Asp Leu Tyr Arg Trp Glu Val Leu Ile Ile Gly Pro Pro Asp Thr
                    35                  40                  45
        Leu Tyr Glu Gly Gly Val Phe Lys Ala His Leu Thr Phe Pro Lys Asp
                50                  55                  60
        Tyr Pro Leu Arg Pro Pro Lys Met Lys Phe Ile Thr Glu Ile Trp His
        65                  70                  75                  80
        Pro Asn Val Asp Lys Asn Gly Asp Val Cys Ile Ser Ile Leu His Glu
                        85                  90                  95
        Pro Gly Glu Asp Lys Tyr Gly Tyr Glu Lys Pro Glu Glu Arg Trp Leu
                    100                 105                 110
        Pro Ile His Thr Val Glu Thr Ile Met Ile Ser Val Ile Ser Met Leu
                115                 120                 125
        Ala Asp Pro Asn Gly Asp Ser Pro Ala Asn Val Asp Ala Ala Lys Glu
            130                 135                 140
        Trp Arg Glu Asp Arg Asn Gly Glu Phe Lys Arg Lys Val Ala Arg Cys
        145                 150                 155                 160
        Val Arg Lys Ser Gln Glu Thr Ala Phe Glu
                        165                 170
```

<210> SEQ ID NO 23
<211> LENGTH: 510
<212> TYPE: DNA
<213> ORGANISM: Homo sapiens

<400> SEQUENCE: 23

```
        atgacggagc tgcagtcggc actgctactg cgaagacagc tggcagaact caacaaaaat    60
        ccagtggaag ctttttctgc aggtttaata gatgacaatg atctctaccg atgggaagtc    120
        cttattattg gcccctccaga tacactttat gaaggtggtg ttttaaggc tcatcttact    180
        ttcccaaaag attatcccct ccgacctcct aaaatgaaat tcattacaga aatctggcac    240
        ccaaatgttg ataaaaatgg tgatgtgtgc atttctattc ttcatgagcc tggggaagat    300
        aagtatggtt atgaaaagcc agaggaacgc tggctcccta tccacactgt ggaaaccatc    360
        atgattagtg tcatttctat gctggcagac cctaatggag actcacctgc taatgttgat    420
        gctgcgaaag aatggaggga agatagaaat ggagaatttta aagaaaagt tgcccgctgt    480
        gtaagaaaaa gccaagagac tgctttttgag                                    510
```

<210> SEQ ID NO 24
<211> LENGTH: 617
<212> TYPE: DNA
<213> ORGANISM: Homo sapiens
<220> FEATURE:

```
<221> NAME/KEY: CDS
<222> LOCATION: (19)..(528)

<400> SEQUENCE: 24
gggccctcgg cagggagg atg acg gag ctg cag tcg gca ctg cta ctg cga    51
                        Met Thr Glu Leu Gln Ser Ala Leu Leu Leu Arg
                         1               5                  10
    aga cag ctg gca gaa ctc aac aaa aat cca gtg gaa ggc ttt tct gca    99
    Arg Gln Leu Ala Glu Leu Asn Lys Asn Pro Val Glu Gly Phe Ser Ala
                 15                  20                  25
    ggt tta ata gat gac aat gat ctc tac cga tgg gaa gtc ctt att att   147
    Gly Leu Ile Asp Asp Asn Asp Leu Tyr Arg Trp Glu Val Leu Ile Ile
             30                  35                  40
    ggc cct cca gat aca ctt tat gaa ggt ggt gtt ttt aag gct cat ctt   195
    Gly Pro Pro Asp Thr Leu Tyr Glu Gly Gly Val Phe Lys Ala His Leu
         45                  50                  55
    act ttc cca aaa gat tat ccc ctc cga cct cct aaa atg aaa ttc att   243
    Thr Phe Pro Lys Asp Tyr Pro Leu Arg Pro Pro Lys Met Lys Phe Ile
     60                  65                  70                  75
    aca gaa atc tgg cac cca aat gtt gat aaa aat ggt gat gtg tgc att   291
    Thr Glu Ile Trp His Pro Asn Val Asp Lys Asn Gly Asp Val Cys Ile
                 80                  85                  90
    tct att ctt cat gag cct ggg gaa gat aag tat ggt tat gaa aag cca   339
    Ser Ile Leu His Glu Pro Gly Glu Asp Lys Tyr Gly Tyr Glu Lys Pro
                 95                 100                 105
    gag gaa cgc tgg ctc cct atc cac act gtg gaa acc atc atg att agt   387
    Glu Glu Arg Trp Leu Pro Ile His Thr Val Glu Thr Ile Met Ile Ser
                110                 115                 120
    gtc att tct atg ctg gca gac cct aat gga gac tca cct gct aat gtt   435
    Val Ile Ser Met Leu Ala Asp Pro Asn Gly Asp Ser Pro Ala Asn Val
    125                 130                 135
    gat gct gcg aaa gaa tgg agg gaa gat aga aat gga gaa ttt aaa aga   483
    Asp Ala Ala Lys Glu Trp Arg Glu Asp Arg Asn Gly Glu Phe Lys Arg
    140                 145                 150                 155
    aaa gtt gcc cgc tgt gta aga aaa agc caa gag act gct ttt gag       528
    Lys Val Ala Arg Cys Val Arg Lys Ser Gln Glu Thr Ala Phe Glu
                    160                 165                 170
    tgacatttat ttagcagcta gtaacttcac ttatttcagg gtctccaatt gagaaacatg  588
    gcactgtttt tcctgcactc tacccaccg                                    617

<210> SEQ ID NO 25
<211> LENGTH: 374
<212> TYPE: PRT
<213> ORGANISM: Homo sapiens

<400> SEQUENCE: 25

Met Val Leu Trp Glu Ser Pro Arg Gln Cys Ser Ser Trp Thr Leu Cys
     1               5                  10                  15
    Glu Gly Phe Cys Trp Leu Leu Leu Pro Val Met Leu Leu Ile Val
                 20                  25                  30
    Ala Arg Pro Val Lys Leu Ala Ala Phe Pro Thr Ser Leu Ser Asp Cys
                 35                  40                  45
    Gln Thr Pro Thr Gly Trp Asn Cys Ser Gly Tyr Asp Asp Arg Glu Asn
             50                  55                  60
    Asp Leu Phe Leu Cys Asp Thr Asn Thr Cys Lys Phe Asp Gly Glu Cys
     65                  70                  75                  80
    Leu Arg Ile Gly Asp Thr Val Thr Cys Val Cys Gln Phe Lys Cys Asn
                     85                  90                  95
    Asn Asp Tyr Val Pro Val Cys Gly Ser Asn Gly Glu Ser Tyr Gln Asn
                100                 105                 110
    Glu Cys Tyr Leu Arg Gln Ala Ala Cys Lys Gln Gln Ser Glu Ile Leu
                115                 120                 125
    Val Val Ser Glu Gly Ser Cys Ala Thr Asp Ala Gly Ser Gly Ser Gly
    130                 135                 140
    Asp Gly Val His Glu Gly Ser Gly Glu Thr Ser Gln Lys Gly Thr Ser
    145                 150                 155                 160
    Thr Cys Asp Ile Cys Gln Phe Gly Ala Glu Cys Asp Glu Asp Ala Glu
                    165                 170                 175
    Asp Val Trp Cys Val Cys Asn Ile Asp Cys Ser Gln Thr Asn Phe Asn
                180                 185                 190
    Pro Leu Cys Ala Ser Asp Gly Lys Ser Tyr Asp Asn Ala Cys Gln Ile
                195                 200                 205
    Lys Glu Ala Ser Cys Gln Lys Gln Glu Lys Ile Glu Val Met Ser Leu
    210                 215                 220
    Gly Arg Cys Gln Asp Asn Thr Thr Thr Thr Lys Ser Glu Asp Gly
    225                 230                 235                 240
```

```
    His Tyr Ala Arg Thr Asp Tyr Ala Glu Asn Ala Asn Lys Leu Glu Glu
                    245                 250                 255
    Ser Ala Arg Glu His His Ile Pro Cys Pro Glu His Tyr Asn Gly Phe
                260                 265                 270
    Cys Met His Gly Lys Cys Glu His Ser Ile Asn Met Gln Glu Pro Ser
            275                 280                 285
    Cys Arg Cys Asp Ala Gly Tyr Thr Gly Gln His Cys Glu Lys Lys Asp
        290                 295                 300
    Tyr Ser Val Leu Tyr Val Val Pro Gly Pro Val Arg Phe Gln Tyr Val
    305                 310                 315                 320
    Leu Ile Ala Ala Val Ile Gly Thr Ile Gln Ile Ala Val Ile Cys Val
                    325                 330                 335
    Val Val Leu Cys Ile Thr Arg Lys Cys Pro Arg Ser Asn Arg Ile His
                340                 345                 350
    Arg Gln Lys Gln Asn Thr Gly His Tyr Ser Ser Asp Asn Thr Thr Arg
            355                 360                 365
    Ala Ser Thr Arg Leu Ile
        370
```

<210> SEQ ID NO 26
<211> LENGTH: 1122
<212> TYPE: DNA
<213> ORGANISM: Homo sapiens

<400> SEQUENCE: 26

```
atggtgctgt gggagtcccc gcggcagtgc agcagctgga cactttgcga gggcttttgc    60
tggctgctgc tgctgcccgt catgctactc atcgtagccc gcccggtgaa gctcgctgct   120
ttccctacct cccttaagtg actgccaaacg cccaccggct ggaattgctc tggttatgat   180
gacagagaaa atgatctctt cctctgtgac accaacacct gtaaatttga tggggaatgt   240
ttaagaattg agacactgt gacttgcgtc tgtcagttca agtgcaacaa tgactatgtg   300
cctgtgtgtg gctccaatgg ggagagctac cagaatgagt gttacctgcg acaggctgca   360
tgcaaacagc agagtgagat acttgtggtg tcagaaggat catgtgccac agatgcagga   420
tcaggatctg gagatggagt ccatgaaggc tctggagaaa ctagtcaaaa ggagacatcc   480
acctgtgtga tttgccagtt tggtgcagaa tgtgacgaag atgccgagga tgtctggtgt   540
gtgtgtaata ttgactgttc tcaaaccaac ttcaatcccc tctgcgcttc tgatgggaaa   600
tcttatgata atgcatgcca aatcaaagaa gcatcgtgtc agaaacagga gaaattgaa    660
gtcatgtctt tgggtcgatg tcaagataac acaactacaa ctactaagtc tgaagatggg   720
cattatgcaa gaacagatta tgcagagaat gctaacaaat tagaagaaag tgccagagaa   780
caccacatac cttgtccgga acattacaat ggcttctgca tgcatgggaa gtgtgagcat   840
tctatcaata tgcaggagcc atcttcagg tgtgatgctg gttactgcg acaacactgt    900
gaaaaaaagg actacagtgt tctatacgtt gttcccggtc ctgtacgatt tcagtatgtc   960
ttaatcgcag ctgtgattgg aacaattcag attgctgtca tctgtgtggt ggtcctctgc  1020
atcacaagga aatgcccag aagcaacaga attcacagac agaagcaaaa tacagggcac   1080
tacagttcag acaatacaac aagagcgtcc acgaggttaa tc                     1122
```

<210> SEQ ID NO 27
<211> LENGTH: 1721
<212> TYPE: DNA
<213> ORGANISM: Homo sapiens
<220> FEATURE:
<221> NAME/KEY: CDS
<222> LOCATION: (368)..(1489)

<400> SEQUENCE: 27

```
ctgcggggcg ccttgactct ccctccaccc tgcctcctcg ggctccactc gtctgcccct    60
ggactcccgt ctcctcctgt cctccggctt cccagagctc cctccttatg cagcagctt   120
cccgcgtctc cggcgcagct tctcagcgga cgaccctctc gtccggggc tgagccagtc   180
cctggatgtt gctgaaactc tcgagatcat gcgcgggttt ggctgctgct tccccgccgg   240
gtgccactgc caccgccgcc gcctctgctg ccgccgtccg cgggatgctc agtagcccgc   300
tgcccggccc ccgcgatcct gtgttcctcg gaagccgttt gctgctgcag agttgcacga   360
actagtc atg gtg ctg tgg gag tcc ccg cgg cag tgc agc agc tgg aca    409
        Met Val Leu Trp Glu Ser Pro Arg Gln Cys Ser Ser Trp Thr
         1               5                  10
ctt tgc gag ggc ttt tgc tgg ctg ctg ctg ccc gtc atg cta ctc        457
Leu Cys Glu Gly Phe Cys Trp Leu Leu Leu Pro Val Met Leu Leu
 15                 20                  25                  30
atc gta gcc cgc ccg gtg aag ctc gct gct ttc cct acc tcc tta agt    505
Ile Val Ala Arg Pro Val Lys Leu Ala Ala Phe Pro Thr Ser Leu Ser
                35                  40                  45
gac tgc caa acg ccc acc ggc tgg aat tgc tct ggt tat gat gac aga    553
Asp Cys Gln Thr Pro Thr Gly Trp Asn Cys Ser Gly Tyr Asp Asp Arg
            50                  55                  60
gaa aat gat ctc ttc ctc tgt gac acc aac acc tgt aaa ttt gat ggg    601
Glu Asn Asp Leu Phe Leu Cys Asp Thr Asn Thr Cys Lys Phe Asp Gly
65                  70                  75
```

-continued

```
gaa tgt tta aga att gga gac act gtg act tgc gtc tgt cag ttc aag     649
Glu Cys Leu Arg Ile Gly Asp Thr Val Thr Cys Val Cys Gln Phe Lys
         80                  85                  90
tgc aac aat gac tat gtg cct gtg tgt ggc tcc aat ggg gag agc tac     697
Cys Asn Asn Asp Tyr Val Pro Val Cys Gly Ser Asn Gly Glu Ser Tyr
 95                 100                 105                 110
cag aat gag tgt tac ctg cga cag gct gca tgc aaa cag cag agt gag     745
Gln Asn Glu Cys Tyr Leu Arg Gln Ala Ala Cys Lys Gln Gln Ser Glu
                115                 120                 125
ata ctt gtg gtg tca gaa gga tca tgt gcc aca gat gca gga tca gga     793
Ile Leu Val Val Ser Glu Gly Ser Cys Ala Thr Asp Ala Gly Ser Gly
            130                 135                 140
tct gga gat gga gtc cat gaa ggc tct gga gaa act agt caa aag gag     841
Ser Gly Asp Gly Val His Glu Gly Ser Gly Glu Thr Ser Gln Lys Glu
        145                 150                 155
aca tcc acc tgt gat att tgc cag ttt ggt gca gaa tgt gac gaa gat     889
Thr Ser Thr Cys Asp Ile Cys Gln Phe Gly Ala Glu Cys Asp Glu Asp
    160                 165                 170
gcc gag gat gtc tgg tgt gtg tgt aat att gac tgt tct caa acc aac     937
Ala Glu Asp Val Trp Cys Val Cys Asn Ile Asp Cys Ser Gln Thr Asn
175                 180                 185                 190
ttc aat ccc ctc tgc gct tct gat ggg aaa tct tat gat aat gca tgc     985
Phe Asn Pro Leu Cys Ala Ser Asp Gly Lys Ser Tyr Asp Asn Ala Cys
                195                 200                 205
caa atc aaa gaa gca tcg tgt cag aaa cag gag aaa att gaa gtc atg    1033
Gln Ile Lys Glu Ala Ser Cys Gln Lys Gln Glu Lys Ile Glu Val Met
            210                 215                 220
tct ttg ggt cga tgt caa gat aac aca act act act aag tct gaa        1081
Ser Leu Gly Arg Cys Gln Asp Asn Thr Thr Thr Thr Lys Ser Glu
        225                 230                 235
gat ggg cat tat gca aga aca gat tat gca gag aat gct aac aaa tta    1129
Asp Gly His Tyr Ala Arg Thr Asp Tyr Ala Glu Asn Ala Asn Lys Leu
    240                 245                 250
gaa gaa agt gcc aga gaa cac cac ata cct tgt ccg gaa cat tac aat    1177
Glu Glu Ser Ala Arg Glu His His Ile Pro Cys Pro Glu His Tyr Asn
255                 260                 265                 270
ggc ttc tgc atg cat ggg aag tgt gag cat tct atc aat atg cag gag    1225
Gly Phe Cys Met His Gly Lys Cys Glu His Ser Ile Asn Met Gln Glu
                275                 280                 285
cca tct tgc agg tgt gat gct ggt tat act gga caa cac tgt gaa aaa    1273
Pro Ser Cys Arg Cys Asp Ala Gly Tyr Thr Gly Gln His Cys Glu Lys
            290                 295                 300
aag gac tac agt gtt cta tac gtt gtt ccc ggt cct gta cga ttt cag    1321
Lys Asp Tyr Ser Val Leu Tyr Val Val Pro Gly Pro Val Arg Phe Gln
        305                 310                 315
tat gtc tta atc gca gct gtg att gga aca att cag att gct gtc atc    1369
Tyr Val Leu Ile Ala Ala Val Ile Gly Thr Ile Gln Ile Ala Val Ile
    320                 325                 330
tgt gtg gtg gtc ctc tgc atc aca agg aaa tgc ccc aga agc aac aga    1417
Cys Val Val Val Leu Cys Ile Thr Arg Lys Cys Pro Arg Ser Asn Arg
335                 340                 345                 350
att cac aga cag aag caa aat aca ggg cac tac agt tca gac aat aca    1465
Ile His Arg Gln Lys Gln Asn Thr Gly His Tyr Ser Ser Asp Asn Thr
                355                 360                 365
aca aga gcg tcc acg agg tta atc taaagggagc atgtttcaca gtggctggac  1519
Thr Arg Ala Ser Thr Arg Leu Ile
            370
taccgagagc ttggactaca caatacagta ttatagacaa agaataaga caagagatct  1579
acacatgttg ccttgcattt gtggtaatct acaccaatga aaacatgtac tacagctata  1639
tttgattatg tatggatata tttgaaatag tatacattgt cttgatgttt tttctgtaat  1699
gtaaataaac tatttatatc ac                                          1721
```

<210> SEQ ID NO 28
<211> LENGTH: 817
<212> TYPE: PRT
<213> ORGANISM: Homo sapiens

<400> SEQUENCE: 28

```
Met Gly Asp Thr Val Val Glu Pro Ala Pro Leu Lys Pro Thr Ser Glu
  1               5                  10                  15
Pro Thr Ser Gly Pro Pro Gly Asn Asn Gly Gly Ser Leu Leu Ser Val
                 20                  25                  30
Ile Thr Glu Gly Val Gly Glu Leu Ser Val Ile Asp Pro Glu Val Ala
             35                  40                  45
Gln Lys Ala Cys Gln Glu Val Leu Glu Lys Val Lys Leu Leu His Gly
         50                  55                  60
Gly Val Ala Val Ser Ser Arg Gly Thr Pro Leu Glu Leu Val Asn Gly
```

```
            65                  70                  75                  80
        Asp Gly Val Asp Ser Glu Ile Arg Cys Leu Asp Asp Pro Pro Ala Gln
                         85                  90                  95
        Ile Arg Glu Glu Asp Glu Met Gly Ala Ala Val Ala Ser Gly Thr
                    100                 105                 110
        Ala Lys Gly Ala Arg Arg Arg Gln Asn Asn Ser Ala Lys Gln Ser
                115                 120                 125
        Trp Leu Leu Arg Leu Phe Glu Ser Lys Leu Phe Asp Ile Ser Met Ala
            130                 135                 140
        Ile Ser Tyr Leu Tyr Asn Ser Lys Glu Pro Gly Val Gln Ala Tyr Ile
        145                 150                 155                 160
        Gly Asn Arg Leu Phe Cys Phe Arg Asn Glu Asp Val Asp Phe Tyr Leu
                        165                 170                 175
        Pro Gln Leu Leu Asn Met Tyr Ile His Met Asp Glu Asp Val Gly Asp
                    180                 185                 190
        Ala Ile Lys Pro Tyr Ile Val His Arg Cys Arg Gln Ser Ile Asn Phe
                195                 200                 205
        Ser Leu Gln Cys Ala Leu Leu Leu Gly Ala Tyr Ser Ser Asp Met His
            210                 215                 220
        Ile Ser Thr Gln Arg His Ser Arg Gly Thr Lys Leu Arg Lys Leu Ile
        225                 230                 235                 240
        Leu Ser Asp Glu Leu Lys Pro Ala His Arg Lys Arg Glu Leu Pro Ser
                        245                 250                 255
        Leu Ser Pro Ala Pro Asp Thr Gly Leu Ser Pro Ser Lys Arg Thr His
                    260                 265                 270
        Gln Arg Ser Lys Ser Asp Ala Thr Ala Ser Ile Ser Leu Ser Ser Asn
                275                 280                 285
        Leu Lys Arg Thr Ala Ser Asn Pro Lys Val Glu Asn Glu Asp Glu Glu
            290                 295                 300
        Leu Ser Ser Ser Thr Glu Ser Ile Asp Asn Ser Phe Ser Ser Pro Val
        305                 310                 315                 320
        Arg Leu Ala Pro Glu Arg Glu Phe Ile Lys Ser Leu Met Ala Ile Gly
                        325                 330                 335
        Lys Arg Leu Ala Thr Leu Pro Thr Lys Glu Gln Lys Thr Gln Arg Leu
                    340                 345                 350
        Ile Ser Glu Leu Ser Leu Leu Asn His Lys Leu Pro Ala Arg Val Trp
                355                 360                 365
        Leu Pro Thr Ala Gly Phe Asp His His Val Arg Val Pro His Thr
            370                 375                 380
        Gln Ala Val Val Leu Asn Ser Lys Asp Lys Ala Pro Tyr Leu Ile Tyr
        385                 390                 395                 400
        Val Glu Val Leu Glu Cys Glu Asn Phe Asp Thr Thr Ser Val Pro Ala
                        405                 410                 415
        Arg Ile Pro Glu Asn Arg Ile Arg Ser Thr Arg Ser Val Asp Asn Leu
                    420                 425                 430
        Pro Glu Cys Gly Ile Thr His Glu Gln Arg Ala Gly Ser Phe Ser Thr
                435                 440                 445
        Val Pro Asn Tyr Asp Asn Asp Asp Glu Ala Trp Ser Val Asp Asp Ile
            450                 455                 460
        Gly Glu Leu Gln Val Glu Leu Pro Glu Val His Thr Asn Ser Cys Asp
        465                 470                 475                 480
        Asn Ile Ser Gln Phe Ser Val Asp Ser Ile Thr Ser Gln Glu Ser Lys
                        485                 490                 495
        Glu Pro Val Phe Ile Ala Ala Gly Asp Ile Arg Arg Arg Leu Ser Glu
                    500                 505                 510
        Gln Leu Ala His Thr Pro Thr Ala Phe Lys Arg Asp Pro Glu Asp Pro
                515                 520                 525
        Ser Ala Val Ala Leu Lys Glu Pro Trp Gln Glu Lys Val Arg Arg Ile
            530                 535                 540
        Arg Glu Gly Ser Pro Tyr Gly His Leu Pro Asn Trp Arg Leu Leu Ser
        545                 550                 555                 560
        Val Ile Val Lys Cys Gly Asp Asp Leu Arg Gln Glu Leu Leu Ala Phe
                        565                 570                 575
        Gln Val Leu Lys Gln Leu Gln Ser Ile Trp Glu Gln Glu Arg Val Pro
                    580                 585                 590
        Leu Trp Ile Lys Pro Ile Gln Asp Ser Cys Glu Ile Thr Thr Asp Ser
                595                 600                 605
        Gly Met Ile Glu Pro Val Val Asn Ala Val Ser Ile His Gln Val Lys
            610                 615                 620
        Lys Gln Ser Gln Leu Ser Leu Asp Tyr Phe Leu Gln Glu His Gly
        625                 630                 635                 640
        Ser Tyr Thr Thr Glu Ala Phe Leu Ser Ala Gln Arg Asn Phe Val Gln
                        645                 650                 655
        Ser Cys Ala Gly Tyr Cys Leu Val Cys Tyr Leu Leu Gln Val Lys Asp
                    660                 665                 670
        Arg His Asn Gly Asn Ile Leu Leu Asp Ala Glu Gly His Ile Ile His
                675                 680                 685
        Ile Asp Phe Gly Phe Ile Leu Ser Ser Ser Pro Arg Asn Leu Gly Phe
            690                 695                 700
```

```
      Glu Thr Ser Ala Phe Lys Leu Thr Glu Phe Val Asp Val Met Gly
      705                 710                 715                 720
      Gly Leu Asp Gly Asp Met Phe Asn Tyr Tyr Lys Met Leu Met Leu Gln
                      725                 730                 735
      Gly Leu Ile Ala Ala Arg Lys His Met Asp Lys Val Val Gln Ile Val
                  740                 745                 750
      Glu Ile Met Gln Gln Gly Ser Gln Leu Pro Cys Phe His Gly Ser Ser
              755                 760                 765
      Thr Ile Arg Asn Leu Lys Glu Arg Phe His Met Ser Met Thr Glu Glu
          770                 775                 780
      Gln Leu Gln Leu Leu Val Glu Gln Met Val Asp Gly Ser Met Arg Ser
      785                 790                 795                 800
      Ile Thr Thr Lys Leu Tyr Asp Gly Phe Gln Tyr Leu Thr Asn Gly Ile
                          805                 810                 815
      Met
```

<210> SEQ ID NO 29
<211> LENGTH: 2451
<212> TYPE: DNA
<213> ORGANISM: Homo sapiens

<400> SEQUENCE: 29

```
      atgggagata cagtagtgga gcctgccccc ttgaagccaa cttctgagcc cacttctggc   60
      ccaccaggga ataatggggg gtccctgcta agtgtcatca cggagggggt cggggaacta  120
      tcagtgattg accctgaggt ggcccagaag gcctgccagg aggtgttgga aaagtcaag   180
      cttttgcatg gaggcgtggc agtctctagc agaggcaccc cactggagtt ggtcaatggg  240
      gatggtgtgg acagtgagat ccgttgccta gatgatccac ctgcccagat cagggaggag  300
      gaagatgaga tgggggccgc tgtggcctca ggcacagcca aggagcaag aagacggcgg   360
      cagaacaact cagctaaaca gtcttggctg ctgaggctgt ttgagtcaaa actgtttgac  420
      atctccatgg ccatttcata cctgtataac tccaaggacg ctgagtaca agcctacatt   480
      ggcaaccggc tcttctgctt tcgcaacgag gacgtggact tctatctgcc ccagttgctt  540
      aacatgtaca tccacatgga tgaggacgtg ggtgatgcca ttaagcccta catagtccac  600
      cgttgccgcc agagcattaa cttttccctc cagtgtgccc tgttgcttgg ggcctattct  660
      tcagacatgc acatttccac tcaacgacat cccgtgacg caagctacg gaagctgatc   720
      ctctcagatg agctaaagcc agctcacagg aagagggagc tgccctcctt gagcccggcc  780
      cctgatacag ggctgtctcc ctccaaaagg actcaccagc gctcaagtc agatgccact   840
      gccagcataa gtctcagcag caacctgaaa cgaacagcca gcaacctaa agtgggagaat  900
      gaggatgagg agctctcctc cagcaccgag agtattgata attcattcag ttccctgttt  960
      cgactggctc ctgagagaga attcatcaag tccctgatgg cgatcggcaa gcggctggcc 1020
      acgctcccca ccaaaagagca gaaaacacag aggctgatct cagagctctc cctgctcaac 1080
      cataagctcc ctgcccgagt ctggctgccc actgctggct ttgaccacca cgtggtccgt 1140
      gtaccccaca cacaggctgt tgtcctcaac tccaaggaca aggctcccta cctgattttat 1200
      gtggaagtcc ttgaatgtga aactttggac accaccagtg tccctgcccg gatccccgag 1260
      aaccgaattc ggagtacgag gtccgtagaa aacttgcccg aatgtggtat tacccatgag 1320
      cagcgagctg gcagcttcag cactgtgccc aactatgaca cgatgatga ggcctggtcg  1380
      gtggatgaca taggcagct gcaagtggag ctccccgaag tgcataccaa cagctgtgac 1440
      aacatctccc agttctctgt ggacagcatc accagccagg agacaaggga gcctgtgttc 1500
      attgcagcag ggacatccg ccggcgcctt tcggaacagc tggctcatac cccgacagcc 1560
      ttcaaacgag acccagaaga tccttctgca gttgctctca aagagccctg caggagaaa  1620
      gtacggcgga tcagagaggg ctccccctac ggccatctcc ccaattggcg gctcctgtca 1680
      gtcattgtca agtgtgggga tgaccttcgg caagagcttc ggcctttca ggtgttgaag 1740
      caactgcagt ccatttggga acaggagcga gtgccccttt ggatcaagcc aatacaagat 1800
      tctttgtgaaa ttacgactga tagtggcatg attgaaccag tggtcaatgc tgtgtccatc 1860
      catcaggtga agaaacagtc acagctctcc ttgctcgatt acttcctaca ggagcacggc 1920
      agttacacca ctgaggcatt cctcagtgca cagcgcaatt tgtgcaaag ttgtgctggg 1980
      tactgcttgg tctgctacct gctgcaagtc aaggacagac acaatgggaa tatcctttgt 2040
      gacgcagaag gccacatcat ccacatcgac tttggcttca tcctctccag ctcaccccga 2100
      aatctgggct tgagacgtc agcctttaag ctgaccacag agtttgtgga tgtgatgggc 2160
      ggcctggatg gcgacatgtt caactactat aagtagctga tgctgcaagg gctgattgcc 2220
      gctcggaaac acatggacaa ggtggtgcag atcgtggaga tcatgcagca aggttctcag 2280
      cttccttgct tccatggctc cagcaccatt cgaaacctca agagaggtt ccacatgagc 2340
      atgactgagg agcagctgca gctgctggtg gagcagatgg tggatggcag tatgcggtct 2400
      atcaccacca aactctatga cggcttccag tacctcacca acggcatcat g           2451
```

<210> SEQ ID NO 30
<211> LENGTH: 3602
<212> TYPE: DNA
<213> ORGANISM: Homo sapiens
<220> FEATURE:
<221> NAME/KEY: CDS
<222> LOCATION: (429)..(2879)

<400> SEQUENCE: 30

```
      ggtggctcac gcctgtaatc ccagcacttt gggaggacaa ggcagatccc ttgagcccag   60
      gaggtagagg ctgcagtgag ctgtgatggt gccactgcac tccagcctgg gcaatgaagc  120
```

```
aagaccctat ctgaaaaaaa aaattttaa aaaaggcaaa gatgggcctg gggcaccaaa    180
tattccagag gaaagggaac gtgtgtactc cttgaggtgg ggaacatgac ccacttgagg   240
tgcagaaaga agacttgtat ggggctggtg cagcctccgc ggccgctgtc agggaagcgc   300
aggcggccaa tggaacccgg gagcggtcgc tgctgctgag gcggcagtgt cggcagtcca   360
accgcgactg cccgcacccc ctccgcgggg tccccagag cttggaagct cgaagtctgg    420
ctgtggcc atg gga gat aca gta gtg gag cct gcc ccc ttg aag cca act    470
         Met Gly Asp Thr Val Val Glu Pro Ala Pro Leu Lys Pro Thr
          1               5                  10
tct gag ccc act tct ggc cca cca ggg aat aat ggg ggg tcc ctg cta     518
Ser Glu Pro Thr Ser Gly Pro Pro Gly Asn Asn Gly Gly Ser Leu Leu
 15              20                  25                  30
agt gtc atc acg gag ggg gtc ggg gaa cta tca gtg att gac cct gag     566
Ser Val Ile Thr Glu Gly Val Gly Glu Leu Ser Val Ile Asp Pro Glu
                     35                  40                  45
gtg gcc cag aag gcc tgc cag gag gtg ttg gag aaa gtc aag ctt ttg     614
Val Ala Gln Lys Ala Cys Gln Glu Val Leu Glu Lys Val Lys Leu Leu
                 50                  55                  60
cat gga ggc gtg gca gtc tct agc aga ggc acc cca ctg gag ttg gtc     662
His Gly Gly Val Ala Val Ser Ser Arg Gly Thr Pro Leu Glu Leu Val
             65                  70                  75
aat ggg gat ggt gtg gac agt gag atc cgt tgc cta gat gat cca cct     710
Asn Gly Asp Gly Val Asp Ser Glu Ile Arg Cys Leu Asp Asp Pro Pro
         80                  85                  90
gcc cag atc agg gag gag gaa gat gag atg ggg gcc gct gtg gcc tca     758
Ala Gln Ile Arg Glu Glu Glu Asp Glu Met Gly Ala Ala Val Ala Ser
 95                  100                 105                 110
ggc aca gcc aaa gga gca aga aga cgg cgg cag aac aac tca gct aaa     806
Gly Thr Ala Lys Gly Ala Arg Arg Arg Arg Gln Asn Asn Ser Ala Lys
                 115                 120                 125
cag tct tgg ctg ctg agg ctg ttt gag tca aaa ctg ttt gac atc tcc     854
Gln Ser Trp Leu Leu Arg Leu Phe Glu Ser Lys Leu Phe Asp Ile Ser
             130                 135                 140
atg gcc att tca tac ctg tat aac tcc aag gag cct gga gta caa gcc    902
Met Ala Ile Ser Tyr Leu Tyr Asn Ser Lys Glu Pro Gly Val Gln Ala
         145                 150                 155
tac att ggc aac cgg ctc ttc tgc ttt cgc aac gag gac gtg gac ttc     950
Tyr Ile Gly Asn Arg Leu Phe Cys Phe Arg Asn Glu Asp Val Asp Phe
         160                 165                 170
tat ctg ccc cag ttg ctt aac atg tac atc cac atg gat gag gac gtg    998
Tyr Leu Pro Gln Leu Leu Asn Met Tyr Ile His Met Asp Glu Asp Val
175                  180                 185                 190
ggt gat gcc att aag ccc tac ata gtc cac cgt tgc cgc cag agc att    1046
Gly Asp Ala Ile Lys Pro Tyr Ile Val His Arg Cys Arg Gln Ser Ile
                 195                 200                 205
aac ttt tcc ctc cag tgt gcc ctg ttg ctt ggg gcc tat tct tca gac    1094
Asn Phe Ser Leu Gln Cys Ala Leu Leu Leu Gly Ala Tyr Ser Ser Asp
             210                 215                 220
atg cac att tcc act caa cga cac tcc cgt ggg acc aag cta cgg aag    1142
Met His Ile Ser Thr Gln Arg His Ser Arg Gly Thr Lys Leu Arg Lys
         225                 230                 235
ctg atc ctc tca gat gag cta aag cca gct cac agg aag agg gag ctg    1190
Leu Ile Leu Ser Asp Glu Leu Lys Pro Ala His Arg Lys Arg Glu Leu
240                  245                 250
ccc tcc ttg agc ccg gcc cct gat aca ggg ctg tct ccc tcc aaa agg    1238
Pro Ser Leu Ser Pro Ala Pro Asp Thr Gly Leu Ser Pro Ser Lys Arg
255                  260                 265                 270
act cac cag cgc tct aag tca gat gcc act gcc agc ata agt ctc agc    1286
Thr His Gln Arg Ser Lys Ser Asp Ala Thr Ala Ser Ile Ser Leu Ser
                 275                 280                 285
agc aac ctg aaa cga aca gcc agc aac cct aaa gtg gag aat gag gat    1334
Ser Asn Leu Lys Arg Thr Ala Ser Asn Pro Lys Val Glu Asn Glu Asp
             290                 295                 300
gag gag ctc tcc tcc agc acc gag agt att gat aat tca ttc agt tcc    1382
Glu Glu Leu Ser Ser Ser Thr Glu Ser Ile Asp Asn Ser Phe Ser Ser
         305                 310                 315
cct gtt cga ctg gct cct gag aga gaa ttc atc aag tcc ctg atg gcg    1430
Pro Val Arg Leu Ala Pro Glu Arg Glu Phe Ile Lys Ser Leu Met Ala
         320                 325                 330
atc ggc aag cgg ctg gcc acg ctc ccc acc aaa gag cag aaa aca cag    1478
Ile Gly Lys Arg Leu Ala Thr Leu Pro Thr Lys Glu Gln Lys Thr Gln
335                  340                 345                 350
agg ctg atc tca gag ctc tcc ctc ctc aac cat aag ctc cct gcc cga    1526
Arg Leu Ile Ser Glu Leu Ser Leu Leu Asn His Lys Leu Pro Ala Arg
                 355                 360                 365
gtc tgg ctg ccc act gct ggc ttt gac cac cac gtg gtc cgt gta ccc    1574
Val Trp Leu Pro Thr Ala Gly Phe Asp His His Val Val Arg Val Pro
             370                 375                 380
cac aca cag gct gtt gtc ctc aac tcc aag gac aag gct ccc tac ctg    1622
His Thr Gln Ala Val Val Leu Asn Ser Lys Asp Lys Ala Pro Tyr Leu
```

```
                385                 390                 395
att tat gtg gaa gtc ctt gaa tgt gaa aac ttt gac acc acc agt gtc   1670
Ile Tyr Val Glu Val Leu Glu Cys Glu Asn Phe Asp Thr Thr Ser Val
400                 405                 410
cct gcc cgg atc ccc gag aac cga att cgg agt acg agg tcc gta gaa   1718
Pro Ala Arg Ile Pro Glu Asn Arg Ile Arg Ser Thr Arg Ser Val Glu
415                 420                 425                 430
aac ttg ccc gaa tgt ggt att acc cat gag cag cga gct ggc agc ttc   1766
Asn Leu Pro Glu Cys Gly Ile Thr His Glu Gln Arg Ala Gly Ser Phe
                435                 440                 445
agc act gtg ccc aac tat gac aac gat gat gag gcc tgg tcg gtg gat   1814
Ser Thr Val Pro Asn Tyr Asp Asn Asp Asp Glu Ala Trp Ser Val Asp
            450                 455                 460
gac ata ggc gag ctg caa gtg gag ctc ccc gaa gtg cat acc aac agc   1862
Asp Ile Gly Glu Leu Gln Val Glu Leu Pro Glu Val His Thr Asn Ser
        465                 470                 475
tgt gac aac atc tcc cag ttc tct gtg gac agc atc acc agc cag gag   1910
Cys Asp Asn Ile Ser Gln Phe Ser Val Asp Ser Ile Thr Ser Gln Glu
    480                 485                 490
agc aag gag cct gtg ttc att gca gca ggg gac atc cgc cgg cgc ctt   1958
Ser Lys Glu Pro Val Phe Ile Ala Ala Gly Asp Ile Arg Arg Arg Leu
495                 500                 505                 510
tcg gaa cag ctg gct cat acc ccg aca gcc ttc aaa cga gac cca gaa   2006
Ser Glu Gln Leu Ala His Thr Pro Thr Ala Phe Lys Arg Asp Pro Glu
                515                 520                 525
gat cct tct gca gtt gct ctc aaa gag ccc tgg cag gag aaa gta cgg   2054
Asp Pro Ser Ala Val Ala Leu Lys Glu Pro Trp Gln Glu Lys Val Arg
            530                 535                 540
cgg atc aga gag ggc tcc ccc tac ggc cat ctc ccc aat tgg cgg ctc   2102
Arg Ile Arg Glu Gly Ser Pro Tyr Gly His Leu Pro Asn Trp Arg Leu
        545                 550                 555
ctg tca gtc att gtc aag tgt ggg gat gac ctt cgg caa gag ctt ctg   2150
Leu Ser Val Ile Val Lys Cys Gly Asp Asp Leu Arg Gln Glu Leu Leu
    560                 565                 570
gcc ttt cag gtg ttg aag caa ctg cag tcc att tgg gaa cag gag cga   2198
Ala Phe Gln Val Leu Lys Gln Leu Gln Ser Ile Trp Glu Gln Glu Arg
575                 580                 585                 590
gtg ccc ctt tgg atc aag cca ata caa gat tct tgt gaa att acg act   2246
Val Pro Leu Trp Ile Lys Pro Ile Gln Asp Ser Cys Glu Ile Thr Thr
                595                 600                 605
gat agt ggc atg att gaa cca gtg gtc aat gct gtg tcc atc cat cag   2294
Asp Ser Gly Met Ile Glu Pro Val Val Asn Ala Val Ser Ile His Gln
            610                 615                 620
gtg aag aaa cag tca cag ctc tcc ttg ctc gat tac ttc cta cag gag   2342
Val Lys Lys Gln Ser Gln Leu Ser Leu Leu Asp Tyr Phe Leu Gln Glu
        625                 630                 635
cac ggc agt tac acc act gag gca ttc ctc agt gca cag cgc aat ttt   2390
His Gly Ser Tyr Thr Thr Glu Ala Phe Leu Ser Ala Gln Arg Asn Phe
    640                 645                 650
gtg caa agt tgt gct ggg tac tgc ttg gtc tgc tac ctg ctg caa gtc   2438
Val Gln Ser Cys Ala Gly Tyr Cys Leu Val Cys Tyr Leu Leu Gln Val
655                 660                 665                 670
aag gac aga cac aat ggg aat atc ctt ttg gac gca gaa ggc cac atc   2486
Lys Asp Arg His Asn Gly Asn Ile Leu Leu Asp Ala Glu Gly His Ile
                675                 680                 685
atc cac atc gac ttt ggc ttc atc ctc tcc agc tca ccc cga aat ctg   2534
Ile His Ile Asp Phe Gly Phe Ile Leu Ser Ser Ser Pro Arg Asn Leu
            690                 695                 700
ggc ttt gag acg tca gcc ttt aag ctg acc aca gag ttt gtg gat gtg   2582
Gly Phe Glu Thr Ser Ala Phe Lys Leu Thr Thr Glu Phe Val Asp Val
        705                 710                 715
atg ggc ggc ctg gat ggc gac atg ttc aac tac tat aag atg ctg atg   2630
Met Gly Gly Leu Asp Gly Asp Met Phe Asn Tyr Tyr Lys Met Leu Met
    720                 725                 730
ctg caa ggg ctg att gcc gct cgg aaa cac atg gac aag gtg gtg cag   2678
Leu Gln Gly Leu Ile Ala Ala Arg Lys His Met Asp Lys Val Val Gln
735                 740                 745                 750
atc gtg gag atc atg cag caa ggt tct cag ctt cct tgc ttc cat ggc   2726
Ile Val Glu Ile Met Gln Gln Gly Ser Gln Leu Pro Cys Phe His Gly
                755                 760                 765
tcc agc acc att cga aac ctc aaa gag agg ttc cac atg agc atg act   2774
Ser Ser Thr Ile Arg Asn Leu Lys Glu Arg Phe His Met Ser Met Thr
            770                 775                 780
gag gag cag ctg cag ctg ctg gtg gag cag atg gtg gat ggc agt atg   2822
Glu Glu Gln Leu Gln Leu Leu Val Glu Gln Met Val Asp Gly Ser Met
        785                 790                 795
cgg tct atc acc acc aaa ctc tat gac ggc ttc cag tac ctc acc aac   2870
Arg Ser Ile Thr Thr Lys Leu Tyr Asp Gly Phe Gln Tyr Leu Thr Asn
    800                 805                 810
```

```
    ggc atc atg tgacacgctc ctcagcccag gagtggtggg gggtccaggg       2919
    Gly Ile Met
            815
    caccctccct agagggccct tgtctgagaa accccaaacc aggaaacccc acctacccaa 2979
    ccatccaccc aagggaaatg gaaggcaaga aacacgaagg atcatgtggt aactgcgaga 3039
    gcttgctgag gggtgggaga gccagctgtg gggtccagac ttgttggggc ttccctgccc 3099
    ctcctggtct gtgtcagtat taccaccaga ctgactccag gactcactgc cctccagaaa 3159
    acagaggtga caaatgtgag ggacactggg gcctttcttc tccttgtagg ggtctctcag 3219
    aggttctttc cacaggccat cctcttattc cgttctgggg cccaggaagt ggggaagagt 3279
    aggttctcgg tacttaggac ttgatcctgt ggttgccact ggccatgctg ctgcccagct 3339
    ctaccccctcc cagggaccta cccctcccag ggaccgaccc ctggcccaag ctcccccttgc 3399
    tggcgggcgc tgcgtgggcc ctgcacttgc tgaggttccc catcatgggc aaggcaaggg 3459
    aattcccaca gccctccagt gtactgaggg tactggccta gccatgtgga attccctacc 3519
    ctgactcctt ccccaaaccc agggaaaaga gctctcaatt ttttattttt aattttttgtt 3579
    tgaaataaag tccttagtta gcc                                    3602
```

<210> SEQ ID NO 31
<211> LENGTH: 829
<212> TYPE: PRT
<213> ORGANISM: Homo sapiens

<400> SEQUENCE: 31

```
    Met Arg Phe Leu Glu Ala Arg Ser Leu Ala Val Ala Met Gly Asp Thr
    1               5                   10                  15
    Val Val Glu Pro Ala Pro Leu Lys Pro Thr Ser Glu Pro Thr Ser Gly
                20                  25                  30
    Pro Pro Gly Asn Asn Gly Gly Ser Leu Leu Ser Val Ile Thr Glu Gly
                35                  40                  45
    Val Gly Glu Leu Ser Val Ile Asp Pro Glu Val Ala Gln Lys Ala Cys
            50                  55                  60
    Gln Glu Val Leu Glu Lys Val Lys Leu Leu His Gly Gly Val Ala Val
    65                  70                  75                  80
    Ser Ser Arg Gly Thr Pro Leu Glu Leu Val Asn Gly Asp Gly Val Asp
                    85                  90                  95
    Ser Glu Ile Arg Cys Leu Asp Asp Pro Ala Gln Ile Arg Glu Glu
                100                 105                 110
    Glu Asp Glu Met Gly Ala Ala Val Ala Ser Gly Thr Ala Lys Gly Ala
                115                 120                 125
    Arg Arg Arg Arg Gln Asn Asn Ser Ala Lys Gln Ser Trp Leu Leu Arg
                130                 135                 140
    Leu Phe Glu Ser Lys Leu Phe Asp Ile Ser Met Ala Ile Ser Tyr Leu
    145                 150                 155                 160
    Tyr Asn Ser Lys Glu Pro Gly Val Gln Ala Tyr Ile Gly Asn Arg Leu
                    165                 170                 175
    Phe Cys Phe Arg Asn Glu Asp Val Asp Phe Tyr Leu Pro Gln Leu Leu
                180                 185                 190
    Asn Met Tyr Ile His Met Asp Glu Asp Val Gly Asp Ala Ile Lys Pro
                195                 200                 205
    Tyr Ile Val His Arg Cys Arg Gln Ser Ile Asn Phe Ser Leu Gln Cys
            210                 215                 220
    Ala Leu Leu Leu Gly Ala Tyr Ser Ser Asp Met His Ile Ser Thr Gln
    225                 230                 235                 240
    Arg His Ser Arg Gly Thr Lys Leu Arg Lys Leu Ile Leu Ser Asp Glu
                    245                 250                 255
    Leu Lys Pro Ala His Arg Lys Arg Glu Leu Pro Ser Leu Ser Pro Ala
                260                 265                 270
    Pro Asp Thr Gly Leu Ser Pro Ser Lys Arg Thr His Gln Arg Ser Lys
            275                 280                 285
    Ser Asp Ala Thr Ala Ser Ile Ser Leu Ser Ser Asn Leu Lys Arg Thr
            290                 295                 300
    Ala Ser Asn Pro Lys Val Glu Asn Glu Asp Glu Leu Ser Ser Ser
    305                 310                 315                 320
    Thr Glu Ser Ile Asp Asn Ser Phe Ser Ser Pro Val Arg Leu Ala Pro
                    325                 330                 335
    Glu Arg Glu Phe Ile Lys Ser Leu Met Ala Ile Gly Lys Arg Leu Ala
                340                 345                 350
    Thr Leu Pro Thr Lys Glu Gln Lys Thr Gln Arg Leu Ile Ser Glu Leu
            355                 360                 365
    Ser Leu Leu Asn His Lys Leu Pro Ala Arg Val Trp Leu Pro Thr Ala
        370                 375                 380
    Gly Phe Asp His His Val Val Arg Val Pro His Thr Gln Ala Val Val
    385                 390                 395                 400
    Leu Asn Ser Lys Asp Lys Ala Pro Tyr Leu Ile Tyr Val Glu Val Leu
                    405                 410                 415
    Glu Cys Glu Asn Phe Asp Thr Thr Ser Val Pro Ala Arg Ile Pro Glu
                420                 425                 430
    Asn Arg Ile Arg Ser Thr Arg Ser Val Glu Asn Leu Pro Glu Cys Gly
```

```
            435                 440                 445
     Ile Thr His Glu Gln Arg Ala Gly Ser Phe Ser Thr Val Pro Asn Tyr
     450                 455                 460
     Asp Asn Asp Asp Glu Ala Trp Ser Val Asp Ile Gly Glu Leu Gln
     465                 470                 475                 480
     Val Glu Leu Pro Glu Val His Thr Asn Ser Cys Asp Asn Ile Ser Gln
                         485                 490                 495
     Phe Ser Val Asp Ser Ile Thr Ser Gln Glu Ser Lys Glu Pro Val Phe
                     500                 505                 510
     Ile Ala Ala Gly Asp Ile Arg Arg Arg Leu Ser Gln Leu Ala His
                 515                 520                 525
     Thr Pro Thr Ala Phe Lys Arg Asp Pro Glu Asp Pro Ser Ala Val Ala
             530                 535                 540
     Leu Lys Glu Pro Trp Gln Glu Lys Val Arg Arg Ile Arg Glu Gly Ser
     545                 550                 555                 560
     Pro Tyr Gly His Leu Pro Asn Trp Arg Leu Leu Ser Val Ile Val Lys
                         565                 570                 575
     Cys Gly Asp Asp Leu Arg Gln Glu Leu Leu Ala Phe Gln Val Leu Lys
                     580                 585                 590
     Gln Leu Gln Ser Ile Trp Glu Gln Glu Arg Val Pro Leu Trp Ile Lys
                 595                 600                 605
     Pro Ile Gln Asp Ser Cys Glu Ile Thr Thr Asp Ser Gly Met Ile Glu
             610                 615                 620
     Pro Val Val Asn Ala Val Ser Ile His Gln Val Lys Lys Gln Ser Gln
     625                 630                 635                 640
     Leu Ser Leu Leu Asp Tyr Phe Leu Gln Glu His Gly Ser Tyr Thr Thr
                         645                 650                 655
     Glu Ala Phe Leu Ser Ala Gln Arg Asn Phe Val Gln Ser Cys Ala Gly
                     660                 665                 670
     Tyr Cys Leu Val Cys Tyr Leu Leu Gln Val Lys Asp Arg His Asn Gly
                 675                 680                 685
     Asn Ile Leu Leu Asp Ala Glu Gly His Ile Ile His Ile Asp Phe Gly
             690                 695                 700
     Phe Ile Leu Ser Ser Pro Arg Asn Leu Gly Phe Glu Thr Ser Ala
     705                 710                 715                 720
     Phe Lys Leu Thr Thr Glu Phe Val Asp Val Met Gly Gly Leu Asp Gly
                     725                 730                 735
     Asp Met Phe Asn Tyr Tyr Lys Met Leu Met Leu Gln Gly Leu Ile Ala
                 740                 745                 750
     Ala Arg Lys His Met Asp Lys Val Val Gln Ile Val Glu Ile Met Gln
             755                 760                 765
     Gln Gly Ser Gln Leu Pro Cys Phe His Gly Ser Ser Thr Ile Arg Asn
             770                 775                 780
     Leu Lys Glu Arg Phe His Met Ser Met Thr Glu Gln Leu Gln Leu
     785                 790                 795                 800
     Leu Val Glu Gln Met Val Asp Gly Ser Met Arg Ser Ile Thr Thr Lys
                     805                 810                 815
     Leu Tyr Asp Gly Phe Gln Tyr Leu Thr Asn Gly Ile Met
                 820                 825
```

<210> SEQ ID NO 32
<211> LENGTH: 2487
<212> TYPE: DNA
<213> ORGANISM: Homo sapiens

<400> SEQUENCE: 32

```
atgagattct tggaagctcg aagtctggct gtggccatgg gagatacagt agtggagcct    60
gcccccttga agccaacttc tgagcccact tctggcccac agggaataa tggggggtcc    120
ctgctaagtc tcatcacgga ggggtcggg gaactatcag tgattgaccc tgaggtggcc    180
cagaaggcct gccaggaggt gttggagaaa gtcaagcttt gcatggagg cgtggcagtc    240
tctagcagag gcaccccact ggagttggtc aatggggatg gtgtggacag tgagatccgt    300
tgcctagatg atccacctgc ccagatcagg gaggaggaag atgagatggg ggccgctgtg    360
gcctcaggca cagccaaagg agcaagaaga cggcggcaga acaactcagc taaacagtct    420
tggctgctga ggctgtttga gtcaaaactg tttgacatct ccatggccat ttcatacctg    480
tataactcca aggagcctgg agtacaagcc tacattggca accggctctt ctgctttcgc    540
aacgaggacg tggacttcta tctgccccag ttgcttaaca tgtacatcca catggatgag    600
gacgtgggtg atgccattaa gcctacata gtccaccgtt gccgccagag cattaacttt    660
tccctccagt gtgccctgtt gcttgggcc tattcttcag acatgcacat ttccactcaa    720
cgacactccc gtgggaccaa gctacgaag ctgatcctct cagatgagct aaagccagct    780
cacaggaaga gggagctgcc ctccttgagc ccggcccctg atacagggct gtctccctcc    840
aaaaggactc accagcgctc taagtcagat gccactgcca gcataagtct cagcagcaac    900
ctgaaacgaa cagccagcaa ccctaaagtg gagaatgagg attaggagct ctcctccagc    960
accgagagta ttgataattc attcagttcc cctgttcgac tggctcctga gagagaattc    1020
atcaagtccc tgatggcgat cggcaagcgg ctggccacgc tcccaccaa agagcagaaa    1080
acacagaggc tgatctcaga gctctccctg ctcaaccata gctcccctgc ccgagtctgg    1140
ctgcccactg ctggctttga ccaccacgtg gtccgtgtac cccacacaca ggctgttgtc    1200
ctcaactcca aggacaaggc tccctacctg atttatgtgg aagtccttga atgtgaaaac    1260
```

```
                                                -continued tttgacacca ccagtgtccc tgcccggatc cccgagaacc gaattcggag tacgaggtcc 1320
                    gtagaaaact tgcccgaatg tggtattacc catgagcagc gagctggcag cttcagcact 1380
                    gtgcccaact atgacaacga tgatgaggcc tggtcggtgg atgacatagg cgagctgcaa 1440
                    gtggagctcc ccgaagtgca taccaacagc tgtgacaaca tctcccagtt ctctgtggac 1500
                    agcatcacca gccaggagag caaggagcct gtgttcattg cagcagggga catccgccgg 1560
                    cgcctttcgg aacagctggc tcataccccg acagccttca aacgagaccc agaagatcct 1620
                    tctgcagttg ctctcaaaga gccctggcag gagaaagtga gcgggatcag agagggctcc 1680
                    ccctacggcc atctccccaa ttggcggctc ctgtcagtca ttgtcaagtg tggggatgac 1740
                    cttcggcaag agcttctggc ctttcaggtg ttgaagcaac tgcagtccat ttgggaacag 1800
                    gagcgagtgc cccttttggat caagccaata caagattctt gtgaaattac gactgatagt 1860
                    ggcatgattg aaccagtggt caatgctgtg tccatccatc aggtgaagaa acagtcacag 1920
                    ctctccttgc tcgattactt cctacaggag cacggcagtt acaccactga ggcattcctc 1980
                    agtgcacagc gcaattttgt gcaaagttgt gctgggtact gcttggtctg ctacctgctg 2040
                    caagtcaagg acagacacaa tgggaatatc cttttggacg cagaaggcca catcatccac 2100
                    atcgactttg gcttcatcct ctccagctca ccccgaaatc tgggctttga gacgtcagcc 2160
                    tttaagctga ccacagagtt tgtggatgtg atgggcggcc tggatggcga catgttcaac 2220
                    tactataaga tgctgatgct gcaaggggctg attgccgctc ggaaacacat ggacaaggtg 2280
                    gtgcagatcg tggagatcat gcagcaaggt tctcagcttc cttgcttcca tggctccagc 2340
                    accattcgaa acctcaaaga gaggttccac atgagcatga ctgaggagca gctgcagctg 2400
                    ctggtggagc agatggtgga tgcagtatg cggtctatca ccaccaaact ctatgacggc 2460
                    ttccagtacc tcaccaacgg catcatg                                      2487

<210> SEQ ID NO 33
<211> LENGTH: 3324
<212> TYPE: DNA
<213> ORGANISM: Homo sapiens
<220> FEATURE:
<221> NAME/KEY: CDS
<222> LOCATION: (115)..(2601)

<400> SEQUENCE: 33
ccggaattcc gggaaggccg gagcaagttt tgaagaagtc cctatcagat tacacttggt 60
      tgactactcc ggagcagcca ctaagaggga tgaacaggcc tgcgtggaaa ttga atg    117
                                                                  Met
                                                                   1
      aga ttc ttg gaa gct cga agt ctg gct gtg gcc atg gga gat aca gta  165
      Arg Phe Leu Glu Ala Arg Ser Leu Ala Val Ala Met Gly Asp Thr Val
                  5                  10                  15
      gtg gag cct gcc ccc ttg aag cca act tct gag ccc act tct ggc cca  213
      Val Glu Pro Ala Pro Leu Lys Pro Thr Ser Glu Pro Thr Ser Gly Pro
           20                  25                  30
      cca ggg aat aat ggg ggg tcc ctg cta agt gtc atc acg gag ggg gtc  261
      Pro Gly Asn Asn Gly Gly Ser Leu Leu Ser Val Ile Thr Glu Gly Val
       35                  40                  45
      ggg gaa cta tca gtg att gac cct gag gtg gcc cag aag gcc tgc cag  309
      Gly Glu Leu Ser Val Ile Asp Pro Glu Val Ala Gln Lys Ala Cys Gln
       50                  55                  60                  65
      gag gtg ttg gag aaa gtc aag ctt ttg cat gga ggc gtg gca gtc tct  357
      Glu Val Leu Glu Lys Val Lys Leu Leu His Gly Gly Val Ala Val Ser
                  70                  75                  80
      agc aga ggc acc cca ctg gag ttg gtc aat ggg gat ggt gtg gac agt  405
      Ser Arg Gly Thr Pro Leu Glu Leu Val Asn Gly Asp Gly Val Asp Ser
                  85                  90                  95
      gag atc cgt tgc cta gat gat cca cct gcc cag atc agg gag gag gaa  453
      Glu Ile Arg Cys Leu Asp Asp Pro Pro Ala Gln Ile Arg Glu Glu Glu
          100                 105                 110
      gat gag atg ggg gcc gct gtg gcc tca ggc aca gcc aaa gga gca aga  501
      Asp Glu Met Gly Ala Ala Val Ala Ser Gly Thr Ala Lys Gly Ala Arg
      115                 120                 125
      aga cgg cgg cag aac aac tca gct aaa cag tct tgg ctg ctg agg ctg  549
      Arg Arg Arg Gln Asn Asn Ser Ala Lys Gln Ser Trp Leu Leu Arg Leu
      130                 135                 140                 145
      ttt gag tca aaa ctg ttt gac atc tcc atg gcc att tca tac ctg tat  597
      Phe Glu Ser Lys Leu Phe Asp Ile Ser Met Ala Ile Ser Tyr Leu Tyr
                  150                 155                 160
      aac tcc aag gag cct gga gta caa gcc tac att ggc aac cgg ctc ttc  645
      Asn Ser Lys Glu Pro Gly Val Gln Ala Tyr Ile Gly Asn Arg Leu Phe
                  165                 170                 175
      tgc ttt cgc aac gag gac gtg gac ttc tat ctg ccc cag ttg ctt aac  693
      Cys Phe Arg Asn Glu Asp Val Asp Phe Tyr Leu Pro Gln Leu Leu Asn
                  180                 185                 190
      atg tac atc cac atg gat gag gac gtg ggt gat gcc att aag ccc tac  741
      Met Tyr Ile His Met Asp Glu Asp Val Gly Asp Ala Ile Lys Pro Tyr
                  195                 200                 205
      ata gtc cac cgt tgc cgc cag agc att aac ttt tcc ctc cag tgt gcc  789
      Ile Val His Arg Cys Arg Gln Ser Ile Asn Phe Ser Leu Gln Cys Ala
      210                 215                 220                 225
```

```
ctg ttg ctt ggg gcc tat tct tca gac atg cac att tcc act caa cga   837
Leu Leu Leu Gly Ala Tyr Ser Ser Asp Met His Ile Ser Thr Gln Arg
                230                 235                 240
cac tcc cgt ggg acc aag cta cgg aag ctg atc ctc tca gat gag cta   885
His Ser Arg Gly Thr Lys Leu Arg Lys Leu Ile Leu Ser Asp Glu Leu
            245                 250                 255
aag cca gct cac agg aag agg gag ctg ccc tcc ttg agc ccg gcc cct   933
Lys Pro Ala His Arg Lys Arg Glu Leu Pro Ser Leu Ser Pro Ala Pro
        260                 265                 270
gat aca ggg ctg tct ccc tcc aaa agg act cac cag cgc tct aag tca   981
Asp Thr Gly Leu Ser Pro Ser Lys Arg Thr His Gln Arg Ser Lys Ser
    275                 280                 285
gat gcc act gcc agc ata agt ctc agc agc aac ctg aaa cga aca gcc  1029
Asp Ala Thr Ala Ser Ile Ser Leu Ser Ser Asn Leu Lys Arg Thr Ala
290                 295                 300                 305
agc aac cct aaa gtg gag aat gag gat gag gag ctc tcc tcc agc acc  1077
Ser Asn Pro Lys Val Glu Asn Glu Asp Glu Glu Leu Ser Ser Ser Thr
            310                 315                 320
gag agt att gat aat tca ttc agt tcc cct gtt cga ctg gct cct gag  1125
Glu Ser Ile Asp Asn Ser Phe Ser Ser Pro Val Arg Leu Ala Pro Glu
        325                 330                 335
aga gaa ttc atc aag tcc ctg atg gcg atc ggc aag cgg ctg gcc acg  1173
Arg Glu Phe Ile Lys Ser Leu Met Ala Ile Gly Lys Arg Leu Ala Thr
    340                 345                 350
ctc ccc acc aaa gag cag aaa aca cag agg ctg atc tca gag ctc tcc  1221
Leu Pro Thr Lys Glu Gln Lys Thr Gln Arg Leu Ile Ser Glu Leu Ser
    355                 360                 365
ctg ctc aac cat aag ctc cct gcc cga gtc tgg ctg ccc act gct ggc  1269
Leu Leu Asn His Lys Leu Pro Ala Arg Val Trp Leu Pro Thr Ala Gly
370                 375                 380                 385
ttt gac cac cac gtg gtc cgt gta ccc cac aca cag gct gtt gtc ctc  1317
Phe Asp His His Val Val Arg Val Pro His Thr Gln Ala Val Val Leu
                390                 395                 400
aac tcc aag gac aag gct ccc tac ctg att tat gtg gaa gtc ctt gaa  1365
Asn Ser Lys Asp Lys Ala Pro Tyr Leu Ile Tyr Val Glu Val Leu Glu
            405                 410                 415
tgt gaa aac ttt gac acc acc agt gtc cct gcc cgg atc ccc gag aac  1413
Cys Glu Asn Phe Asp Thr Thr Ser Val Pro Ala Arg Ile Pro Glu Asn
        420                 425                 430
cga att cgg agt acg agg tcc gta gaa aac ttg ccc gaa tgt ggt att  1461
Arg Ile Arg Ser Thr Arg Ser Val Glu Asn Leu Pro Glu Cys Gly Ile
    435                 440                 445
acc cat gag cag cga gct ggc agc ttc agc act gtg ccc aac tat gac  1509
Thr His Glu Gln Arg Ala Gly Ser Phe Ser Thr Val Pro Asn Tyr Asp
450                 455                 460                 465
aac gat gat gag gcc tgg tcg gtg gat gac ata ggc gag ctg caa gtg  1557
Asn Asp Asp Glu Ala Trp Ser Val Asp Asp Ile Gly Glu Leu Gln Val
                470                 475                 480
gag ctc ccc gaa gtg cat acc aac agc tgt gac aac atc tcc cag ttc  1605
Glu Leu Pro Glu Val His Thr Asn Ser Cys Asp Asn Ile Ser Gln Phe
            485                 490                 495
tct gtg gac agc atc acc agc cag gag agc aag gag cct gtg ttc att  1653
Ser Val Asp Ser Ile Thr Ser Gln Glu Ser Lys Glu Pro Val Phe Ile
        500                 505                 510
gca gca ggg gac atc cgc cgg cgc ctt tcg gaa cag ctg gct cat acc  1701
Ala Ala Gly Asp Ile Arg Arg Arg Leu Ser Glu Gln Leu Ala His Thr
    515                 520                 525
ccg aca gcc ttc aaa cga gac cca gaa gat cct tct gca gtt gct ctc  1749
Pro Thr Ala Phe Lys Arg Asp Pro Glu Asp Pro Ser Ala Val Ala Leu
530                 535                 540                 545
aaa gag ccc tgg cag gag aaa gta cgg cgg atc aga gag ggc tcc ccc  1797
Lys Glu Pro Trp Gln Glu Lys Val Arg Arg Ile Arg Glu Gly Ser Pro
                550                 555                 560
tac ggc cat ctc ccc aat tgg cgg ctc ctg tca gtc att gtc aag tgt  1845
Tyr Gly His Leu Pro Asn Trp Arg Leu Leu Ser Val Ile Val Lys Cys
            565                 570                 575
ggg gat gac ctt cgg caa gag ctt ctg gcc ttt cag gtg ttg aag caa  1893
Gly Asp Asp Leu Arg Gln Glu Leu Leu Ala Phe Gln Val Leu Lys Gln
        580                 585                 590
ctg cag tcc att tgg gaa cag gag cga gtg ccc ctt tgg atc aag cca  1941
Leu Gln Ser Ile Trp Glu Gln Glu Arg Val Pro Leu Trp Ile Lys Pro
    595                 600                 605
ata caa gat tct tgt gaa att cga act gat agt ggc atg att gaa cca  1989
Ile Gln Asp Ser Cys Glu Ile Arg Thr Asp Ser Gly Met Ile Glu Pro
610                 615                 620                 625
gtg gtc aat gct gtg tcc atc cat cag gtg aag aaa cag tca cag ctc  2037
Val Val Asn Ala Val Ser Ile His Gln Val Lys Lys Gln Ser Gln Leu
                630                 635                 640
tcc ttg ctc gat tac ttc cta cag gag cac ggc agt tac acc act gag  2085
```

```
            Ser Leu Leu Asp Tyr Phe Leu Gln Glu His Gly Ser Tyr Thr Thr Glu
                        645                 650                 655
            gca ttc ctc agt gca cag cgc aat ttt gtg caa agt tgt gct ggg tac     2133
            Ala Phe Leu Ser Ala Gln Arg Asn Phe Val Gln Ser Cys Ala Gly Tyr
                660                     665                 670
            tgc ttg gtc tgc tac ctg ctg caa gtc aag gac aga cac aat ggg aat     2181
            Cys Leu Val Cys Tyr Leu Leu Gln Val Lys Asp Arg His Asn Gly Asn
            675                 680                 685
            atc ctt ttg gac gca gaa ggc cac atc atc cac atc gac ttt ggc ttc     2229
            Ile Leu Leu Asp Ala Glu Gly His Ile Ile His Ile Asp Phe Gly Phe
            690                 695                 700                 705
            atc ctc tcc agc tca ccc cga aat ctg ggc ttt gag acg tca gcc ttt     2277
            Ile Leu Ser Ser Ser Pro Arg Asn Leu Gly Phe Glu Thr Ser Ala Phe
                            710                 715                 720
            aag ctg acc aca gag ttt gtg gat gtg atg ggc ggc ctg gat ggc gac     2325
            Lys Leu Thr Thr Glu Phe Val Asp Val Met Gly Gly Leu Asp Gly Asp
                        725                 730                 735
            atg ttc aac tac tat aag atg ctg atg ctg caa ggg ctg att gcc gct     2373
            Met Phe Asn Tyr Tyr Lys Met Leu Met Leu Gln Gly Leu Ile Ala Ala
                    740                 745                 750
            cgg aaa cac atg gac aag gtg gtg cag atc gtg gag atc atg cag caa     2421
            Arg Lys His Met Asp Lys Val Val Gln Ile Val Glu Ile Met Gln Gln
                755                 760                 765
            ggt tct cag ctt cct tgc ttc cat ggc tcc agc acc att cga aac ctc     2469
            Gly Ser Gln Leu Pro Cys Phe His Gly Ser Ser Thr Ile Arg Asn Leu
            770                 775                 780                 785
            aaa gag agg ttc cac atg agc atg act gag gag cag ctg cag ctg ctg     2517
            Lys Glu Arg Phe His Met Ser Met Thr Glu Glu Gln Leu Gln Leu Leu
                            790                 795                 800
            gtg gag cag atg gtg gat ggc agt atg cgg tct atc acc acc aaa ctc     2565
            Val Glu Gln Met Val Asp Gly Ser Met Arg Ser Ile Thr Thr Lys Leu
                        805                 810                 815
            tat gac ggc ttc cag tac ctc acc aac ggc atc atg tgacacgctc          2611
            Tyr Asp Gly Phe Gln Tyr Leu Thr Asn Gly Ile Met
                    820                 825
            ctcagcccag gagtggtggg gggtccaggg caccctccct agagggccct tgtctgagaa   2671
            accccaaacc aggaaacccc acctacccaa ccatccaccc aagggaaatg gaaggcaaga   2731
            aacacgaagg atcatgtggt aactgcgaga gcttgctgag gggtgggaga gccagctgtg   2791
            gggtccagac ttgttggggc ttccctgccc ctcctggtct gtgtcagtat taccaccaga   2851
            ctgactccag gactcactgc cctccagaaa acagaggtga caaatgtgag ggacactggg   2911
            gcctttcttc tccttgtagg ggtctctcag aggttctttc cacaggccat cctcttattc   2971
            cgttctgggg cccaggaagt ggggaagagt aggttctcgg tacttaggac ttgatcctgt   3031
            ggttgccact ggccatgctg ctgcccagct ctaccctcc  cagggaccta ccctcccag    3091
            ggaccgaccc ctggcccaag ctccccttgc tggcgggcgc tgcgtgggcc ctgcacttgc   3151
            tgaggttccc catcatgggc aaggcaaggg aattcccaca gccctccagt gtactgaggg   3211
            tactggccta gccatgtgga attcccctacc ctgactcctt ccccaaaccc agggaaaaga  3271
            gctctcaatt ttttattttt aattttttgtt tgaaataaag tccttagtta gcc          3324

<210> SEQ ID NO 34
<211> LENGTH: 810
<212> TYPE: PRT
<213> ORGANISM: Homo sapiens

<400> SEQUENCE: 34

Met Pro Met Asp Leu Ile Leu Val Val Trp Phe Cys Val Cys Thr Ala
    1               5                   10                  15
    Arg Thr Val Val Gly Phe Gly Met Asp Pro Asp Leu Gln Met Asp Ile
                    20                  25                  30
    Val Thr Glu Leu Asp Leu Val Asn Thr Thr Leu Gly Val Ala Gln Val
                35                  40                  45
    Ser Gly Met His Asn Ala Ser Lys Ala Phe Leu Phe Gln Asp Ile Glu
            50                  55                  60
    Arg Glu Ile His Ala Ala Pro His Val Ser Glu Lys Leu Ile Gln Leu
    65                  70                  75                  80
    Phe Gln Asn Lys Ser Glu Phe Thr Ile Leu Ala Thr Val Gln Gln Lys
                            85                  90                  95
    Pro Ser Thr Ser Gly Val Ile Leu Ser Ile Arg Glu Leu His Ser
                    100                 105                 110
    Tyr Phe Glu Leu Glu Ser Ser Gly Leu Arg Asp Glu Ile Arg Tyr His
                115                 120                 125
    Tyr Ile His Asn Gly Lys Pro Arg Thr Glu Ala Leu Pro Tyr Arg Met
            130                 135                 140
    Ala Asp Gly Gln Trp His Lys Val Ala Leu Ser Val Ser Ala Ser His
    145                 150                 155                 160
    Leu Leu Leu His Val Asp Cys Asn Arg Ile Tyr Glu Arg Val Ile Asp
                            165                 170                 175
    Pro Pro Asp Thr Asn Leu Pro Pro Gly Ile Asn Leu Trp Leu Gly Gln
```

```
                    180                 185                 190
Arg Asn Gln Lys His Gly Leu Phe Lys Gly Ile Ile Gln Asp Gly Lys
                195                 200                 205
Ile Ile Phe Met Pro Asn Gly Tyr Ile Thr Gln Cys Pro Asn Leu Asn
            210                 215                 220
His Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Ser Gln Leu Glu Asn Cys His Cys Glu Lys Thr
            260                 265                 270
Cys Gln Val Ser Gly Leu Leu Tyr Arg Asp Gln Asp Ser Trp Val Asp
        275                 280                 285
Gly Asp His Cys Arg Asn Cys Thr Cys Lys Ser Gly Ala Val Glu Cys
    290                 295                 300
Arg Arg Met Ser Cys Pro Pro Leu Asn Cys Ser Pro Asp Ser Leu Pro
305                 310                 315                 320
Val His Ile Ala Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Ser
            340                 345                 350
Cys Arg Glu Cys Arg Gly Gly Val Leu Val Lys Ile Thr Glu Met Cys
        355                 360                 365
Pro Pro Leu Asn Cys Ser Glu Lys Asp His Ile Leu Pro Glu Asn Gln
    370                 375                 380
Cys Cys Arg Val Cys Arg Gly His Asn Phe Cys Ala Glu Gly Pro Lys
385                 390                 395                 400
Cys Gly Glu Asn Ser Glu Cys Lys Asn Trp Asn Thr Lys Ala Thr Cys
                405                 410                 415
Glu Cys Lys Ser Gly Tyr Ile Ser Val Gln Gly Asp Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ser Glu Gly Ile Ile Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
            580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
Pro Ser Gly Pro Ser Cys Ser Gly Asp Cys Pro His Glu Gly Gly Leu
625                 630                 635                 640
Lys His Asn Gly Gln Val Trp Thr Leu Lys Glu Asp Arg Cys Ser Val
                645                 650                 655
Cys Ser Cys Lys Asp Gly Lys Ile Phe Cys Arg Arg Thr Ala Cys Asp
            660                 665                 670
Cys Gln Asn Pro Ser Ala Asp Leu Phe Cys Cys Pro Glu Cys Asp Thr
        675                 680                 685
Arg Val Thr Ser Gln Cys Leu Asp Gln Asn Gly His Lys Leu Tyr Arg
    690                 695                 700
Ser Gly Asp Asn Trp Thr His Ser Cys Gln Gln Cys Arg Cys Leu Glu
705                 710                 715                 720
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
            740                 745                 750
Pro Cys Leu Ala Asp Asn Ile Thr Tyr Asp Ile Arg Lys Thr Cys Leu
        755                 760                 765
Asp Ser Tyr Gly Val Ser Arg Leu Ser Gly Ser Val Trp Thr Met Ala
    770                 775                 780
Gly Ser Pro Cys Thr Thr Cys Lys Cys Lys Asn Gly Arg Val Cys Cys
785                 790                 795                 800
Ser Val Asp Phe Glu Cys Leu Gln Asn Asn
                805                 810
```

<210> SEQ ID NO 35
<211> LENGTH: 2430
<212> TYPE: DNA
<213> ORGANISM: Homo sapiens

<400> SEQUENCE: 35

```
atgccgatgg atttgatttt agttgtgtgg ttctgtgtgt gcactgccag gacagtggtg   60
ggctttggga tggaccctga ccttcagatg gatatcgtca ccgagcttga cctttgtgaac  120
accacccttg gagttgctca ggtgtctgga atgcacaatg ccagcaaagc attttttattt  180
caagacatag aaagagagat ccatgcagct cctcatgtga gtgagaaatt aattcagctg   240
ttccagaaca agagtgaatt caccattttg gccactgtac agcagaagcc atccacttca   300
ggagtgatac tgtccattcg agaactggaa cacagctatt tgaactgctg gagcagtggc   360
ctgagggatg agattcggta tcactacata cacaatggga agccaaggac agaggcactt   420
ccttaccgca tggcagatgg acaatggcac aaggttgcac tgtcagttag cgcctctcat   480
ctcctgctcc atgtcgactg taacaggatt tatgagcgtg tgatagaccc tccagatacc   540
aaccttcccc caggaatcaa tttatggctt ggccagcgca accaaaagca tggcttattc   600
aaagggatca tccaagatgg gaagatcatc tttatgccga atggatatat aacacagtgt   660
ccaaatctaa atcacacttg cccaacctgc agtgatttct taagcctggt gcaaggaata   720
atggatttac aagagctttt ggccaagatg actgcaaaac taaattatgc agagacaaga   780
cttagtcaat tggaaaactg tcattgtgag aagacttgtc aagtgagtgg actgctctat   840
cgagatcaag actcttgggt agatggtgac cattgcagga actgcacttg caaaagtggt   900
gccgtggaat gccgaaggat gtcctgtccc cctctcaatt gctcccccaga ctccctccca   960
gtacacattg ctggccagtg ctgtaaggtc tgccgaccaa aatgtatcta tggaggaaaa  1020
gttcttgcag aaggccgcg gatttttaacc aagagctgtc gggaatgccg aggtggagtt  1080
ttagtaaaaa ttacagaaat gtgtcctcct ttgaactgct cagaaaagga tcacattctt  1140
cctgagaatc agtgctgccg tgtctgtaga ggtcataact tttgtgcaga aggacctaaa  1200
tgtggtgaaa actcagagtg caaaaactgg aatacaaaag ctacttgtga gtgcaagagt  1260
ggttacatct ctgtccaggg agactctgcc tactgtgaag atattgatga gtgtgcagct  1320
aagatgcatt actgtcatcg caatactgtg tgtgtcaacc ttcctgggtt atatcgctgt  1380
gactgtgtcc caggatacat tcgtgtggat gacttctctt gtacagaaca cgatgaatgt  1440
ggcagcggcc agcacaactg tgatgagaat gccatctgca ccaacactgt ccagggacac  1500
agctgcacct gcaaaccggg ctacgtgggg aacgggacca tctgcagagc ttttctgtgaa  1560
gagggctgca gatacgtgg aacgtgtgtg gctcccaaca aatgtgtctg tccatctgga  1620
ttcacaggaa gccactgcga gaaagatatt gatgaatgtt cagagggaat cattgagtgc  1680
cacaaccatt cccgctgcgt taacctgcca gggtggtacc actgtgagtg cagaagcggt  1740
ttccatgacg atgggaccta ttcactgtcc ggggagtcct gtattgacat tgatgaatgt  1800
gccttaagaa ctcacacctg ttggaacgat tctgcctgca tcaacctggc aggggggttt  1860
gactgtctct gccccctctgg gccctcctgc tctggtgact gtcctcatga aggggggctg  1920
aagcacaatg gccaggtgtg gaccttgaaa aagacaggt gttctgtctg ctcctgcaag  1980
gatggcaaga tattctgccg acggacagct tgtgattgcc agaatccaag tgctgaccta  2040
ttctgttgcc cagaatgtga caccagagtc acaagtcaat gtttagacca aaatggtcac  2100
aagctgtatc gaagtggaga caattggacc catagctgtc agcagtcg gtgtctggaa  2160
ggagaggtag attgctggcc actcacttgc cccaacttga gctgtagta tacagctatc  2220
ttagaagggg aatgttgtcc ccgctgtgtc agtgacccct gcctagctga taacatcacc  2280
tatgacatca gaaaacttg cctggacagc tatggtgtt cacggcttag tggctcagtg  2340
tggacgatgg ctggatcccc ctgcacaacc tgtaaatgca agaatggaag agtctgttgt  2400
tctgtggatt ttgagtgtct tcaaaataat                                    2430
```

<210> SEQ ID NO 36
<211> LENGTH: 2977
<212> TYPE: DNA
<213> ORGANISM: Homo sapiens
<220> FEATURE:
<221> NAME/KEY: CDS
<222> LOCATION: (103)..(2532)

<400> SEQUENCE: 36

```
tagcaagttt ggcggctcca agccaggcgc gcctcaggat ccaggctcat ttgcttccac   60
ctagcttcgg tgcccctgc taggcgggga ccctcgagag cg atg ccg atg gat      114
                                              Met Pro Met Asp
                                              1 ttg att tta gtt gtg tgg ttc tgt gtg tgc act gcc agg aca gtg gtg   162
Leu Ile Leu Val Val Trp Phe Cys Val Cys Thr Ala Arg Thr Val Val
    5                  10                  15                  20 ggc ttt ggg atg gac cct gac ctt cag atg gat atc gtc acc gag ctt   210
Gly Phe Gly Met Asp Pro Asp Leu Gln Met Asp Ile Val Thr Glu Leu
                25                  30                  35 gac ctt gtg aac acc acc ctt gga gtt gct cag gtg tct gga atg cac   258
Asp Leu Val Asn Thr Thr Leu Gly Val Ala Gln Val Ser Gly Met His
            40                  45                  50 aat gcc agc aaa gca ttt tta ttt caa gac ata gaa aga gag atc cat   306
Asn Ala Ser Lys Ala Phe Leu Phe Gln Asp Ile Glu Arg Glu Ile His
        55                  60                  65 gca gct cct cat gtg agt gag aaa tta att cag ctg ttc cag aac aag   354
```

```
            Ala Ala Pro His Val Ser Glu Lys Leu Ile Gln Leu Phe Gln Asn Lys
                    70                  75                  80
agt gaa ttc acc att ttg gcc act gta cag cag aag cca tcc act tca        402
Ser Glu Phe Thr Ile Leu Ala Thr Val Gln Gln Lys Pro Ser Thr Ser
 85                  90                  95                 100
gga gtg ata ctg tcc att cga gaa ctg gag cac agc tat ttt gaa ctg        450
Gly Val Ile Leu Ser Ile Arg Glu Leu Glu His Ser Tyr Phe Glu Leu
                   105                 110                 115
gag agc agt ggc ctg agg gat gag att cgg tat cac tac ata cac aat        498
Glu Ser Ser Gly Leu Arg Asp Glu Ile Arg Tyr His Tyr Ile His Asn
                   120                 125                 130
ggg aag cca agg aca gag gca ctt cct tac cgc atg gca gat gga caa        546
Gly Lys Pro Arg Thr Glu Ala Leu Pro Tyr Arg Met Ala Asp Gly Gln
                   135                 140                 145
tgg cac aag gtt gca ctg tca gtt agc gcc tct cat ctc ctg ctc cat        594
Trp His Lys Val Ala Leu Ser Val Ser Ala Ser His Leu Leu Leu His
                   150                 155                 160
gtc gac tgt aac agg att tat gag cgt gtg ata gac cct cca gat acc        642
Val Asp Cys Asn Arg Ile Tyr Glu Arg Val Ile Asp Pro Pro Asp Thr
165                 170                 175                 180
aac ctt ccc cca gga atc aat tta tgg ctt ggc cag cgc aac caa aag        690
Asn Leu Pro Pro Gly Ile Asn Leu Trp Leu Gly Gln Arg Asn Gln Lys
                   185                 190                 195
cat ggc tta ttc aaa ggg atc atc caa gat ggg aag atc atc ttt atg        738
His Gly Leu Phe Lys Gly Ile Ile Gln Asp Gly Lys Ile Ile Phe Met
                   200                 205                 210
ccg aat gga tat ata aca cag tgt cca aat cta aat cac act tgc cca        786
Pro Asn Gly Tyr Ile Thr Gln Cys Pro Asn Leu Asn His Thr Cys Pro
                   215                 220                 225
acc tgc agt gat ttc tta agc ctg gtg caa gga ata atg gat tta caa        834
Thr Cys Ser Asp Phe Leu Ser Leu Val Gln Gly Ile Met Asp Leu Gln
                   230                 235                 240
gag ctt ttg gcc aag atg act gca aaa cta aat tat gca gag aca aga        882
Glu Leu Leu Ala Lys Met Thr Ala Lys Leu Asn Tyr Ala Glu Thr Arg
245                 250                 255                 260
ctt agt caa ttg gaa aac tgt cat tgt gag aag act tgt caa gtg agt        930
Leu Ser Gln Leu Glu Asn Cys His Cys Glu Lys Thr Cys Gln Val Ser
                   265                 270                 275
gga ctg ctc tat cga gat caa gac tct tgg gta gat ggt gac cat tgc        978
Gly Leu Leu Tyr Arg Asp Gln Asp Ser Trp Val Asp Gly Asp His Cys
                   280                 285                 290
agg aac tgc act tgc aaa agt ggt gcc gtg gaa tgc cga agg atg tcc       1026
Arg Asn Cys Thr Cys Lys Ser Gly Ala Val Glu Cys Arg Arg Met Ser
                   295                 300                 305
tgt ccc cct ctc aat tgc tcc cca gac tcc ctc cca gta cac att gct       1074
Cys Pro Pro Leu Asn Cys Ser Pro Asp Ser Leu Pro Val His Ile Ala
                   310                 315                 320
ggc cag tgc tgt aag gtc tgc cga cca aaa tgt atc tat gga gga aaa       1122
Gly Gln Cys Cys Lys Val Cys Arg Pro Lys Cys Ile Tyr Gly Gly Lys
325                 330                 335                 340
gtt ctt gca gaa ggc cag cgg att tta acc aag agc tgt cgg gaa tgc       1170
Val Leu Ala Glu Gly Gln Arg Ile Leu Thr Lys Ser Cys Arg Glu Cys
                   345                 350                 355
cga ggt gga gtt tta gta aaa att aca gaa atg tgt cct cct ttg aac       1218
Arg Gly Gly Val Leu Val Lys Ile Thr Glu Met Cys Pro Pro Leu Asn
                   360                 365                 370
tgc tca gaa aag gat cac att ctt cct gag aat cag tgc cgt gtc           1266
Cys Ser Glu Lys Asp His Ile Leu Pro Glu Asn Gln Cys Cys Arg Val
                   375                 380                 385
tgt aga ggt cat aac ttt tgt gca gaa gga cct aaa tgt ggt gaa aac       1314
Cys Arg Gly His Asn Phe Cys Ala Glu Gly Pro Lys Cys Gly Glu Asn
390                 395                 400
tca gag tgc aaa aac tgg aat aca aaa gct act tgt gag tgc aag agt       1362
Ser Glu Cys Lys Asn Trp Asn Thr Lys Ala Thr Cys Glu Cys Lys Ser
405                 410                 415                 420
ggt tac atc tct gtc cag gga gac tct gcc tac tgt gaa gat att gat       1410
Gly Tyr Ile Ser Val Gln Gly Asp Ser Ala Tyr Cys Glu Asp Ile Asp
                   425                 430                 435
gag tgt gca gct aag atg cat tac tgt cat gcc aat act gtg tgt gtc       1458
Glu Cys Ala Ala Lys Met His Tyr Cys His Ala Asn Thr Val Cys Val
                   440                 445                 450
aac ctt cct ggg tta tat cgc tgt gac tgt gtc cca gga tac att cgt       1506
Asn Leu Pro Gly Leu Tyr Arg Cys Asp Cys Val Pro Gly Tyr Ile Arg
                   455                 460                 465
gtg gat gac ttc tct tgt aca gaa cac gat gaa tgt ggc agc ggc cag       1554
Val Asp Asp Phe Ser Cys Thr Glu His Asp Glu Cys Gly Ser Gly Gln
470                 475                 480
cac aac tgt gat gag aat gcc atc tgc acc aac act gtc cag gga cac       1602
His Asn Cys Asp Glu Asn Ala Ile Cys Thr Asn Thr Val Gln Gly His
```

```
                485                 490                 495                 500
agc tgc acc tgc aaa ccg ggc tac gtg ggg aac ggg acc atc tgc aga        1650
Ser Cys Thr Cys Lys Pro Gly Tyr Val Gly Asn Gly Thr Ile Cys Arg
                    505                 510                 515
gct ttc tgt gaa gag ggc tgc aga tac ggt gga acg tgt gtg gct ccc        1698
Ala Phe Cys Glu Glu Gly Cys Arg Tyr Gly Gly Thr Cys Val Ala Pro
        520                 525                 530
aac aaa tgt gtc tgt cca tct gga ttc aca gga agc cac tgc gag aaa        1746
Asn Lys Cys Val Cys Pro Ser Gly Phe Thr Gly Ser His Cys Glu Lys
                535                 540                 545
gat att gat gaa tgt tca gag gga atc att gag tgc cac aac cat tcc        1794
Asp Ile Asp Glu Cys Ser Glu Gly Ile Ile Glu Cys His Asn His Ser
    550                 555                 560
cgc tgc gtt aac ctg cca ggg tgg tac cac tgt gag tgc aga agc ggt        1842
Arg Cys Val Asn Leu Pro Gly Trp Tyr His Cys Glu Cys Arg Ser Gly
565                 570                 575                 580
ttc cat gac gat ggg acc tat tca ctg tcc ggg gag tcc tgt att gac        1890
Phe His Asp Asp Gly Thr Tyr Ser Leu Ser Gly Glu Ser Cys Ile Asp
                    585                 590                 595
att gat gaa tgt gcc tta aga act cac acc tgt tgg aac gat tct gcc        1938
Ile Asp Glu Cys Ala Leu Arg Thr His Thr Cys Trp Asn Asp Ser Ala
        600                 605                 610
tgc atc aac ctg gca ggg ggt ttt gac tgt ctc tgc ccc tct ggg ccc        1986
Cys Ile Asn Leu Ala Gly Gly Phe Asp Cys Leu Cys Pro Ser Gly Pro
                615                 620                 625
tcc tgc tct ggt gac tgt cct cat gaa ggg ggg ctg aag cac aat ggc        2034
Ser Cys Ser Gly Asp Cys Pro His Glu Gly Gly Leu Lys His Asn Gly
    630                 635                 640
cag gtg tgg acc ttg aaa gaa gac agg tgt tct gtc tgc tcc tgc aag        2082
Gln Val Trp Thr Leu Lys Glu Asp Arg Cys Ser Val Cys Ser Cys Lys
645                 650                 655                 660
gat ggc aag ata ttc tgc cga cgg aca gct tgt gat tgc cag aat cca        2130
Asp Gly Lys Ile Phe Cys Arg Arg Thr Ala Cys Asp Cys Gln Asn Pro
                    665                 670                 675
agt gct gac cta ttc tgt tgc cca gaa tgt gac acc aga gtc aca agt        2178
Ser Ala Asp Leu Phe Cys Cys Pro Glu Cys Asp Thr Arg Val Thr Ser
        680                 685                 690
caa tgt tta gac caa aat ggt cac aag ctg tat cga agt gga gac aat        2226
Gln Cys Leu Asp Gln Asn Gly His Lys Leu Tyr Arg Ser Gly Asp Asn
                695                 700                 705
tgg acc cat agc tgt cag cag tgt cgg tgt ctg gaa gga gag gta gat        2274
Trp Thr His Ser Cys Gln Gln Cys Arg Cys Leu Glu Gly Glu Val Asp
    710                 715                 720
tgc tgg cca ctc act tgc ccc aac ttg agc tgt gag tat aca gct atc        2322
Cys Trp Pro Leu Thr Cys Pro Asn Leu Ser Cys Glu Tyr Thr Ala Ile
725                 730                 735                 740
tta gaa ggg gaa tgt tgt ccc cgc tgt gtc agt gac ccc tgc cta gct        2370
Leu Glu Gly Glu Cys Cys Pro Arg Cys Val Ser Asp Pro Cys Leu Ala
                    745                 750                 755
gat aac atc acc tat gac atc aga aaa act tgc ctg gac agc tat ggt        2418
Asp Asn Ile Thr Tyr Asp Ile Arg Lys Thr Cys Leu Asp Ser Tyr Gly
        760                 765                 770
gtt tca cgg ctt agt ggc tca gtg tgg acg atg gct gga tct ccc tgc        2466
Val Ser Arg Leu Ser Gly Ser Val Trp Thr Met Ala Gly Ser Pro Cys
                775                 780                 785
aca acc tgt aaa tgc aag aat gga aga gtc tgc tct gtg gat ttt            2514
Thr Thr Cys Lys Cys Lys Asn Gly Arg Val Cys Ser Val Asp Phe
    790                 795                 800
gag tgt ctt caa aat aat tgaagtattt acagtggact caacgcagaa               2562
Glu Cys Leu Gln Asn Asn
805                 810
gaatggacga aatgaccatc caacgtgatt aaggatagga atcggtagtt tggtttttttt     2622
gtttgttttg ttttttttaac cacagataat tgccaaagtt tccacctgag gacggtgttt     2682
cggaggttgc cttttggacc taccactttg ctcattcttg ctaacctagt ctaggtgacc     2742
tacagtgccg tgcatttaag tcaatggttg ttaaaagaag tttcccgtgt tgtaaatcat     2802
gtttcccttta tcagatcatt tgcaaataca tttaaatgat ctcatggtaa atggttgatg    2862
tattttttgg gtttattttg tgtactaacc ataatagaag gagactcagc tccttttatt     2922
tattttgttg atttatggat caaattctaa aataaagttg cctgttgtga cttttt          2977
```

<210> SEQ ID NO 37
<211> LENGTH: 816
<212> TYPE: PRT
<213> ORGANISM: Homo sapiens

<400> SEQUENCE: 37

```
    Met Glu Ser Arg Val Leu Leu Arg Thr Phe Cys Leu Ile Phe Gly Leu
    1               5                   10                  15
```

-continued

```
Gly Ala Val Trp Gly Leu Gly Val Asp Pro Ser Leu Gln Ile Asp Val
             20                  25                  30
Leu Thr Glu Leu Glu Leu Gly Glu Ser Thr Thr Gly Val Arg Gln Val
         35                  40                  45
Pro Gly Leu His Asn Gly Thr Lys Ala Phe Leu Phe Gln Asp Thr Pro
     50                  55                  60
Arg Ser Ile Lys Ala Ser Thr Ala Thr Ala Glu Gln Phe Phe Gln Lys
 65                  70                  75                  80
Leu Arg Asn Lys His Glu Phe Thr Ile Leu Val Thr Leu Lys Gln Thr
                 85                  90                  95
His Leu Asn Ser Gly Val Ile Leu Ser Ile His His Leu Asp His Arg
            100                 105                 110
Tyr Leu Glu Leu Glu Ser Ser Gly His Arg Asn Glu Val Arg Leu His
        115                 120                 125
Tyr Arg Ser Gly Ser His Arg Pro His Thr Glu Val Phe Pro Tyr Ile
    130                 135                 140
Leu Ala Asp Asp Lys Trp His Lys Leu Ser Leu Ala Ile Ser Ala Ser
145                 150                 155                 160
His Leu Ile Leu His Ile Asp Cys Asn Lys Ile Tyr Glu Arg Val Val
                165                 170                 175
Glu Lys Pro Ser Thr Asp Leu Pro Leu Gly Thr Thr Phe Trp Leu Gly
            180                 185                 190
Gln Arg Asn Asn Ala His Gly Tyr Phe Lys Gly Ile Met Gln Asp Val
        195                 200                 205
Gln Leu Leu Val Met Pro Gln Gly Phe Ile Ala Gln Cys Pro Asp Leu
    210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                245                 250                 255
Arg Ala Glu Gln Arg Met Asn Arg Leu Asp Gln Cys Tyr Cys Glu Arg
            260                 265                 270
Thr Cys Thr Met Lys Gly Thr Thr Tyr Arg Glu Phe Glu Ser Trp Ile
        275                 280                 285
Asp Gly Cys Lys Asn Cys Thr Cys Leu Asn Gly Thr Ile Gln Cys Glu
    290                 295                 300
Thr Leu Ile Cys Pro Asn Pro Asp Cys Pro Leu Lys Ser Ala Leu Ala
305                 310                 315                 320
Tyr Val Asp Gly Lys Cys Cys Lys Glu Cys Lys Ser Ile Cys Gln Phe
                325                 330                 335
Gln Gly Arg Thr Tyr Phe Glu Gly Glu Arg Asn Thr Val Tyr Ser Ser
            340                 345                 350
Ser Gly Val Cys Val Leu Tyr Glu Cys Lys Asp Gln Thr Met Lys Leu
        355                 360                 365
Val Glu Ser Ser Gly Cys Pro Ala Leu Asp Cys Pro Glu Ser His Gln
    370                 375                 380
Ile Thr Leu Ser His Ser Cys Cys Lys Val Cys Lys Gly Tyr Asp Phe
385                 390                 395                 400
Cys Ser Glu Arg His Asn Cys Met Glu Asn Ser Ile Cys Arg Asn Leu
                405                 410                 415
Asn Asp Arg Ala Val Cys Ser Cys Arg Asp Gly Phe Arg Ala Leu Arg
            420                 425                 430
Glu Asp Asn Ala Tyr Cys Glu Asp Ile Asp Glu Cys Ala Glu Gly Arg
        435                 440                 445
His Tyr Cys Arg Glu Asn Thr Met Cys Val Asn Thr Pro Gly Ser Phe
    450                 455                 460
Met Cys Ile Cys Lys Thr Gly Tyr Ile Arg Ile Asp Asp Tyr Ser Cys
465                 470                 475                 480
Thr Glu His Asp Glu Cys Ile Thr Asn Gln His Asn Cys Asp Glu Asn
                485                 490                 495
Ala Leu Cys Phe Asn Thr Val Gly Gly His Asn Cys Val Cys Lys Pro
            500                 505                 510
Gly Tyr Thr Gly Asn Gly Thr Thr Cys Lys Ala Phe Cys Lys Asp Gly
        515                 520                 525
Cys Arg Asn Gly Gly Ala Cys Ile Ala Ala Asn Val Cys Ala Cys Pro
    530                 535                 540
Gln Gly Phe Thr Gly Pro Ser Cys Glu Thr Asp Ile Asp Glu Cys Ser
545                 550                 555                 560
Asp Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
Phe Ser Pro Ser Gly Glu Ser Cys Glu Asp Ile Asp Glu Cys Gly Thr
        595                 600                 605
Gly Arg His Ser Cys Ala Asn Asp Thr Ile Cys Phe Asn Leu Asp Gly
    610                 615                 620
Gly Tyr Asp Cys Arg Cys Pro His Gly Lys Asn Cys Thr Gly Asp Cys
625                 630                 635                 640
Ile His Asp Gly Lys Val Lys His Asn Gly Gln Ile Trp Val Leu Glu
```

```
                        645                 650                 655
    Asn Asp Arg Cys Ser Val Cys Ser Cys Gln Asn Gly Phe Val Met Cys
                660                 665                 670
    Arg Arg Met Val Cys Asp Cys Glu Asn Pro Thr Val Asp Leu Phe Cys
                675                 680                 685
    Cys Pro Glu Cys Asp Pro Arg Leu Ser Ser Gln Cys Leu His Gln Asn
                690                 695                 700
    Gly Glu Thr Leu Tyr Asn Ser Gly Asp Thr Trp Val Gln Asn Cys Gln
    705                 710                 715                 720
    Gln Cys Arg Cys Leu Gln Gly Glu Val Asp Cys Trp Pro Leu Pro Cys
                    725                 730                 735
    Pro Asp Val Glu Cys Glu Phe Ser Ile Leu Pro Glu Asn Glu Cys Cys
                740                 745                 750
    Pro Arg Cys Val Thr Asp Pro Cys Gln Ala Asp Thr Ile Arg Asn Asp
                755                 760                 765
    Ile Thr Lys Thr Cys Leu Asp Glu Met Asn Val Val Arg Phe Thr Gly
                770                 775                 780
    Ser Ser Trp Ile Lys His Gly Thr Glu Cys Thr Leu Cys Gln Cys Lys
    785                 790                 795                 800
    Asn Gly His Ile Cys Cys Ser Val Asp Pro Gln Cys Leu Gln Glu Leu
                    805                 810                 815

<210> SEQ ID NO 38
<211> LENGTH: 2448
<212> TYPE: DNA
<213> ORGANISM: Homo sapiens

<400> SEQUENCE: 38
atggagtctc gggtcttact gagaacattc tgtttgatct tcggtctcgg agcagtttgg     60
      gggcttggtg tggacccttc cctacagatt gacgtcttaa cagagttaga acttggggag    120
      tccacgaccg gagtgcgtca ggtcccgggg ctgcataatg ggacgaaagc cttctctctt    180
      caagatactc ccagaagcat aaaagcatcc actgctacag ctgaacagtt ttttcagaag    240
      ctgagaaata acatgaatt  actattttg  gtgaccctaa acagaccca  cttaaattca    300
      ggagttattc tctcaattca ccacttggat cacaggtacc ttgaactgga aagtagtggc    360
      catcggaatg aagtcagact gcattaccgc tcaggcagtc accgccctca cacagaagtg    420
      tttccttaca ttttggctga tgacaagtgg cacaagctct ccttagccat cagtgcttcc    480
      catttgattt tacacattga ctgcaataaa atttatgaaa gggtagtaga aaagccctcc    540
      acagacttgc ctctaggcac aacattttgg ctaggacaga gaaataatgc gcatgatat     600
      tttaagggta taatgcaaga tgtccaatta cttgtcatgc cccagggatt tattgctcag    660
      tgcccagatc ttaatcgcac ctgtccaact tgcaatgact ccatggact  tgtgcagaaa    720
      atcatggagc tacaggatat tttagccaaa acatcagcca agctgtctcg agctgaacag    780
      cgaatgaata gattggatca gtgctattgt gaaaggactt gcaccatgaa gggaaccacc    840
      taccgagaat ttgagtcctg datagacggc tgtaagaact gcacatgcct gaatggaacc    900
      atccagtgtg aaactctaat ctgcccaaat cctgactgcc cacttaagtc ggctcttgcg    960
      tatgtggatg gcaaatgctg taaggaatgc aaatcgatat gccaatttca aggacgaacc   1020
      tactttgaag gagaaagaaa tacagtctat tcctcttctg gagtatgtgt tctctatgag   1080
      tgcaaggacc agaccatgaa acttgttgag agttcaggct gtccagcttt ggattgtcca   1140
      gagtctcatc agataaactt gtctcacagc tgttgcaaag tttgtaaagg ttatgacttt   1200
      tgttctgaaa ggcataactg catggagaat tccatctgca gaaatctgaa tgacagggct   1260
      gtttgtagct gtcgagatgg ttttagggct cttcgagagg ataatgccta ctgtgaagac   1320
      atcgatgagt gtgctgaagg gcgccattac tgtcgtgaaa atacaatgtg tgtcaacacc   1380
      ccgggttctt ttatgtgcat ctgcaaaaact ggatacatca gaattgatga ttattcatgt   1440
      acagaacatg atgagtgtat cacaaatcag cacaactgtg atgaaaatgc tttatgcttc   1500
      aacactgttg gaggacacaa ctgtgtttgc aagccgggct atacaggaa  tggaacgaca   1560
      tgcaaagcat tttgcaaaga tggctgtagg aatggaggag cctgtattgc cgctaatgtg   1620
      tgtgcctgcc cacaaggctt cactggaccc agctgtgaaa cggacattga tgaatgctct   1680
      gatggttttg ttcaatgtga cagtcgtgct aattgcatta acctgcctgg atggtaccac   1740
      tgtgagtgca gagatggcta ccatgacaat gggatgtttt caccaagtgg agaatcgtgt   1800
      gaagatattg atgagtgtgg gaccgggagg cacagctgtg ccaatgatac catttgcttc   1860
      aatttggatg gcggatatga ttgtcgatgt cctcatggaa agaattgcac aggggactgc   1920
      atccatgatg gaaaagttaa gcacaatggt cagatttggg tgttggaaaa tgacaggtgc   1980
      tctgtgtgct catgtcagaa tggattcgtt atgtgtcgac ggatggtctg tgactgtgag   2040
      aatcccacag ttgatctttt ttgctgccct gaatgtgacc caagcttag  tagtcagtgc   2100
      ctccatcaaa atgggaaac  tttgtataac agtggtgaca cctgggtcca gaattgtcaa   2160
      cagtgccgct gcttgcaagg ggaagttgat tgtttggccc tgccttgccc agatgtggag   2220
      tgtgaattca gcattctccc agagaatgag tgctgcccgc gctgtgtcac agacccttgc   2280
      caggctgaca ccatccgcaa tgacatcacc aagacttgcc tggacgaaat gaatgtggtt   2340
      cgcttcaccg gtcctcttg  gatcaaacat ggcactgagt gtactctctg ccagtgcaag   2400
      aatggccaca tctgttgctc agtggatcca cagtgccttc aggaactg               2448

<210> SEQ ID NO 39
<211> LENGTH: 3198
<212> TYPE: DNA
<213> ORGANISM: Homo sapiens
<220> FEATURE:
<221> NAME/KEY: CDS
```

<222> LOCATION: (97)..(2544)

<400> SEQUENCE: 39

```
ttgggaggag cagtctctcc gctcgtctcc cggagctttc tccattgtct ctgcctttac    60
aacagaggga gacgatggac tgagctgatc cgcacc atg gag tct cgg gtc tta     114
                                      Met Glu Ser Arg Val Leu
                                        1               5
ctg aga aca ttc tgt ttg atc ttc ggt ctc gga gca gtt tgg ggg ctt    162
Leu Arg Thr Phe Cys Leu Ile Phe Gly Leu Gly Ala Val Trp Gly Leu
         10                  15                  20
ggt gtg gac cct tcc cta cag att gac gtc tta aca gag tta gaa ctt    210
Gly Val Asp Pro Ser Leu Gln Ile Asp Val Leu Thr Glu Leu Glu Leu
 25                  30                  35
ggg gag tcc acg acc gga gtc cgt cag gtc ccg ggg ctg cat aat ggg    258
Gly Glu Ser Thr Thr Gly Val Arg Gln Val Pro Gly Leu His Asn Gly
 40                  45                  50
acg aaa gcc ttt ctc ttt caa gat act ccc aga agc ata aaa gca tcc    306
Thr Lys Ala Phe Leu Phe Gln Asp Thr Pro Arg Ser Ile Lys Ala Ser
 55                  60                  65                  70
act gct aca gct gaa cag ttt ttt cag aag ctg aga aat aaa cat gaa    354
Thr Ala Thr Ala Glu Gln Phe Phe Gln Lys Leu Arg Asn Lys His Glu
                 75                  80                  85
ttt act att ttg gtg acc cta aaa cag acc cac tta aat tca gga gtt    402
Phe Thr Ile Leu Val Thr Leu Lys Gln Thr His Leu Asn Ser Gly Val
         90                  95                 100
att ctc tca att cac cac ttg gat cac agg tac ctg gaa ctg gaa agt    450
Ile Leu Ser Ile His His Leu Asp His Arg Tyr Leu Glu Leu Glu Ser
        105                 110                 115
agt ggc cat cgg aat gaa gtc aga ctg cat tac cgc tca ggc agt cac    498
Ser Gly His Arg Asn Glu Val Arg Leu His Tyr Arg Ser Gly Ser His
120                 125                 130
cgc cct cac aca gaa gtg ttt cct tac att ttg gct gat gac aag tgg    546
Arg Pro His Thr Glu Val Phe Pro Tyr Ile Leu Ala Asp Asp Lys Trp
135                 140                 145                 150
cac aag ctc tcc tta gcc atc agt gct tcc cat ttg att tta cac att    594
His Lys Leu Ser Leu Ala Ile Ser Ala Ser His Leu Ile Leu His Ile
                155                 160                 165
gac tgc aat aaa att tat gaa agg gta gta gaa aag ccc tcc aca gac    642
Asp Cys Asn Lys Ile Tyr Glu Arg Val Val Glu Lys Pro Ser Thr Asp
        170                 175                 180
ttg cct cta ggc aca aca ttt tgg cta gga cag aga aat aat gcg cat    690
Leu Pro Leu Gly Thr Thr Phe Trp Leu Gly Gln Arg Asn Asn Ala His
        185                 190                 195
gga tat ttt aag ggt ata atg caa gat gtc caa tta ctt gtc atg ccc    738
Gly Tyr Phe Lys Gly Ile Met Gln Asp Val Gln Leu Leu Val Met Pro
200                 205                 210
cag gga ttt att gct cag tgc cca gat ctt aat cgc acc tgt cca act    786
Gln Gly Phe Ile Ala Gln Cys Pro Asp Leu Asn Arg Thr Cys Pro Thr
215                 220                 225                 230
tgc aat gac ttc cat gga ctt gtg cag aaa atc atg gag cta cag gat    834
Cys Asn Asp Phe His Gly Leu Val Gln Lys Ile Met Glu Leu Gln Asp
                235                 240                 245
att tta gcc aaa aca tca gcc aag ctg tct cga gct gaa cag cga atg    882
Ile Leu Ala Lys Thr Ser Ala Lys Leu Ser Arg Ala Glu Gln Arg Met
        250                 255                 260
aat aga ttg gat cag tgc tat tgt gaa agg act tgc acc atc aag gga    930
Asn Arg Leu Asp Gln Cys Tyr Cys Glu Arg Thr Cys Thr Ile Lys Gly
        265                 270                 275
acc acc tac cga gaa ttt gag tcc tgg ata gac ggc tgt aag aac tgc    978
Thr Thr Tyr Arg Glu Phe Glu Ser Trp Ile Asp Gly Cys Lys Asn Cys
280                 285                 290
aca tgc ctg aat gga acc atc cag tgt gaa act cta atc tgc cca aat   1026
Thr Cys Leu Asn Gly Thr Ile Gln Cys Glu Thr Leu Ile Cys Pro Asn
295                 300                 305                 310
cct gac tgc cca ctt aag tcg gct ctt gcg tat gtg gat ggc aaa tgc   1074
Pro Asp Cys Pro Leu Lys Ser Ala Leu Ala Tyr Val Asp Gly Lys Cys
                315                 320                 325
tgt aag gaa tgc aaa tcg ata tgc caa ttt caa gga cga acc tac ttt   1122
Cys Lys Glu Cys Lys Ser Ile Cys Gln Phe Gln Gly Arg Thr Tyr Phe
        330                 335                 340
gaa gga gaa aga aat aca gtc tat tcc tct tct gga gta tgt gtt ctc   1170
Glu Gly Glu Arg Asn Thr Val Tyr Ser Ser Ser Gly Val Cys Val Leu
        345                 350                 355
tat gag tgc aag gac cag acc atg aaa ctt gtt gag tca tca ggc tgt   1218
Tyr Glu Cys Lys Asp Gln Thr Met Lys Leu Val Glu Ser Ser Gly Cys
360                 365                 370
cca gct ttg gat tgt cca gag tct cat cag ata acc ttg tct cac agc   1266
Pro Ala Leu Asp Cys Pro Glu Ser His Gln Ile Thr Leu Ser His Ser
```

-continued

```
        375                 380                 385                 390
tgt tgc aaa gtt tgt aaa ggt tat gac ttt tgt tct gaa agg cat aac    1314
Cys Cys Lys Val Cys Lys Gly Tyr Asp Phe Cys Ser Glu Arg His Asn
                    395                 400                 405
tgc atg gag aat tcc atc tgc aga aat ctg aat gac agg gct gtt tgt    1362
Cys Met Glu Asn Ser Ile Cys Arg Asn Leu Asn Asp Arg Ala Val Cys
            410                 415                 420
agc tgt cga gat ggt ttt agg gct ctt cga gag gat aat gcc tac tgt    1410
Ser Cys Arg Asp Gly Phe Arg Ala Leu Arg Glu Asp Asn Ala Tyr Cys
        425                 430                 435
gaa gac atc gat gag tgt gct gaa ggg cgc cat tac tgt cgt gaa aat    1458
Glu Asp Ile Asp Glu Cys Ala Glu Gly Arg His Tyr Cys Arg Glu Asn
    440                 445                 450
aca atg tgt gtc aac acc ccg ggt tct ttt atg tgc atc tgc aaa act    1506
Thr Met Cys Val Asn Thr Pro Gly Ser Phe Met Cys Ile Cys Lys Thr
455                 460                 465                 470
gga tac atc aga att gat gat tat tca tgt aca gaa cat gat gag tgt    1554
Gly Tyr Ile Arg Ile Asp Asp Tyr Ser Cys Thr Glu His Asp Glu Cys
                475                 480                 485
atc aca aat cag cac aac tgt gat gaa aat gct tta tgc ttc aac act    1602
Ile Thr Asn Gln His Asn Cys Asp Glu Asn Ala Leu Cys Phe Asn Thr
            490                 495                 500
gtt gga gga cac aac tgt gtt tgc aag ccg ggc tat aca ggg aat gga    1650
Val Gly Gly His Asn Cys Val Cys Lys Pro Gly Tyr Thr Gly Asn Gly
        505                 510                 515
acg aca tgc aaa gca ttt tgc aaa gat ggc tgt agg aat gga gga gcc    1698
Thr Thr Cys Lys Ala Phe Cys Lys Asp Gly Cys Arg Asn Gly Gly Ala
    520                 525                 530
tgt att gcc gct aat gtg tgt gcc tgc cca caa ggc ttc act gga ccc    1746
Cys Ile Ala Ala Asn Val Cys Ala Cys Pro Gln Gly Phe Thr Gly Pro
535                 540                 545                 550
agc tgt gaa acg gac att gat gaa tgc tct gat ggt ttt gtt caa tgt    1794
Ser Cys Glu Thr Asp Ile Asp Glu Cys Ser Asp Gly Phe Val Gln Cys
                555                 560                 565
gac agt cgt gct aat tgc att aac ctg cct gga tgg tac cac tgt gag    1842
Asp Ser Arg Ala Asn Cys Ile Asn Leu Pro Gly Trp Tyr His Cys Glu
            570                 575                 580
tgc aga gat ggc tac cat gac aat ggg atg ttt tca cca agt gga gaa    1890
Cys Arg Asp Gly Tyr His Asp Asn Gly Met Phe Ser Pro Ser Gly Glu
        585                 590                 595
tcg tgt gaa gat att gat gag tgt ggg acc ggg agg cac agc tgt gcc    1938
Ser Cys Glu Asp Ile Asp Glu Cys Gly Thr Gly Arg His Ser Cys Ala
    600                 605                 610
aat gat acc att tgc ttc aat ttg gat ggc gga tat gat tgt cga tgt    1986
Asn Asp Thr Ile Cys Phe Asn Leu Asp Gly Gly Tyr Asp Cys Arg Cys
615                 620                 625                 630
cct cat gga aag aat tgc aca ggg gac tgc atc cat gat gga aaa gtt    2034
Pro His Gly Lys Asn Cys Thr Gly Asp Cys Ile His Asp Gly Lys Val
                635                 640                 645
aag cac aat ggt cag att tgg gtg ttg gaa aat gac agg tgc tct gtg    2082
Lys His Asn Gly Gln Ile Trp Val Leu Glu Asn Asp Arg Cys Ser Val
            650                 655                 660
tgc tca tgt cag aat gga ttc gtt atg tgt cga cgg atg gtc tgt gac    2130
Cys Ser Cys Gln Asn Gly Phe Val Met Cys Arg Arg Met Val Cys Asp
        665                 670                 675
tgt gag aat ccc aca gtt gat ctt ttt tgc tgc cct gaa tgt gac cca    2178
Cys Glu Asn Pro Thr Val Asp Leu Phe Cys Cys Pro Glu Cys Asp Pro
    680                 685                 690
agg ctt agt agt cag tgc ctc cat caa aat ggg gaa act ttg tat aac    2226
Arg Leu Ser Ser Gln Cys Leu His Gln Asn Gly Glu Thr Leu Tyr Asn
695                 700                 705                 710
agt ggt gac acc tgg gtc cag aat tgt caa cag tgc cgc tgc ttg caa    2274
Ser Gly Asp Thr Trp Val Gln Asn Cys Gln Gln Cys Arg Cys Leu Gln
                715                 720                 725
ggg gaa gtt gat tgt tgg ccc ctg cct tgc cca gat gtg gag tgt gaa    2322
Gly Glu Val Asp Cys Trp Pro Leu Pro Cys Pro Asp Val Glu Cys Glu
            730                 735                 740
ttc agc att ctc cca gag aat gag tgc tgc ccg cgc tgt gtc aca gac    2370
Phe Ser Ile Leu Pro Glu Asn Glu Cys Cys Pro Arg Cys Val Thr Asp
        745                 750                 755
cct tgc cag gct gac acc atc cgc aat gac atc acc aag act tgc ctg    2418
Pro Cys Gln Ala Asp Thr Ile Arg Asn Asp Ile Thr Lys Thr Cys Leu
    760                 765                 770
gac gaa atg aat gtg gtt cgc ttc acc ggg tcc tct tgg atc aaa cat    2466
Asp Glu Met Asn Val Val Arg Phe Thr Gly Ser Ser Trp Ile Lys His
775                 780                 785                 790
ggc act gag tgt act ctc tgc cag tgc aag aat ggc cac atc tgt tgc    2514
Gly Thr Glu Cys Thr Leu Cys Gln Cys Lys Asn Gly His Ile Cys Cys
                795                 800                 805
```

```
        tca gtg gat cca cag tgc ctt cag gaa ctg tgaagttaac tgtctcatgg   2564
        Ser Val Asp Pro Gln Cys Leu Gln Glu Leu
                810                 815
        gagatttctg ttaaaagaat gttctttcat taaaagacca aaaagaagtt aaaacttaaa 2624
        ttgggtgatt tgtgggcagc taaatgcagc tttgttaata gctgagtgaa ctttcaatta 2684
        tgaaatttgt ggagcttgac aaaatcacaa aaggaaaatt actgggcaa aattagacct  2744
        caagtctgcc tctactgtgt ctcacatcac catgtagaag aatgggcgta cagtatatac 2804
        cgtgacatcc tgaacctg ataaaagcc tgagcccatt ggatctgtga aagcctctag    2864
        cttcactggt gcagaaaatt ttcctctaga tcagaatctt cagaatcagt taggttcctc 2924
        actgcaagaa ataaaatgtc aggcagtgaa tgaattatat tttcagaagt aaagcaaaga 2984
        agctataaca tgttatgtac agtacactct gaaaagaaat ctgaaacaag ttattgtaat 3044
        gataaaaata atgcacaggc atggttactt aatattttct aacaggaaaa gtcatcccta 3104
        tttccttgtt ttactgcact taatattatt tggttgaatt tgttcagtat aagctcgttc 3164
        ttgtgcaaaa ttaaataaat atttctctta cctt                             3198
```

<210> SEQ ID NO 40
<211> LENGTH: 499
<212> TYPE: PRT
<213> ORGANISM: Homo sapiens

<400> SEQUENCE: 40

```
Met Glu Leu Ser Glu Pro Val Val Glu Asn Gly Glu Val Glu Met Ala
 1               5                  10                  15
Leu Glu Glu Ser Trp Glu His Ser Lys Glu Val Ser Glu Ala Glu Pro
            20                  25                  30
Gly Gly Gly Ser Ser Gly Asp Ser Gly Pro Glu Glu Ser Gly Gln
        35                  40                  45
Glu Met Met Glu Glu Lys Glu Glu Ile Arg Lys Ser Lys Ser Val Ile
    50                  55                  60
Val Pro Ser Gly Ala Pro Lys Lys Glu His Val Asn Val Val Phe Ile
65                  70                  75                  80
Gly His Val Asp Ala Gly Lys Ser Thr Ile Gly Gly Gln Ile Met Phe
                85                  90                  95
Leu Thr Gly Met Ala Asp Lys Arg Thr Leu Glu Lys Tyr Glu Arg Glu
            100                 105                 110
Ala Glu Glu Lys Asn Arg Glu Thr Trp Tyr Leu Ser Trp Ala Leu Asp
        115                 120                 125
Thr Asn Gln Glu Glu Arg Asp Lys Gly Lys Thr Val Glu Val Gly Arg
    130                 135                 140
Ala Tyr Phe Glu Thr Glu Arg Lys His Phe Thr Ile Leu Asp Ala Pro
145                 150                 155                 160
Gly His Lys Ser Phe Val Pro Asn Met Ile Gly Gly Ala Ser Gln Ala
                165                 170                 175
Asp Leu Ala Val Leu Val Ile Ser Ala Arg Lys Gly Glu Phe Glu Thr
            180                 185                 190
Gly Phe Glu Lys Gly Gly Gln Thr Arg Glu His Ala Met Phe Gly Lys
        195                 200                 205
Thr Ala Gly Val Lys His Leu Ile Val Leu Ile Asn Lys Met Asp Asp
    210                 215                 220
Pro Thr Val Asn Trp Gly Ile Glu Arg Tyr Glu Glu Cys Lys Glu Lys
225                 230                 235                 240
Leu Val Pro Phe Leu Lys Lys Val Gly Phe Ser Pro Lys Lys Asp Ile
                245                 250                 255
His Phe Met Pro Cys Ser Gly Leu Thr Gly Ala Asn Ile Lys Glu Gln
            260                 265                 270
Ser Asp Phe Cys Pro Trp Tyr Thr Gly Leu Pro Phe Ile Pro Tyr Leu
        275                 280                 285
Asn Asn Leu Pro Asn Phe Asn Arg Ser Ile Asp Gly Pro Ile Arg Leu
    290                 295                 300
Pro Ile Val Asp Lys Tyr Lys Asp Met Gly Thr Val Val Leu Gly Lys
305                 310                 315                 320
Leu Glu Ser Gly Ser Ile Phe Lys Gly Gln Gln Leu Val Met Met Pro
                325                 330                 335
Asn Lys His Asn Val Glu Val Leu Gly Ile Leu Ser Asp Asp Thr Glu
            340                 345                 350
Thr Asp Phe Val Ala Pro Gly Glu Asn Leu Lys Ile Arg Leu Lys Gly
        355                 360                 365
Ile Glu Glu Glu Glu Ile Leu Pro Glu Phe Ile Leu Cys Asp Pro Ser
    370                 375                 380
Asn Leu Cys His Ser Gly Arg Thr Phe Asp Val Gln Ile Val Ile Ile
385                 390                 395                 400
Glu His Lys Ser Ile Ile Cys Pro Gly Tyr Asn Ala Val Leu His Ile
                405                 410                 415
His Thr Cys Ile Glu Glu Val Glu Ile Thr Ala Leu Ile Ser Leu Val
            420                 425                 430
Asp Lys Lys Ser Gly Glu Lys Ser Lys Thr Arg Pro Arg Phe Val Lys
        435                 440                 445
```

```
            Gln Asp Gln Val Cys Ile Ala Arg Leu Arg Thr Ala Gly Thr Ile Cys
                450                 455                 460
            Leu Glu Thr Phe Lys Asp Phe Pro Gln Met Gly Arg Phe Thr Leu Arg
            465                 470                 475                 480
            Asp Glu Gly Lys Thr Ile Ala Ile Gly Lys Val Leu Lys Leu Val Pro
                            485                 490                 495
            Glu Lys Asp

<210> SEQ ID NO 41
<211> LENGTH: 1497
<212> TYPE: DNA
<213> ORGANISM: Homo sapiens

<400> SEQUENCE: 41
atggaacttt cagaacctgt tgtagaaaat ggagaggtgg aaatggccct agaagaatca    60
      tgggagcaca gtaaagaagt aagtgaagcc gagcctgggg gtggttcctc gggagattca   120
      gggcccccag aagaaagtgg ccaggaaatg atggaggaaa aagaggaaat aagaaaatcc   180
      aaatctgtga tcgtaccctc aggtgcacct aagaaagaac acgtaaatgt agtattcatt   240
      ggccatgtag acgctggcaa gtcaaccatc ggaggacaga taatgttttt gactggaatg   300
      gctgacaaaa gaacactgga gaaatatgaa agagaagctg aggaaaaaaa cagagaaacc   360
      tggtatttgt cctgggcctt agatacaaat caggaggaac gagacaaggg taaaacagtc   420
      gaagtgggtc gtgcctattt tgaaacagaa aggaaacatt tcacaatttt agatgccct   480
      ggccacaaga gttttgtccc aaatatgatt ggtggtgctt ctcaagctga tttggctgtg   540
      ctggtcatct ctgccaggaa aggagagttt gaaactggat ttgaaaaggt ggacagaca   600
      agagaacatg cgatgtttgg caaaacggca ggagtaaaac atttaatagt gcttattaat   660
      aagatggatg atcccacagt aaattggggc atcgagagat atgaagaatg taaagaaaaa   720
      ctggtgccct tttttgaaaaa gtaggctttt agtccaaaaa aggacattca ctttatgccc   780
      tgctcaggac tgaccggagc aaatattaaa gagcagtcag atttctgccc ttggtacact   840
      ggattaccat ttattccgta tttgaataac ttgccaaact tcaacagatc aattgatgga   900
      ccaataagac tgccaattgt ggataagtac aaagatatgg gcactgtggt cctgggaaag   960
      ctggaatccg ggtccatttt taaaggccag cagctcgtga tgatgccaaa caagcacaat  1020
      gtagaagttc ttggaatact ttctgatgat actgaaactg attttgtagc cccaggtgaa  1080
      aacctcaaaa tcagactgaa gggaattgaa gaagaagaga ttcttccaga attcatactt  1140
      tgtgatccta gtaacctctg ccattctgga cgcacgtttg atgttcagat agtgattatt  1200
      gagcacaaat ccatcatctg cccaggttat aatgcggtgc tgcacattca tacttgtatt  1260
      gaggaagttg agataacagc gttaatctcc ttggtagaca aaaaatcagg ggaaaaaagt  1320
      aagacacgac cccgcttcgt gaaacaagat caagtatgca ttgctcgttt aaggacagca  1380
      ggaaccatct gcctcgagac gttcaaagat tttcctcaga tgggtcgttt tactttaaga  1440
      gatgagggta agaccattgc aattggaaaa gttctgaaat tggtcccaga gaaggac    1497

<210> SEQ ID NO 42
<211> LENGTH: 2057
<212> TYPE: DNA
<213> ORGANISM: Homo sapiens
<220> FEATURE:
<221> NAME/KEY: CDS
<222> LOCATION: (144)..(1640)

<400> SEQUENCE: 42
tcccggccgg ctccggcagc aacgatgaag cctgcaccgg cgcgggatac cctcaaggta    60
      aaaggatggg acgggggggca cctgtggaac cttcccgaga ggaaccgtta gtgtcgcttg   120
      aaggttccaa ttcagccgtt acc atg gaa ctt tca gaa cct gtt gta gaa aat   173
                            Met Glu Leu Ser Glu Pro Val Val Glu Asn
                              1               5                  10 gga gag gtg gaa atg gcc cta gaa gaa tca tgg gag cac agt aaa gaa     221
      Gly Glu Val Glu Met Ala Leu Glu Glu Ser Trp Glu His Ser Lys Glu
                     15                  20                  25 gta agt gaa gcc gag cct ggg ggt ggt tcc tcg gga gat tca ggg ccc     269
      Val Ser Glu Ala Glu Pro Gly Gly Gly Ser Ser Gly Asp Ser Gly Pro
             30                  35                  40 cca gaa gaa agt ggc cag gaa atg atg gag gaa aaa gag gaa ata aga     317
      Pro Glu Glu Ser Gly Gln Glu Met Met Glu Glu Lys Glu Glu Ile Arg
         45                  50                  55 aaa tcc aaa tct gtg atc gta ccc tca ggt gca cct aag aaa gaa cac     365
      Lys Ser Lys Ser Val Ile Val Pro Ser Gly Ala Pro Lys Lys Glu His
     60                  65                  70 gta aat gta gta ttc att ggc cat gta gac gct ggc aag tca acc atc     413
      Val Asn Val Val Phe Ile Gly His Val Asp Ala Gly Lys Ser Thr Ile
     75                  80                  85                  90 gga gga cag ata atg ttt ttg act gga atg gct gac aaa aga aca ctg     461
      Gly Gly Gln Ile Met Phe Leu Thr Gly Met Ala Asp Lys Arg Thr Leu
                     95                 100                 105 gag aaa tat gaa aga gaa gct gag gaa aaa aac aga gaa acc tgg tat     509
      Glu Lys Tyr Glu Arg Glu Ala Glu Glu Lys Asn Arg Glu Thr Trp Tyr
                110                 115                 120
```

```
ttg tcc tgg gcc tta gat aca aat cag gag gaa cga gac aag ggt aaa    557
Leu Ser Trp Ala Leu Asp Thr Asn Gln Glu Glu Arg Asp Lys Gly Lys
        125                 130                 135
aca gtc gaa gtg ggt cgt gcc tat ttt gaa aca gaa agg aaa cat ttc    605
Thr Val Glu Val Gly Arg Ala Tyr Phe Glu Thr Glu Arg Lys His Phe
140                 145                 150
aca att tta gat gcc cct ggc cac aag agt ttt gtc cca aat atg att    653
Thr Ile Leu Asp Ala Pro Gly His Lys Ser Phe Val Pro Asn Met Ile
155                 160                 165                 170
ggt ggt gct tct caa gct gat ttg gct gtg ctg gtc atc tct gcc agg    701
Gly Gly Ala Ser Gln Ala Asp Leu Ala Val Leu Val Ile Ser Ala Arg
                175                 180                 185
aaa gga gag ttt gaa act gga ttt gaa aaa ggt gga cag aca aga gaa    749
Lys Gly Glu Phe Glu Thr Gly Phe Glu Lys Gly Gly Gln Thr Arg Glu
        190                 195                 200
cat gcg atg ttt ggc aaa acg gca gga gta aaa cat tta ata gtg ctt    797
His Ala Met Phe Gly Lys Thr Ala Gly Val Lys His Leu Ile Val Leu
            205                 210                 215
att aat aag atg gat gat ccc aca gta aat tgg ggc atc gag aga tat    845
Ile Asn Lys Met Asp Asp Pro Thr Val Asn Trp Gly Ile Glu Arg Tyr
220                 225                 230
gaa gaa tgt aaa gaa aaa ctg gtg ccc ttt ttg aaa aaa gta ggc ttt    893
Glu Glu Cys Lys Glu Lys Leu Val Pro Phe Leu Lys Lys Val Gly Phe
235                 240                 245                 250
agt cca aaa aag gac att cac ttt atg ccc tgc tca gga ctg acc gga    941
Ser Pro Lys Lys Asp Ile His Phe Met Pro Cys Ser Gly Leu Thr Gly
                255                 260                 265
gca aat att aaa gag cag tca gat ttc tgc cct tgg tac act gga tta    989
Ala Asn Ile Lys Glu Gln Ser Asp Phe Cys Pro Trp Tyr Thr Gly Leu
        270                 275                 280
cca ttt att ccg tat ttg aat aac ttg cca aac ttc aac aga tca att   1037
Pro Phe Ile Pro Tyr Leu Asn Asn Leu Pro Asn Phe Asn Arg Ser Ile
            285                 290                 295
gat gga cca ata aga ctg cca att gtg gat aag tac aaa gat atg ggc   1085
Asp Gly Pro Ile Arg Leu Pro Ile Val Asp Lys Tyr Lys Asp Met Gly
300                 305                 310
act gtg gtc ctg gga aag ctg gaa tcc ggg tcc att ttt aaa ggc cag   1133
Thr Val Val Leu Gly Lys Leu Glu Ser Gly Ser Ile Phe Lys Gly Gln
315                 320                 325                 330
cag ctc gtg atg atg cca aac aag cac aat gta gaa gtt ctt gga ata   1181
Gln Leu Val Met Met Pro Asn Lys His Asn Val Glu Val Leu Gly Ile
                335                 340                 345
ctt tct gat gat act gaa act gat ttt gta gcc cca ggt gaa aac ctc   1229
Leu Ser Asp Asp Thr Glu Thr Asp Phe Val Ala Pro Gly Glu Asn Leu
        350                 355                 360
aaa atc aga ctg aag gga att gaa gaa gaa gag att ctt cca gaa ttc   1277
Lys Ile Arg Leu Lys Gly Ile Glu Glu Glu Glu Ile Leu Pro Glu Phe
            365                 370                 375
ata ctt tgt gat cct agt aac ctc tgc cat tct gga cgc acg ttt gat   1325
Ile Leu Cys Asp Pro Ser Asn Leu Cys His Ser Gly Arg Thr Phe Asp
380                 385                 390
gtt cag ata gtg att att gag cac aaa tcc atc atc tgc cca ggt tat   1373
Val Gln Ile Val Ile Glu His Lys Ser Ile Ile Cys Pro Gly Tyr
395                 400                 405                 410
aat gcg gtg ctg cac att cat act tgt att gag gaa gtt gag ata aca   1421
Asn Ala Val Leu His Ile His Thr Cys Ile Glu Glu Val Glu Ile Thr
                415                 420                 425
gcg tta atc tcc ttg gta gac aaa aaa tca ggg gaa aaa agt aag aca   1469
Ala Leu Ile Ser Leu Val Asp Lys Lys Ser Gly Glu Lys Ser Lys Thr
        430                 435                 440
cga ccc cgc ttc gtg aaa caa gat caa gta tgc att gct cgt tta agg   1517
Arg Pro Arg Phe Val Lys Gln Asp Gln Val Cys Ile Ala Arg Leu Arg
            445                 450                 455
aca gca gga acc atc tgc ctc gag acg ttc aaa gat ttt cct cag atg   1565
Thr Ala Gly Thr Ile Cys Leu Glu Thr Phe Lys Asp Phe Pro Gln Met
460                 465                 470
ggt cgt ttt act tta aga gat gag ggt aag acc att gca att gga aaa   1613
Gly Arg Phe Thr Leu Arg Asp Glu Gly Lys Thr Ile Ala Ile Gly Lys
475                 480                 485                 490
gtt ctg aaa ttg gtc cca gag aag gac taagcaattt tcttgatgcc         1660
Val Leu Lys Leu Val Pro Glu Lys Asp
                495
tctgcaagat actgtgagga gaattgacag caaaagttca ccacctactc ttatttactg 1720
cccattgatt gacttttctt catattttgc aaagagaaat ttcacagcaa aaattcatgt 1780
tttgtcagct ttctcatgtt gagatctgtt atgtcactga tgaatttacc ctcaagtttc 1840
cttcctctgt accactctgc ttccttggac aatatcagta atagctttgt aagtgatgtg 1900
gacgtaattg cctacagtaa taaaaaaata atgtacttta attttcatt ttcttttagg 1960
atatttagac cacccttgtt ccacgcaaac cagagtgtgt cagtgtttgt gtgtgtgtta 2020
aaatgataac taacatgtga ataaaatact ccatttg                          2057
```

```
<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Primer P1

<400> SEQUENCE: 43
acaccaatcc agtagccagg cttg                                          24

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Primer P2

<400> SEQUENCE: 44
cactcgagaa tctgtgagac ctacatacat gacg                               34

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: consensus
      sequence
<223> OTHER INFORMATION: all "Xaa" amino acids are unidentified

<400> SEQUENCE: 45

Cys Xaa Glu Cys Gly Lys Ala Phe Xaa Gln Lys Ser Xaa Leu Xaa Xaa
     1               5                  10                  15
    His Gln Arg Xaa His
                 20

<210> SEQ ID NO 46
<211> LENGTH: 7
<212> TYPE: PRT
<213> ORGANISM: Bovine sp.

<400> SEQUENCE: 46

Val Leu Asn Ile Ser Leu Trp
     1               5

<210> SEQ ID NO 47
<211> LENGTH: 17
<212> TYPE: PRT
<213> ORGANISM: Bovine sp.

<400> SEQUENCE: 47

Thr Leu Met Glu Leu Leu Asn Gln Met Asp Gly Phe Asp Thr Leu His
     1               5                  10                  15
    Arg

<210> SEQ ID NO 48
<211> LENGTH: 14
<212> TYPE: PRT
<213> ORGANISM: Bovine sp.
<220> FEATURE:
<223> OTHER INFORMATION: all "Xaa" amino acids are unidentified

<400> SEQUENCE: 48

Ala Val Ser Asp Phe Val Val Ser Glu Tyr Xaa Met Xaa Ala
     1               5                  10
```

```
<210> SEQ ID NO 49
<211> LENGTH: 9
<212> TYPE: PRT
<213> ORGANISM: Bovine sp.
<220> FEATURE:
<223> OTHER INFORMATION: all "Xaa" amino acids are unidentified

<400> SEQUENCE: 49

Glu Val Asp Pro Leu Val Tyr Asn Xaa
      1               5

<210> SEQ ID NO 50
<211> LENGTH: 11
<212> TYPE: PRT
<213> ORGANISM: Bovine sp.

<400> SEQUENCE: 50

His Gly Glu Ile Asp Tyr Glu Ala Ile Val Lys
      1               5                  10

<210> SEQ ID NO 51
<211> LENGTH: 25
<212> TYPE: PRT
<213> ORGANISM: Bovine sp.
<220> FEATURE:
<223> OTHER INFORMATION: all "Xaa" amino acids are unidentified

<400> SEQUENCE: 51

Leu Ser Xaa Gly Phe Asn Gly Ala Asp Leu Arg Asn Val Xaa Thr Glu
      1               5                  10                  15
     Ala Gly Met Phe Ala Ile Xaa Ala Asp
                 20                  25

<210> SEQ ID NO 52
<211> LENGTH: 21
<212> TYPE: PRT
<213> ORGANISM: Bovine sp.
<220> FEATURE:
<223> OTHER INFORMATION: all "Xaa" amino acids are unidentified

<400> SEQUENCE: 52

Met Ile Met Ala Thr Asn Arg Pro Asp Thr Leu Asp Pro Ala Leu Leu
      1               5                  10                  15
     Arg Pro Gly Xaa Leu
                 20

<210> SEQ ID NO 53
<211> LENGTH: 16
<212> TYPE: PRT
<213> ORGANISM: Bovine sp.

<400> SEQUENCE: 53

Ile His Ile Asp Leu Pro Asn Glu Gln Ala Arg Leu Asp Ile Leu Lys
      1               5                  10                  15

<210> SEQ ID NO 54
<211> LENGTH: 11
<212> TYPE: PRT
<213> ORGANISM: Bovine sp.

<400> SEQUENCE: 54

Ala Thr Asn Gly Pro Arg Tyr Val Val Val Gly
      1               5                  10

<210> SEQ ID NO 55
<211> LENGTH: 7
<212> TYPE: PRT
```

```
<213> ORGANISM: Bovine sp.

<400> SEQUENCE: 55

Glu Ile Asp Gly Arg Leu Lys
          1               5

<210> SEQ ID NO 56
<211> LENGTH: 14
<212> TYPE: PRT
<213> ORGANISM: Bovine sp.

<400> SEQUENCE: 56

Ala Leu Gln Ser Val Gly Gln Ile Val Gly Glu Val Leu Lys
          1               5                  10

<210> SEQ ID NO 57
<211> LENGTH: 8
<212> TYPE: PRT
<213> ORGANISM: Bovine sp.

<400> SEQUENCE: 57

Ile Leu Ala Gly Pro Ile Thr Lys
          1               5

<210> SEQ ID NO 58
<211> LENGTH: 16
<212> TYPE: PRT
<213> ORGANISM: Bovine sp.
<220> FEATURE:
<223> OTHER INFORMATION: all "Xaa" amino acids are unidentified

<400> SEQUENCE: 58

Xaa Xaa Val Ile Glu Leu Pro Leu Thr Asn Pro Glu Leu Phe Gln Gly
          1               5                  10                  15

<210> SEQ ID NO 59
<211> LENGTH: 9
<212> TYPE: PRT
<213> ORGANISM: Bovine sp.

<400> SEQUENCE: 59

Val Val Ser Ser Ser Leu Val Asp Lys
          1               5

<210> SEQ ID NO 60
<211> LENGTH: 7
<212> TYPE: PRT
<213> ORGANISM: Bovine sp.

<400> SEQUENCE: 60

Ala Leu Gln Asp Tyr Arg Lys
          1               5

<210> SEQ ID NO 61
<211> LENGTH: 7
<212> TYPE: PRT
<213> ORGANISM: Bovine sp.

<400> SEQUENCE: 61

Glu His Arg Glu Gln Leu Lys
          1               5

<210> SEQ ID NO 62
<211> LENGTH: 12
<212> TYPE: PRT
```

<213> ORGANISM: Bovine sp.

<400> SEQUENCE: 62

```
Lys Leu Glu Ser Lys Leu Asp Tyr Lys Pro Val Arg
 1               5                  10
```

<210> SEQ ID NO 63
<211> LENGTH: 5
<212> TYPE: PRT
<213> ORGANISM: Bovine sp.

<400> SEQUENCE: 63

```
Leu Val Pro Thr Arg
 1               5
```

<210> SEQ ID NO 64
<211> LENGTH: 11
<212> TYPE: PRT
<213> ORGANISM: Bovine sp.

<400> SEQUENCE: 64

```
Ala Lys Glu Glu Glu Ile Glu Ala Gln Ile Lys
 1               5                  10
```

<210> SEQ ID NO 65
<211> LENGTH: 10
<212> TYPE: PRT
<213> ORGANISM: Bovine sp.

<400> SEQUENCE: 65

```
Ala Asn Tyr Glu Val Leu Glu Ser Gln Lys
 1               5                  10
```

<210> SEQ ID NO 66
<211> LENGTH: 11
<212> TYPE: PRT
<213> ORGANISM: Bovine sp.

<400> SEQUENCE: 66

```
Val Glu Asp Ala Leu His Gln Leu His Ala Arg
 1               5                  10
```

<210> SEQ ID NO 67
<211> LENGTH: 8
<212> TYPE: PRT
<213> ORGANISM: Bovine sp.

<400> SEQUENCE: 67

```
Asp Val Asp Leu Tyr Gln Val Arg
 1               5
```

<210> SEQ ID NO 68
<211> LENGTH: 13
<212> TYPE: PRT
<213> ORGANISM: Bovine sp.

<400> SEQUENCE: 68

```
Gln Ser Gln Gly Leu Ser Pro Ala Gln Ala Phe Ala Lys
 1               5                  10
```

<210> SEQ ID NO 69
<211> LENGTH: 21
<212> TYPE: PRT
<213> ORGANISM: Bovine sp.

-continued

```
<400> SEQUENCE: 69

Ala Gly Ser Gln Ser Gly Gly Ser Pro Glu Ala Ser Gly Val Thr Val
      1               5                  10                  15
     Ser Asp Val Gln Glu
                 20

<210> SEQ ID NO 70
<211> LENGTH: 12
<212> TYPE: PRT
<213> ORGANISM: Bovine sp.
<220> FEATURE:
<223> OTHER INFORMATION: all "Xaa" amino acids are unidentified

<400> SEQUENCE: 70

Gly Leu Leu Gly Xaa Asn Ile Ile Pro Leu Gln Arg
      1               5                  10

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Primer P1

<400> SEQUENCE: 71
ttgaagaatg atgcattagg aaccac                                  26

<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: Primer P2

<400> SEQUENCE: 72
cactcgagtg gctggatttc aatttctcca gtag                         34

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Primer P3

<400> SEQUENCE: 73
gtcgagctag ccatctcctc ttcg                                    24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Primer P4

<400> SEQUENCE: 74
catgggcgac aggttccgag acc                                     23

<210> SEQ ID NO 75
<211> LENGTH: 9
<212> TYPE: PRT
<213> ORGANISM: Homo sapiens

<400> SEQUENCE: 75

Lys Gly Ile Pro Ser Phe Trp Leu Thr
      1               5
```

```
<210> SEQ ID NO 76
<211> LENGTH: 9
<212> TYPE: PRT
<213> ORGANISM: Saccharomyces sp.

<400> SEQUENCE: 76

Lys Gly Ile Pro Glu Phe Trp Leu Thr
     1               5

<210> SEQ ID NO 77
<211> LENGTH: 10
<212> TYPE: PRT
<213> ORGANISM: Homo sapiens

<400> SEQUENCE: 77

Asp Ser Phe Phe Asn Phe Phe Ala Pro Pro
     1               5                  10

<210> SEQ ID NO 78
<211> LENGTH: 9
<212> TYPE: PRT
<213> ORGANISM: Saccharomyces sp.

<400> SEQUENCE: 78

Glu Ser Phe Phe Asn Phe Phe Ser Pro
     1               5

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: consensus
      sequence
<223> OTHER INFORMATION: all "Xaa" amino acids are unidentified

<400> SEQUENCE: 79

Glu Xaa Xaa Lys Glu Xaa Pro Glu Val Lys Xaa Glu Glu Lys
     1               5                  10

<210> SEQ ID NO 80
<211> LENGTH: 5
<212> TYPE: PRT
<213> ORGANISM: HIV-1

<400> SEQUENCE: 80

Gly Arg Lys Lys Arg
     1               5

<210> SEQ ID NO 81
<211> LENGTH: 5
<212> TYPE: PRT
<213> ORGANISM: Homo sapiens

<400> SEQUENCE: 81

Lys Lys Lys Arg Lys
     1               5

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: A1 Primer

<400> SEQUENCE: 82
```

```
        cctaaaaagt gtctaagtgc cagtt                                        25

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: A2 Primer

<400> SEQUENCE: 83
tcagtgaaag ggaaggtaga acac                                         24

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: P1 Primer

<400> SEQUENCE: 84
taatgaattt cattttagga ggtcgg                                       26

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: P2 Primer

<400> SEQUENCE: 85
atcttttggg aaagtaagat gagcc                                        25

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: C1 Primer

<400> SEQUENCE: 86
ggagactcac ctgctaatgt t                                            21

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: C4 Primer

<400> SEQUENCE: 87
ctcaaaagca gtctcttggc                                              20

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Primer A

<400> SEQUENCE: 88
atgggagata cagtagtgga gc                                           22

<210> SEQ ID NO 89
<211> LENGTH: 21
<212> TYPE: DNA
```

```
<213> ORGANISM: Artificial Sequence
<220> FEATURE:
<223> OTHER INFORMATION: Description of Artificial Sequence: Primer B

<400> SEQUENCE: 89
tcacatgatg ccgttggtga g                                         21

<210> SEQ ID NO 90
<211> LENGTH: 51
<212> TYPE: DNA
<213> ORGANISM: Homo sapiens

<400> SEQUENCE: 90
tggatcaagc caatacaaga ttcttgtgaa attacgactg atagtggcat g         51

<210> SEQ ID NO 91
<211> LENGTH: 117
<212> TYPE: DNA
<213> ORGANISM: Homo sapiens

<400> SEQUENCE: 91
tccatttggg aacaggagcg agtgcccctt tggatcaagc catacaagat tcttgtgatt 60
    tcggctgata gtggcatgat tgaaccagtg gtcaatgctg tgtccatcca tcaggtg    117

<210> SEQ ID NO 92
<211> LENGTH: 31
<212> TYPE: DNA
<213> ORGANISM: Artificial Sequence
<220> FEATURE:
<223> OTHER INFORMATION: Description of Artificial Sequence: Primer C1

<400> SEQUENCE: 92
ctcagatcta tgggagatac agtagtggag c                               31

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Primer C2

<400> SEQUENCE: 93
tcgagatctt cacatgatgc cgttggtgag                                 30

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: P1 Primer

<400> SEQUENCE: 94
gatttgtgct caataatcac tatctgaa                                   28

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: P2 Primer

<400> SEQUENCE: 95
ggttactagg atcacaaagt atgaattctg gaa                             33
```

METHOD FOR DETECTING EXPRESSION OF HUMAN SKELETAL MUSCLE-SPECIFIC UNBIQUITIN-CONJUGATED ENZYME

CROSS-REFERENCE TO RELATED APPLICATIONS

This Application is a Divisional of U.S. application Ser. No. 09/273,565, filed Mar. 22, 1999 (now U.S. Pat. No. 6,166,190); which in turn is a Divisional of U.S. application Ser. No. 09/055,699, filed Apr. 7, 1998 (now U.S. Pat. No. 6,005,088); which in turn is a Divisional of U.S. application Ser. No. 08/820,170, filed Mar. 19, 1997 (now U.S. Pat. No. 5,831,058).

TECHNICAL FIELD

The present invention relates to a gene useful as an indicator in the prophylaxis, diagnosis and treatment of diseases in humans. More particularly, it relates to a novel human gene analogous to rat, mouse, yeast, nematode and known human genes, among others, and utilizable, after cDNA analysis thereof, chromosome mapping of cDNA and function analysis of cDNA, in gene diagnosis using said gene and in developing a novel therapeutic method.

BACKGROUND ART

The genetic information of a living thing has been accumulated as sequences (DNA) of four bases, namely A, C, G and T, which exist in cell nuclei. Said genetic information has been preserved for line preservation and ontogeny of each individual living thing.

In the case of human being, the number of said bases is said to be about 3 billion ($3 \times 10^9$) and supposedly there are 50 to 100 thousand genes therein. Such genetic information serves to maintain biological phenomena in that regulatory proteins, structural proteins and enzymes are produced via such route that mRNA is transcribed from a gene (DNA) and then trans lated into a protein. Abnormalities in said route from gene to protein translation are considered to be causative of abnormalities of life supporting systems, for example in cell proliferation and differentiation, hence causative of various diseases.

As a result of gene analyses so far made, a number of genes which may be expected to serve as useful materials in drug development, have been found, for example genes for various receptors such as insulin receptor and LDL receptor, genes involved in cell proliferation and differentiation and genes for metabolic enzymes such as proteases, ATPase and superoxide dismutases.

However, analysis of human genes and studies of the functions of the genes analyzed and of the relations between the genes analyzed and various diseases have been just begun and many points remain unknown. Further analysis of novel genes, analysis of the functions thereof, studies of the relations between the genes analyzed and diseases, and studies for applying the genes analyzed to gene diagnosis or for medicinal purposes, for instance, are therefore desired in the relevant art.

If such a novel human gene as mentioned above can be provided, it will be possible to analyze the level of expression thereof in each cell and the structure and function thereof and, through expression product analysis and other studies, it may become possible to reveal the pathogenesis of a disease associated therewith, for example a genopathy or cancer, or diagnose and treat said disease, for instance. It is an object of the present invention to provide such a novel human gene.

For attaining the above object, the present inventors made intensive investigations and obtained the findings mentioned below. Based thereon, the present invention has now been completed.

DISCLOSURE OF INVENTION

Thus, the present inventors synthesized cDNAs based on mRNAs extracted from various tissues, inclusive of human fetal brain, adult blood vessels and placenta, constructed libraries by inserting them into vectors, allowing colonies of *Escherichia coli* transformed with said libraries to form on agar medium, picked up colonies at random and transferred to 96-well micro plates and registered a large number of human gene-containing *E. coli* clones.

Each clone thus registered was cultivated on a small size, DNA was extracted and purified, the four base-specifically terminating extension reactions were carried out by the dideoxy chain terminator method using the cDNA extracted as a template, and the base sequence of the gene was determined over about 400 bases from the 5' terminus thereof using an automatic DNA sequencer. Based on the thus-obtained base sequence information, a novel family gene analogous to known genes of animal and plant species such as bacteria, yeasts, nematodes, mice and humans was searched for.

The method of the above-mentioned cDNA analysis is detailedly described in the literature by Fujiwara, one of the present inventors [Fujiwara, Tsutomu, Saibo Kogaku (Cell Engineering), 14, 645–654 (1995)].

Among this group, there are novel receptors, DNA binding domain-containing transcription regulating factors, signal transmission system factors, metabolic enzymes and so forth. Based on the homology of the novel gene of the present invention as obtained by gene analysis to the genes analogous thereto, the product of the gene, hence the function of the protein, can approximately be estimated by analogy. Furthermore, such functions as enzyme activity and binding ability can be investigated by inserting the candidate gene into an expression vector to give a recombinant.

According to the present invention, there are provided a novel human gene characterized by containing a nucleotide sequence coding for an amino acid sequence defined by SEQ ID NO:1, :4, :7, :10, :13, :16, :19, :22, :25, :28, :31, :34, :37 or 40, a human gene characterized by containing the nucleotide sequence defined by SEQ ID NO:2, :5, :8, :11, :14, :17, :20, :23, :26, :29, :32, :35, :38 or :41, respectively coding for the amino acid sequence mentioned above, and a novel human gene characterized by the nucleotide sequence defined by SEQ ID NO:3, :6, :9, :12, :15, :18, :21, :24, :27, :30, :33, :36, :39 or :42.

The symbols used herein for indicating amino acids, peptides, nucleotides, nucleotide sequences and so on are those recommended by IUPAC and IUB or in "Guide-line for drafting specifications etc. including nucleotide sequences or amino acid sequences" (edited by the Japanese Patent Office), or those in conventional use in the relevant field of art.

As specific examples of such gene of the present invention, there may be mentioned genes deducible from the DNA sequences of the clones designated as "GEN-501D08", "GEN-080G01", "GEN-025F07", "GEN-076C09", "GEN-331G07", "GEN-163D09", "GEN-078D05TA13", "GEN-423A12", "GEN-092E10", "GEN-428B12", "GEN-073E07", "GEN-093E05", and "GEN-077A09" shown later herein in Examples 1 to 11. The respective nucleotide sequences are as shown in the sequence listing.

These clones have an open reading frame comprising nucleotides (nucleic acid) respectively coding for the amino acids shown in the sequence listing. Their molecular weights were calculated at the values shown later herein in the respective examples. Hereinafter, these human genes of the present invention are sometimes referred to as the designation used in Examples 1 to 11.

In the following, the human gene of the present invention is described in further detail.

As mentioned above, each human gene of the present invention is analogous to rat, mouse, yeast, nematode and known human genes, among others, and can be utilized in human gene analysis based on the information about the genes analogous thereto and in studying the function of the gene analyzed and the relation between the gene analyzed and a disease. It is possible to use said gene in gene diagnosis of the disease associated therewith and in exploitation studies of said gene for medicinal purposes.

The gene of the present invention is represented in terms of a single-stranded DNA sequence, as shown under SEQ ID NO:2. It is to be noted, however, that the present invention also includes a DNA sequence complementary to such a single-stranded DNA sequence and a component comprising both. The sequence of the gene of the present invention as shown under SEQ ID NO:3n-1 (where n is an integer of 1 to 14) is merely an example of the codon combination encoding the respective amino acid residues. The gene of the present invention is not limited thereto but can of course have a DNA sequence in which the codons are arbitrarily selected and combined for the respective amino acid residues. The codon selection can be made in the conventional manner, for example taking into consideration the codon utilization frequencies in the host to be used [Nucl. Acids Res., 9, 43–74 (1981)].

The gene of the present invention further includes DNA sequences coding for functional equivalents derived from the amino acid sequence mentioned above by partial amino acid or amino acid sequence substitution, deletion or addition. These polypeptides may be produced by spontaneous modification (mutation) or may be obtained by posttranslational modification or by modifying the natural gene (of the present invention) by a technique of genetic engineering, for example by site-specific mutagenesis [Methods in Enzymology, 154, p. 350, 367–382 (1987); ibid., 100, p. 468 (1983); Nucleic Acids Research, 12, p. 9441 (1984); Zoku Seikagaku Jikken Koza (Sequel to Experiments in Biochemistry) 1, "Idensi Kenkyu-ho (Methods in Gene Research) II", edited by the Japan Biochemical Society, p. 105 (1986)] or synthesizing mutant DNAs by a chemical synthetic technique such as the phosphotriester method or phosphoamidite method [J. Am. Chem. Soc., 89, p. 4801 (1967); ibid., 91, p. 3350 (1969); Science, 150, p. 178 (1968); Tetrahedron Lett., 22, p. 1859 (1981); ibid., 24, p. 245 (1983)], or by utilizing the techniques mentioned above in combination.

The protein encoded by the gene of the present invention can be expressed readily and stably by utilizing said gene, for example inserting it into a vector for use with a microorganism and cultivating the microorganism thus transformed.

The protein obtained by utilizing the gene of the present invention can be used in specific antibody production. In this case, the protein producible in large quantities by the genetic engineering technique mentioned above can be used as the component to serve as an antigen. The antibody obtained may be polyclonal or monoclonal and can be advantageously used in the purification, assay, discrimination or identification of the corresponding protein.

The gene of the present invention can be readily produced based on the sequence information thereof disclosed herein by using general genetic engineering techniques [cf. e.g. Molecular Cloning, 2nd Ed., Cold Spring Harbor Laboratory Press (1989); Zoku Seikagaku Jikken Koza, "Idenshi Kenkyu-ho I, II and III", edited by the Japan Biochemical Society (1986)].

This can be achieved, for example, by selecting a desired clone from a human cDNA library (prepared in the conventional manner from appropriate cells of origin in which the gene is expressed) using a probe or antibody specific to the gene of the present invention [e.g. Proc. Natl. Acad. Sci. USA, 78, 6613 (1981); Science, 222, 778 (1983)].

The cells of origin to be used in the above method are, for example, cells or tissues in which the gene in question is expressed, or cultured cells derived therefrom. Separation of total RNA, separation and purification of mRNA, conversion to (synthesis of) cDNA, cloning thereof and so on can be carried out by conventional methods. cDNA libraries are also commercially available and such cDNA libraries, for example various cDNA libraries available from Clontech Lab. Inc. can also be used in the above method.

Screening of the gene of the present invention from these cDNA libraries can be carried out by the conventional method mentioned above. These screening methods include, for example, the method comprising selecting a cDNA clone by immunological screening using an antibody specific to the protein produced by the corresponding cDNA, the technique of plaque or colony hybridization using probes selectively binding to the desired DNA sequence, or a combination of these. As regards the probe to be used here, a DNA sequence chemically synthesized based on the information about the DNA sequence of the present invention is generally used. It is of course possible to use the gene of the present invention or fragments thereof as the proble.

Furthermore, a sense primer and an antisense primer designed based on the information about the partial amino acid sequence of a natural extract isolated and purified from cells or a tissue can be used as probes for screening.

For obtaining the gene of the present invention, the technique of DNA/RNA amplification by the PCR method [Science, 230, 1350–1354 (1984)] can suitably be employed. Particularly when the full-length cDNA can hardly be obtained from the library, the RACE method (rapid amplification of cDNA ends; Jikken Igaku (Experimental Medicine), 12 (6), 35–38 (1994)], in particular the 5'RACE method [Frohman, M. A., et al., Proc. Natl. Acad. Sci. USA, 85, 8998–9002 (1988)] is preferably employed. The primers to be used in such PCR method can be appropriately designed based on the sequence information of the gene of the present invention as disclosed herein and can be synthesized by a conventional method.

The amplified DNA/RNA fragment can be isolated and purified by a conventional method as mentioned above, for example by gel electrophoresis.

The nucleotide sequence of the thus-obtained gene of the present invention or any of various DNA fragments can be determined by a conventional method, for example the dideoxy method [Proc. Natl. Acad. Sci. USA, 74, 5463–5467 (1977)] or the Maxam-Gilbert method [Methods in Enzymology, 65, 499 (1980)]. Such nucleotide sequence determination can be readily performed using a commercially available sequence kit as well.

When the gene of the present invention is used and conventional techniques of recombinant DNA technology

[see e.g. Science, 224, p. 1431 (1984); Biochem. Biophys. Res. Comm., 130, p. 692 (1985); Proc. Natl. Acad. Sci. USA, 80, p. 5990 (1983) and the references cited above] are followed, a recombinant protein can be obtained. More detailedly, said protein can be produced by constructing a recombinant DNA enabling the gene of the present invention to be expressed in host cells, introducing it into host cells for transformation thereof and cultivating the resulting transformant.

In that case, the host cells may be eukaryotic or prokaryotic. The eukaryotic cells include vertebrate cells, yeast cells and so on, and the vertebrate cells include, but are not limited to, simian cells named COS cells [Cell, 23, 175–182 (1981)], Chinese hamster ovary cells and a dihydrofolate reductase-deficient cell line derived therefrom [Proc. Natl. Acad. Sci. USA, 77, 4216–4220 (1980)] and the like, which are frequently used.

As regards the expression vector to be used with vertebrate cells, an expression vector having a promoter located upstream of the gene to be expressed, RNA splicing sites, a polyadenylation site and a transcription termination sequence can be generally used. This may further have an origin of replication as necessary. As an example of said expression vector, there may be mentioned pSV2dhfr [Mol. Cell. Biol., 1, 854 (1981)], which has the SV40 early promoter. As for the eukaryotic microorganisms, yeasts are generally and frequently used and, among them, yeasts of the genus Saccharomyces can be used with advantage. As regards the expression vector for use with said yeasts and other eukaryotic microorganisms, pAM82 [Proc. Natl. Acad. Sci. USA, 80, 1–5 (1983)], which has the acid phosphatase gene promoter, for instance, can be used.

Furthermore, a prokaryotic gene fused vector can be preferably used as the expression vector for the gene of the present invention. As specific examples of said vector, there may be mentioned pGEX-2TK and pGEX-4T-2 which have a GST domain (derived from *S. japonicum*) with a molecular weight of 26,000.

*Escherichia coli* and *Bacillus subtilis* are generally and preferably used as prokaryotic hosts. When these are used as hosts in the practice of the present invention, an expression plasmid derived from a plasmid vector capable of replicating in said host organisms and provided in this vector with a promoter and the SD (Shine and Dalgarno) sequence upstream of said gene for enabling the expression of the gene of the present invention and further provided with an initiation codon (e.g. ATG) necessary for the initiation of protein synthesis is preferably used. The *Escherichia coli* strain K12, among others, is preferably used as the host *Escherichia coli*, and pBR322 and modified vectors derived therefrom are generally and preferably used as the vector, while various known strains and vectors can also be used. Examples of the promoter which can be used are the tryptophan (trp) promoter, lpp promoter, lac promoter and PL/PR promoter.

The thus-obtained desired recombinant DNA can be introduced into host cells for transformation by using various general methods. The transformant obtained can be cultured by a conventional method and the culture leads to expression and production of the desired protein encoded by the gene of the present invention. The medium to be used in said culture can suitably be selected from among various media in conventional use according to the host cells employed. The host cells can be cultured under conditions suited for the growth thereof.

In the above manner, the desired recombinant protein is expressed and produced and accumulated or secreted within the transformant cells or extracellularly or on the cell membrane.

The recombinant protein can be separated and purified as desired by various separation procedures utilizing the physical, chemical and other properties thereof [cf. e.g. "Seikagaku (Biochemistry) Data Book II", pages 1175–1259, 1st Edition, 1st Printing, published Jun. 23, 1980 by Tokyo Kagaku Dojin; Biochemistry, 25 (25), 8274–8277 (1986); Eur. J. Biochem., 163, 313–321 (1987)]. Specifically, said procedures include, among others, ordinary reconstitution treatment, treatment with a protein precipitating agent (salting out), centrifugation, osmotic shock treatment, sonication, ultrafiltration, various liquid chromatography techniques such as molecular sieve chromatography (gel filtration), adsorption chromatography, ion exchange chromatography, affinity chromatography and high-performance liquid chromatography (HPLC), dialysis and combinations thereof. Among them, affinity chromatography utilizing a column with the desired protein bound thereto is particularly preferred.

Furthermore, on the basis of the sequence information about the gene of the present invention as revealed by the present invention, for example by utilizing part or the whole of said gene, it is possible to detect the expression of the gene of the present invention in various human tissues. This can be performed by a conventional method, for example by RNA amplification by RT-PCR (reverse transcribed-polymerase chain reaction) [Kawasaki, E. S., et al., Amplification of RNA, in PCR Protocol, A guide to methods and applications, Academic Press, Inc., San Diego, 21–27 (1991)], or by northern blotting analysis [Molecular Cloning, Cold Spring Harbor Laboratory (1989)], with good results.

The primers to be used in employing the above-mentioned PCR method are not limited to any particular ones provided that they are specific to the gene of the present invention and enable the gene of the present invention alone to be specifically amplified. They can be designed or selected appropriately based on the gene information provided by the present invention. They can have a partial sequence comprising about 20 to 30 nucleotides according to the established practice. Suitable examples are as shown in Examples 1 to 11.

Thus, the present invention also provides primers and/or probes useful in specifically detecting such novel gene.

By using the novel gene provided by the present invention, it is possible to detect the expression of said gene in various tissues, analyze the structure and function thereof and, further, produce the human protein encoded by said gene in the manner of genetic engineering. These make it possible to analyze the expression product, reveal the pathology of a disease associated therewith, for example a genopathy or cancer, and diagnose and treat the disease.

The following drawings are referred to in the examples.

EXAMPLES

Figure 1:
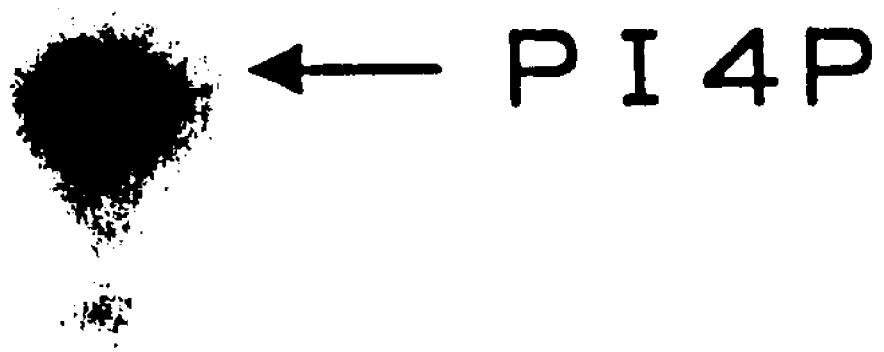
FIG. 1 shows the result obtained by testing the PI4 kinase activity of NPIK in Example 9.
Figure 1:

The following examples illustrate the present invention in further detail.

Example 1

GDP Dissociation Stimulator Gene

1) Cloning and DNA Sequencing of GDP Dissociation Stimulator Gene mRNAs extracted from the tissues of human fetal brain, adult blood vessels and placenta were purchased from Clontech and used as starting materials.

cDNA was synthesized from each mRNA and inserted into the vector λZAPII (Stratagene) to thereby construct a cDNA library (Otsuka GEN Research Institute, Otsuka Pharmaceutical Co., Ltd.)

Human gene-containing *Escherichia coli* colonies were allowed to form on agar medium by the in vivo excision technique [Short, J. M., et al., Nucleic Acids Res., 16, 7583–7600 (1988)]. Colonies were picked up at random and human gene-containing *Escherichia coli* clones were registered on 96-well micro plates. The clones registered were stored at −80° C.

Each of the clones registered was cultured overnight in 1.5 ml of LB medium, and DNA was extracted and purified using a model PI-100 automatic plasmid extractor (Kurabo). Contaminant *Escherichia coli* RNA was decomposed and removed by RNase treatment. The DNA was dissolved to a final volume of 30 µl. A 2-µl portion was used for roughly checking the DNA size and quantity using a minigel, 7 µl was used for sequencing reactions and the remaining portion (21 µl) was stored as plasmid DNA at 4° C.

This method, after slight changes in the program, enables extraction of the cosmid, which is useful also as a probe for FISH (fluorescence in situ hybridization) shown later in the examples.

Then, the dideoxy terminator method of Sanger et al. [Sanger, F., et al., Proc. Natl. Acad. Sci. USA, 74, 5463–5467 (1977)] using T3, T7 or a synthetic oligonucleotide primer or the cycle suquence method [Carothers, A. M., et al., Bio. Techniques, 7, 494–499 (1989)] comprising the dideoxy chain terminator method plus PCR method was carried out. These are methods of terminating the extension reaction specifically to the four bases using a small amount of plasmid DNA (about 0.1 to 0.5 µg) as a template.

The sequence primers used were FITC (fluorescein isothiocyanate)-labeled ones. Generally, about 25 cycles of reaction were performed using Taq polymerase. The PCR products were separated on a polyacrylamide urea gel and the fluorescence-labeled DNA fragments were submitted to an automatic DNA sequencer (ALF™ DNA Sequencer; Pharmacia) for determining the sequence of about 400 bases from the 5' terminus side of cDNA.

Since the 3' nontranslational region is high in heterogeneity for each gene and therefore suited for discriminating individual genes from one another, sequencing was performed on the 3' side as well depending on the situation.

The vast sum of nucleotide sequence information obtained from the DNA sequencer was transferred to a 64-bit DEC 3400 computer for homology analysis by the computer. In the homology analysis, a data base (GenBank, EMBL) was used for searching according to the UWGCG FASTA program [Pearson, W. R. and Lipman, D. J., Proc. Natl. Acad. Sci. USA, 85, 2444–2448 (1988)].

As a result of arbitrary selection by the above method and of cDNA sequence analysis, a clone designated as GEN-501D08 and having a 0.8 kilobase insert was found to show a high level of homology to the C terminal region of the human Ral guanine nucleotide dissociation stimulator (RalGDS) gene. Since RalGDS is considered to play a certain role in signal transmission pathways, the whole nucleotide sequence of the cDNA insert portion providing the human homolog was further determined.

Low-molecular GTPases play an important role in transmitting signals for a number of cell functions including cell proliferation, differentiation and transformation [Bourne, H. R. et al., Nature, 348, 125–132 (1990); Bourne et al., Nature, 349, 117–127 (1991)].

It is well known that, among them, those proteins encoded by the ras gene family function as molecular switches or, in other words, the functions of the ras gene family are regulated by different conditions of binding proteins such as biologically inactive GDP-binding proteins or active GDP-binding proteins, and that these two conditions are induced by GTPase activating proteins (GAPs) or GDS. The former enzymes induce GDP binding by stimulating the hydrolysis of bound GTP and the latter enzyme induces the regular GTP binding by releasing bound GDP [Bogusuki, M. S. and McCormick, F., Nature, 366, 643–654 (1993)].

RalGDS was first discovered as a member of the ras gene family lacking in transforming activity and as a GDP dissociation stimulator specific to RAS [Chardin, P. and Tavitian, A., EMBO J., 5, 2203–2208 (1986); Albright, C. F., et al., EMBO J., 12, 339–347 (1993)].

In addition to Ral, RalGDS was found to function, through interaction with these proteins, as an effector molecule for N-ras, H-ras, K-ras and Rap [Spaargaren, M. and Bischoff, J. R., Proc. Natl. Acad. Sci. USA, 91, 12609–12613 (1994)].

The nucleotide sequence of the cDNA clone designated as GEN-501D08 is shown under SEQ ID NO:3, the nucleotide sequence of the coding region of said clone under SEQ ID NO:2, and the amino acid sequence encoded by said nucleotide sequence under SEQ ID NO:1.

This cDNA comprises 842 nucleotides, including an open reading frame comprising 366 nucleotides and coding for 122 amino acids. The translation initiation codon was found to be located at the 28th nucleotide residue.

Comparison between the RalGDS protein known among conventional databases and the amino acid sequence deduced from said cDNA revealed that the protein encoded by this cDNA is homologous to the C terminal domain of human RalGDS. The amino acid sequence encoded by this novel gene was found to be 39.5% identical with the C terminal domain of RalGDS which is thought to be necessary for binding to ras.

Therefore, it is presumable, as mentioned above, that this gene product might interact with the ras family proteins or have influence on the ras-mediated signal transduction pathways. However, this novel gene is lacking in the region coding for the GDS activity domain and the corresponding protein seems to be different in function from the GDS protein. This gene was named human RalGDS by the present inventors.

(2) Northern Blot Analysis

The expression of the RalGDS protein mRNA in normal human tissues was evaluated by Northern blotting using, as a probe, the human cDNA clone labeled by the random oligonucleotide priming method.

The Northern blot analysis was carried out with a human MTN blot (Human Multiple Tissue Northern blot; Clontech, Palo Alto, Calif., USA) according to the manufacturer's protocol.

Thus, the PCR amplification product from the above GEN-501D08 clone was labeled with [$^{32}$P]-dCTP (random-primed DNA labeling kit, Boehringer-Mannheim) for use as a probe.

For blotting, hybridization was performed overnight at 42° C. in a solution comprising 50% formamide/5×SSC/50× Denhardt's solution/0.1% SDS (containing 100 µg/ml denatured salmon sperm DNA). After washing with two portions of 2×SSC/0.01% SDS at room temperature, the membrane filter was further washed three times with 0.1×SSC/0.05%

SDS at 50° C. for 40 minutes. An X-ray film (Kodak) was exposed to the filter at −70° C. for 18 hours.

As a result, it was revealed that a 900-bp transcript had been expressed in all the human tissues tested. In addition, a 3.2-kb transcript was observed specifically in the heart and skeletal muscle. The expression of these transcripts differing in size may be due either to alternative splicing or to cross hybridization with homologous genes.

(3) Cosmid Clone and Chromosome Localization by FISH

FISH was performed by screening a library of human chromosomes cloned in the cosmid vector pWE15 using, as a probe, the 0.8-kb insert of the cDNA clone [Sambrook, J., et al., Molecular Cloning, 2nd Ed., pp. 3.1–3.58, Cold Spring Harbor Laboratory Press, Cold Spring Harbor, N.Y. (1989)].

FISH for chromosome assignment was carried out by the method of Inazawa et al. which comprises G-banding pattern comparison for confirmation [Inazawa, J., et al., Genomics, 17, 153–162 (1993)].

For use as a probe, the cosmid DNA (0.5 μg) obtained from chromosome screening and corresponding to GEN-501D08 was labeled with biotin-16-dUTP by nick translation.

To eliminate the background noise due to repetitive sequences, 0.5 μl of sonicated human placenta DNA (10 mg/ml) was added to 9.5 μl of the probe solution. The mixture was denatured at 80° C. for 5 minutes and admixed with an equal volume of 4×SSC containing 20% dextransulfate. Then, a denatured slide was sown with the hybridization mixture and, after covering with paraffin, incubated in a wet chamber at 37° C. for 16 to 18 hours. After washing with 50% formamide/2×SSC at 37° C. for 15 minutes, the slide was washed with 2×SSC for 15 minutes and further with 1×SSC for 15 minutes.

The slide was then incubated in 4×SSC supplemented with "1% Block Ace" (trademark; Dainippon Pharmaceutical) containing avidin-FITC (5 μg/ml) at 37° C. for 40 minutes. Then, the slide was washed with 4×SSC for 10 minutes and with 4×SSC containing 0.05% Triton X-100 for 10 minutes and immersed in an antifading PPD solution [prepared by adjusting 100 mg of PPD (Wako Catalog No. 164-015321) and 10 ml of PBS(−) (pH 7.4) to pH 8.0 with 0.5 M Na$_2$CO$_3$/0.5 M NaHCO$_3$ (9:1, v/v) buffer (pH 9.0) and adding glycerol to make a total volume of 100 ml] containing 1% DABCO [1% DABCO (Sigma) in PBS(−):glycerol 1:9 (v:v)], followed by counter staining with DAPI (4,6-diamino-2-phenylindole; Sigma).

With more than 100 tested cells in the metaphase, a specific hybridization signal was observed on the chromosome band at 6p21.3, without any signal on other chromosomes. It was thus confirmed that the RalGDS gene is located on the chromosome 6p21.3.

By using the novel human RalGDS-associated gene of the present invention as obtained in this example, the expression of said gene in various tissues can be detected and the human RalGDS protein can be produced in the manner of genetic engineering. These are expected to enable studies on the roles of the expression product protein and ras-mediated signals in transduction pathways as well as pathological investigations of diseases in which these are. involved, for example cancer, and the diagnosis and treatment of such diseases. Furthermore, it becomes possible to study the development and progress of diseases involving the same chromosomal translocation of the RalGDS protein gene of the present invention, for example tonic spondylitis, atrial septal defect, pigmentary retinopathy, aphasia and the like.

Example 2

Cytoskeleton-associated Protein 2 Gene (CKAP2 Gene)

(1) Cytoskeleton-associated Protein 2 Gene Cloning and DNA Sequencing cDNA clones were arbitrarily chosen from a human fetal brain cDNA library in the same manner as in Example 1 were subjected to sequence analysis and, as a result, a clone having a base sequence containing the CAP-glycine domain of the human cytoskeleton-associated protein (CAP) gene and highly homologous to several CAP family genes was found and named GEN-080G01.

Meanwhile, the cytoskeleton occurs in the cytoplasm and just inside the cell membrane of eukaryotic cells and is a network structure comprising complicatedly entangled filaments. Said cytoskeleton is constituted of microtubules composed of tubulin, microfilaments composed of actin, intermediate filaments composed of desmin and vimentin, and so on. The cytoskeleton not only acts as supportive cellular elements but also isokinetically functions to induce morphological changes of cells by polymerization and depolymerization in the fibrous system. The cytoskeleton binds to intracellular organelles, cell membrane receptors and ion channels and thus plays an important role in intracellular movement and locality maintenance thereof and, in addition, is said to have functions in activity regulation and mutual information transmission. Thus it supposedly occupies a very important position in physiological activity regulation of the whole cell. In particular, the relation between canceration of cells and qualitative changes of the cytoskeleton attracts attention since cancer cells differ in morphology and recognition response from normal cells.

The activity of this cytoskeleton is modulated by a number of cytoskeleton-associated proteins (CAPs). One group of CAPs is characterized by a glycine motif highly conserved and supposedly contributing to association with microtubules [CAP-GLY domain; Riehemann, K. and Song, C., Trends Biochem. Sci., 18, 82–83 (1993)].

Among the members of this group of CAPS, there are CLIP-170, 150 kDa DAP (dynein-associated protein, or dynactin), D. melanogaster GLUED, S. cerevisiae BIK1, restin [Bilbe, G., et al., EMBO J., 11, 2103–2113 (1992)]; Hilliker, C., et al., Cytogenet. Cell Genet., 65, 172–176 (1994)] and C. elegans 13.5 kDa protein [Wilson, R., et al., Nature, 368, 32–38 (1994)]. Except for the last two proteins, direct or indirect evidences have suggested that they could interact with microtublues.

The above-mentioned CLIP-170 is essential for the in vitro binding of endocytic vesicles to microtubules and colocalizes with endocytic organelles [Rickard, J. E. and Kreis, T. E., J. Biol. Chem., 18, 82–83 (1990); Pierre, P., et al., Cell, 70, 887–900 (1992)].

The above-mentioned dynactin is one of the factors-constituting the cytoplasmic dynein motor, which functions in retrograde vesicle transport [Schroer, T. A. and Sheetz, M. P., J. Cell Biol., 115, 1309–1318 (1991)] or probably in the movement of chromosomes during mitosis [Pfarr, C. M., et al., Nature, 345, 263–265 (1990); Steuer, E. R., et al., Nature, 345, 266–268 (1990); Wordeman, L., et al., J. Cell Biol., 114, 285–294 (1991)].

GLUED, the Drosophila homolog of mammalian dynactin, is essential for the viability of almost all cells and for the proper organization of some neurons [Swaroop, A., et al., Proc. Natl. Acad. Sci. USA, 84, 6501–6505 (1987); Holzbaur, E. L. P., et al., Nature, 351, 579–583 (1991)].

BIK1 interacts with microtubules and plays an important role in spindle formation during mitosis in yeasts [Trueheart, J., et al., Mol. Cell. Biol., 7, 2316–2326 (1987); Berlin, V., et al., J. Cell Biol., 111, 2573–2586 (1990)].

At present, these genes are classified under the term CAP family (CAPs).

As a result of database searching, the above-mentioned cDNA clone of 463-bp (excluding the poly-A signal) showed significant homology in nucleotide sequence with the restin and CLIP-170 encoding genes. However, said clone was lacking in the 5' region as compared with the restin gene and, therefore, the technique of 5' RACE [Frohman, M. A., et al., Proc. Natl. Acad. Sci. USA, 85, 8998–9002 (1988)] was used to isolate this missing segment.

(2) 5' RACE (5' Rapid Amplification of cDNA Ends)

A cDNA clone containing the 5' portion of the gene of the present invention was isolated for analysis by the 5' RACE technique using a commercial kit (5'-Rapid AmpliFinder RACE kit, Clontech) according to the manufacturer's protocol with minor modifications, as follows.

The gene-specific primer P1 and primer P2 used here were synthesized by the conventional method and their nucleotide sequences are as shown below in Table 1. The anchor primer used was the one attached to the commercial kit.

TABLE 1

| Primer | Nucleotide sequence |
|---|---|
| Primer P1 | 5'-ACACCAATCCAGTAGCCAGGCTTG-3' (SEQ ID NO:43) |
| Primer P2 | 5'-CACTCGAGAATCTGTGAGACCTACATACATGACG-3' (SEQ ID NO:44) | cDNA was obtained by reverse transcription of 0.1 μg of human fetal brain poly(A)+RNA by the random hexamer technique using reverse transcriptase (Superscript™ II, Life Technologies) and the cDNA was amplified by the first PCR using the P1 primer and anchor primer according to Watanabe et al. [Watanabe, T., et al., Cell Genet., in press).

Thus, to 0.1 μg of the above-mentioned cDNA were added 2.5 mM dNTP/1×Taq buffer (Takara Shuzo)/0.2 μM P1 primer, 0.2 μM adaptor primer/0.25 unit ExTaq enzyme (Takara Shuzo) to make a total volume of 50 μl, followed by addition of the anchor primer. The mixture was subjected to PCR. Thus, 35 cycles of amplification were performed under the conditions: 94° C. for 45 seconds, 60° C. for 45 seconds, and 72° C. for 2 minutes. Finally, the mixture was heated at 72° C. for 5 minutes.

Then, 1 μl of the 50-μl first PCR product was subjected to amplification by the second PCR using the specific nested P2 primer and anchor primer. The second PCR product was analyzed by 1.5% agarose gel electrophoresis.

Upon agarose gel electrophoresis, a single band, about 650 nucleotides in size, was detected. The product from this band was inserted into a vector (pT7Blue(R)T-Vector, Novagen) and a plurality of clones with an insert having an appropriate size were selected.

Six of the 5' RACE clones obtained from the PCR product had the same sequence but had different lengths. By sequencing two overlapping cDNA clones, GEN-080G01 and GEN-080G0149, the protein-encoding sequence and 5' and 3' flanking sequences, 1015 nucleotides in total length, were determined. Said gene was named cytoskeleton-associated protein 2 gene (CKAP2 gene).

The nucleotide sequence obtained from the above-mentioned two overlapping cDNA clones GEN-080G01 and GEN-080G0149 is shown under SEQ ID NO:6, the nucleotide sequence of the coding region of said clone under SEQ ID NO:5, and the amino acid sequence encoded by said nucleotide sequence under SEQ ID NO:4.

As shown under SEQ ID NO:6, the CKAP2 gene had a relatively GC-rich 5' noncoding region, with incomplete triplet repeats, (CAG)4(CGG)4(CTG)(CGG), occurring at nucleotides 40–69.

ATG located at nucleotides 274–276 is the presumable start codon. A stop codon (TGA) was situated at nucleotides 853–855. A polyadenylation signal (ATTAAA) was followed by 16 nucleotides before the poly(A) start. The estimated open reading frame comprises 579 nucleotides coding for 193 amino acid residues with a calculated molecular weight of 21,800 daltons.

The coding region was further amplified by RT-PCR, to eliminate the possibility of the synthetic sequence obtained being a cDNA chimera.

(2) Similarity of CKAP2 to Other CAPs

While sequencing of CKAP2 revealed homology with the sequences of restin and CLIP-170, the homologous region was limited to a short sequence corresponding to the CAP-GLY domain. On the amino acid level, the deduced CKAP2 was highly homologous to five other CAPs in this domain.

CKAP2 was lacking in such other motif characteristics of some CAPs as the alpha helical rod and zinc finger motif.

The alpha helical rod is thought to contribute to dimerization and to increase the microtubule binding capacity [Pierre, P., et al., Cell, 70, 887–900 (1992)]. The lack of the alpha helical domain might mean that CKAP2 be incapable of homo or hetero dimer formation.

Paralleling of the CAP-GLY domains of these proteins revealed that other conserved residues other than glycine residues are also found in CKAP2. CAPs having a CAP-GLY domain are thought to be associated with the activities of cellular organelles and the interactions thereof with microtubules. Since it contains a CAP-GLY domain, as mentioned above, CKAP2 is placed in the family of CAPs.

Studies with mutants of Glued have revealed that the Glued product plays an important role in almost all cells [Swaroop, A., et al., Proc. Natl. Acad. Sci. USA, 84, 6501–6505 (1987)] and that it has other neuron-specific functions in neuronal cells [Meyerowitz, E. M. and Kankel, D. R., Dev. Biol., 62, 112–142 (1978)]. These microtubule-associated proteins are thought to function in vesicle transport and mitosis. Because of the importance of the vesicle transport system in neuronal cells, defects in these components might lead to aberrant neuronal systems.

In view of the above, CKAP2 might be involved in specific neuronal functions as well as in fundamental cellular functions.

(3) Northern Blot Analysis

The expression of human CKAP2 mRNA in normal human tissues was examined by Northern blotting in the same manner as in Example 1 (2) using the GEN-080G01 clone (corresponding to nucleotides 553–1015) as a probe.

As a result, in all the eight tissues tested, namely human heart, brain, placenta, lung, liver, skeletal muscle, kidney and pancreas, a 1.0 kb transcript agreeing in size with the CKAP2 cDNA was detected. Said 1.0 kb transcript was expressed at significantly higher levels in heart and brain than in the other tissues examined. Two weak bands, 3.4 kb and 4.6 kb, were also detected in all the tissues examined.

According to the Northern blot analysis, the 3.4 kb and 4.6 kb transcripts might possibly be derived from the same gene coding for the 1.0 kb CKAP2 by alternative splicing or transcribed from other related genes. These characteristics of the transcripts may indicate that CKAP2 might also code for a protein having a CAP-GLY domain as well as an alpha helix.

(4) Cosmid Cloning and Chromosomal Localization by Direct R-banding FISH

Two cosmids corresponding to the CKAP2 cDNA were obtained. These two cosmid clones were subjected to direct R-banding FISH in the same manner as in Example 1 (3) for chromosomal locus mapping of CKAP2.

For suppressing the background due to repetitive sequences, a 20-fold excessive amount of human Cot-I DNA (BRL) was added as described by Lichter et al. [Lichter, P., et al., Proc. Natl. Acad. Sci. USA, 87, 6634–6638 (1990)]. A Provia 100 film (Fuji ISO 100; Fuji Photo Film) was used for photomicrography.

As a result, CKAP2 was mapped on chromosome bands 19q13.11-q13.12.

Two autosomal dominant neurological diseases have been localized to this region by linkage analysis: CADASIL (cerebral autosomal dominant arteriopathy with subcortical infarcts and leukoencephalopathy) between the DNA markers D19S221 and D19S222, and FHM (familial hemiplegic migraine) between D19S215 and D19S216. These two diseases may be allelic disorders in which the same gene is involved [Tournier-Lasserve, E., et al., Nature Genet., 3, 256–259 (1993); Joutel, A., et al., Nature Genet., 5, 40–45 (1993)].

Although no evidence is available to support CKAP2 as a candidate gene for FHM or CADASIL, it is conceivable that its mutation might lead to some or other neurological disease.

By using the novel human CKAP2 gene of the present invention as obtained in this example, it is possible to detect the expression of said gene in various tissues or produce the human CKAP2 gene in the manner of genetic engineering. Through these, it becomes possible to analyze the functions of the human CKAP2 system or human CKAP2, which is involved in diverse activities essential to cells, as mentioned above, to diagnose various neurological diseases in which said system or gene is involved, for example familial migraine, and to screen out and evaluate a therapeutic or prophylactic drug therefor.

Example 3

OTK27 Gene (1) OTK27 Gene Cloning and DNA Sequencing

As a result of sequence analysis of cDNA clones arbitraily selected from a human fetal brain cDNA library in the same manner as in Example 1 (1) and database searching, a cDNA clone, GEN-025F07, coding for a protein highly homologous to NHP2, a yeast nucleoprotein [Saccharomyces cerevisiae; Kolodrubetz, D. and Burgum, A., YEAST, 7, 79–90 (1991)], was found and named OTK27.

Nucleoproteins are fundamental cellular constituents of chromosomes, ribosomes and so forth and are thought to play an essential role in cell multiplication and viability. The yeast nucleoprotein NHP2, a high-mobility group (HMG)-like protein, like HMG, has reportedly a function essential for cell viability [Kolodrubetz, D. and Burgum, A., YEAST, 7, 79–90 (1991)].

The novel human gene, OTK27 gene, of the present invention, which is highly homologous to the above-mentioned yeast NHP2 gene, is supposed to be similar in function.

The nucleotide sequence of said GEN-025F07 clone was found to comprise 1493 nucleotides, as shown under SEQ ID NO:9, and contain an open reading frame comprising 384 nucleotides, as shown under SEQ ID NO:8, coding for an amino acid sequence comprising 128 amino acid residues, as shown under SEQ ID NO:7. The initiation codon was located at nucleotides 95–97 of the sequence shown under SEQ ID NO:9, and the termination codon at nucleotides 479–481.

At the amino acid level, the OTK27 protein was highly homologous (38%) to NHP2. It was 83% identical with the protein deduced from the cDNA from *Arabidopsis thaliana*; Newman, T., unpublished; GENEMBL Accession No. T14197).

(2) Northern Blot Analysis

For examining the expression of human OTK27 mRNA in normal human tissues, the insert in the OTK27 cDNA was amplified by PCR, the PCR product was purified and labeled with [$^{32}$P]-dCTP (random-primed DNA labeling kit, Boehringer Mannheim), and Northern blotting was performed using the labeled product as a probe in the same manner as in Example 1 (2).

As a result of the Northern blot analysis, two bands corresponding to possible transcripts from this gene were detected at approximately 1.6 kb and 0.7 kb. Both sizes of transcript were expressed in all normal adult tissues examined. However, the expression of the 0.7 kb transcript was significantly reduced in brain and was of higher levels in heart, skeletal muscle and testicle than in other tissues examined.

For further examination of these two transcripts, eleven cDNA clones were isolated from a testis cDNA library and their DNA sequences were determined in the same manner as in Example 1 (1).

As a result, in six clones, the sequences were found to be in agreement with that of the 0.7 kb transcript, with a poly(A) sequence starting at around the 600th nucleotide, namely at the 598th nucleotide in two of the six clones, at the 606th nucleotide in three clones, and at the 613th nucleotide in one clone.

In these six clones, the "TATAAA" sequence was recognized at nucleotides 583–588 as a probable poly(A) signal. The upstream poly(A) signal "TATAAA" of this gene was recognized as little influencing in brain and more effective in the three tissues mentioned above than in other tissues. The possibility was considered that the stability of each transcript vary from tissue to tissue.

Results of zoo blot analysis indicated that this gene is well conserved also in other vertebrates. Since this gene is expressed ubiquitously in normal adult tissues and conserved among a wide range of species, the gene product is likely to play an important physiological role. The evidence that yeasts lacking in NHP2 are nonviable suggests that the human homolog may also be essential to cell viability.

(3) Chromosomal Localization of OTK27 by Direct R-banding FISH

One cosmid clone corresponding to the cDNA OTK27 was isolated from a total human genomic cosmid library (5-genome equivalent) using the OTK27 cDNA insert as a probe and subjected to FISH in the same manner as in Example 1 (3) for chromosomal localization of OTK27.

As a result, two distinct spots were observed on the chromosome band 12q24.3.

The OTK27 gene of the present invention can be used in causing expression thereof and detecting the OTK27 protein, a human nucleoprotein, and thus can be utilized in the diagnosis and pathologic studies of various diseases in which said protein is involved and, because of its involvement in cell proliferation and differentiation, in screening out and evaluating therapeutic and preventive drugs for cancer.

Example 4

OTK18 Gene (1) OTK18 Gene Cloning and DNA Sequencing

Zinc finger proteins are defined as constituting a large family of transcription-regulating proteins in eukaryotes and carry evolutionarily conserved structural motifs [Kadonaga, J. T., et al., Cell, 51, 1079–1090 (1987); Klung, A. and Rhodes, D., Trends Biol. Sci., 12, 464–469 (1987); Evans, R. M. and Hollenberg, S. M., Cell, 52, 1–3 (1988)].

The zinc finger, a loop-like motif formed by the interaction between the zinc ion and two residues, cysteine and histidine residues, is involved in the sequence-specific binding of a protein to RNA or DNA. The zinc finger motif was first identified within the amino acid sequence of the Xenopus transcription factor IIIA [Miller, J., et al., EMBO J., 4, 1609–1614 (1986)].

The $C_2H_2$ finger motif is in general tandemly repeated and contains an evolutionarily conserved intervening sequence of 7 or 8 amino acids. This intervening stretch was first identified in the Kruppel segmentation gene of Drosophila [Rosenberg, U. B., et al., Nature, 319, 336–339 (1986)]. Since then, hundreds of $C_2H_2$ zinc finger protein-encoding genes have been found in vertebrate genomes.

As a result of sequence analysis of cDNA clones arbitrarily selected from a human fetal brain cDNA library in the same manner as in Example 1 (1) and database searching, several zinc finger structure-containing clones were identified and, further, a clone having a zinc finger structure of the Kruppel type was found.

Since this clone lacked the 5' portion of the transcript, plaque hybridization was performed with a fetal brain cDNA library using, as a probe, an approximately 1.8 kb insert in the cDNA clone, whereby three clones were isolated. The nucleotide sequences of these were determined in the same manner as in Example 1 (1).

Among the three clones, the one having the largest insert spans 3,754 nucleotides including an open reading frame of 2,133 nucleotides coding for 711 amino acids. It was found that said clone contains a novel human gene coding for a peptide highly homologous in the zinc finger domain to those encoded by human ZNF41 and the Drosophila Kruppel gene. This gene was named OTK18 gene (derived from the clone GEN-076C09).

The nucleotide sequence of the cDNA clone of the OTK18 gene is shown under SEQ ID NO:12, the coding region-containing nucleotide sequence under SEQ ID NO:11, and the predicted amino acid sequence encoded by said OTK18 gene under SEQ ID NO:10.

It was found that the amino acid sequence of OTK18 as deduced from SEQ ID NO:12 contains 13 finger motifs on its carboxy side.

(2) Comparison with Other Zinc Finger Motif-containing Genes

Comparison among OTK18, human ZNF41 and the Drosophila Kruppel gene revealed that each finger motif is for the most part conserved-in the consensus sequence CXECGKAFXQKSXLX$_2$HQRXH (SEQ ID NO:45).

Comparison of the consensus sequence of the zinc finger motifs of OTK18 with those of human ZNF41 and the Drosophila Kruppel gene revealed that the Kruppel type motif is well conserved in the OTK18-encoded protein. However, the sequence similarities were limited to zinc finger domains and no significant homologies were found with regard to other regions.

The zinc finger domain interacts specifically with the target DNA, recognizing an about 5 bp sequence to thereby bind to the DNA helix [Rhodes, D. and Klug, A., Cell, 46, 123–132 (1986)].

Based on the idea that, in view of the above, the multiple module (tandem repetitions of zinc finger) can interact with long stretches of DNA, it is presumable that the target DNA of this gene product containing 13 repeated zinc finger units would be a DNA fragment with a length of approximately 65 bp.

(3) Northern Blot Analysis

Northern blot analysis was performed as described in Example 1 (2) for checking normal human tissues for expression of the human OTK18 mRNA therein by amplifying the insert of the OTK18 cDNA by PCR, purifying the PCR product, labeling the same with [$^{32}$P]-dCTP (random-primed DNA labeling kit, Boehringer Mannheim) and using an MTN blot with the labeled product as a probe.

The results of Northern blot analysis revealed that the transcript of OTK18 is approximately 4.3 kb long and is expressed ubiquitously in various normal adult tissues. However, the expression level in the liver and in peripheral blood lymphocytes seemed to be lower than in other organs tested.

(4) Cosmid Cloning and Chromosomal Localization by Direct R-banding FISH

Chromosomal localization of OTK18 was carried out as described in Example 1 (3).

As a result, complete twin spots were identified with 8 samples while 23 samples showed an incomplete signal or twin spots on either or both homologs. All signals appeared at the q13.4 band of chromosome 19. No twin spots were observed on any other chromosomes.

The results of FISH thus revealed that this gene is localized on chromosomal band 19q13.4. This region is known to contain many DNA segments that hybridize with oligonucleotides corresponding to zinc finger domains [Hoovers, J. M. N., et al., Genomics, 12, 254–263 (1992)]. In addition, at least one other gene coding for a zinc finger domain has been identified in this region [Marine, J.-C., et al., Genomics, 21, 285–286 (1994)].

Hence, the chromosome 19q13 is presumably a site of grouping of multiple genes coding for transcription-regulating proteins.

When the novel human OTK18 gene provided by this example is used, it becomes possible to detect expression of said gene in various tissues and produce the human OTK18 protein in the manner of genetic engineering. Through these, it is possible to analyze the functions of the human transcription regulating protein gene system or human transcription regulating proteins, which are deeply involved in diverse activities fundamental to cells, as mentioned above, to diagnose various diseases with which said gene is associated, for example malformation or cancer resulting from a developmental or differentiation anomaly, and mental or nervous disorder resulting from a developmental anomaly in the nervous system, and further to screen out and evaluate therapeutic or prophylactic drugs for these diseases.

Example 5

Genes Encoding Human 26S Proteasome Constituent P42 Protein and P27 Protein (1) Cloning and DNA Sequencing of Genes Respectively Encoding Human 26S Proteasome Constituent P42 Protein and P27 Protein Proteasome, which is a multifunctional protease, is an enzyme occurring widely in eukaryotes from yeasts to humans and decomposing ubiquitin-binding proteins in cells in an energy-dependent manner. Structurally, said proteasome is constituted of 20S proteasome composed of various constituents with a molecular weight of 21 to 31 kilodaltons and a group of PA700 regulatory proteins composed of various constituents with a molecular weight of 30 to 112 kilodaltons and showing a sedimentation coefficient of 22S and, as a whole, occurs as a macromolecule with a molecular weight of about 2 million daltons and a sedimentation coefficient of 26S [Rechsteiner, M., et al., J. Biol. Chem., 268, 6065–6068 (1993); Yoshimura, T., et al., J. Struct. Biol., 111, 200–211 (1993); Tanaka, K., et al., New Biologist, 4, 173–187 (1992)].

Despite structural and mechanical analyses thereof, the whole picture of proteasome is not yet fully clear. However, according to studies using yeasts and mice in the main, it reportedly has the functions mentioned below and its functions are becoming more and more elucidated.

The mechanism of energy-dependent proteolysis in cells starts with selection of proteins by ubiquitin binding. It is not 20S proteasome but 26S proteasome that has ubiquitin-conjugated protein decomposing activity which is ATP-dependent [Chu-Ping et al., J. Biol. Chem., 269, 3539–3547 (1994)]. Hence, human 26S proteasome is considered to be useful in elucidating the mechanism of energy-dependent proteolysis.

Factors involved in the cell cycle regulation are generally short in half-life and in many cases they are subject to strict quantitative control. In fact, it has been made clear that the oncogene products Mos, Myc, Fos and so forth can be decomposed by 26S proteasome in an energy- and ubiquitin-dependent manner [Ishida, N., et al., FEBS.Lett., 324, 345–348 (1993); Hershko, A. and Ciechanover, A., Annu. Rev. Biochem., 61, 761–807 (1992)] and the importance of proteasone in cell cycle control is being recognized.

Its importance in the immune system has also been pointed out. It is suggested that proteasome is positively involved in class I major histocompatible complex antigen presentation [Michalek, M. T., et al., Nature, 363, 552–554 (1993)] and it is further suggested that proteasome may be involved in Alzheimer disease, since the phenomena of abnormal accumulation of ubiquitin-conjugated proteins in the brain of patients with Alzheimer disease [Kitaguchi, N., et al., Nature, 361, 530–532 (1988)]. Because of its diverse functions such as those mentioned above, proteasome attracts attention from the viewpoint of its utility in the diagnosis and treatment of various diseases.

A main function of 26S proteasome is ubiquitin-conjugated protein decomposing activity. In particular, it is known that cell cycle-related gene products such as oncogene products and cyclins, typically c-Myc, are degraded via ubiquitin-dependent pathways. It has also been observed that the proteasome gene is expressed abnormally in liver cancer cells, renal cancer cells, leukemia cells and the like as compared with normal cells [Kanayama, H., et al., Cancer Res., 51, 6677–6685 (1991)] and that proteasome is abnormally accumulated in tumor cell nuclei. Hence, constituents of proteasome are expected to be useful in studying the mechanism of such canceration and in the diagnosis or treatment of cancer.

Also, it is known that the expression of proteasome is induced by interferon γ and so on and is deeply involved in antigen presentation in cells [Aki, M., et al., J. Biochem., 115, 257–269 (1994)]. Hence, constituents of human proteasome are expected to be useful in studying the mecha- nism of antigen presentation in the immune system and in developing immunoregulating drugs.

Furthermore, proteasome is considered to be deeply associated with ubiquitin abnormally accumulated in the brain of patients with Alzheimer disease. Hence, it is suggested that constituents of human proteasome should be useful in studying the cause of Alzheimer disease and in the treatment of said disease.

In addition to the utilization of expectedly multifunctional proteasome as such in the above manner, it is probably possible to produce antibodies using constituents of proteasome as antigens and use such antibodies in diagnosing various diseases by immunoassay. Its utility in this field of diagnosis is thus also a focus of interest.

Meanwhile, a protein having the characteristics of human 26S proteasome is disclosed, for example in Japanese Unexamined Patent Publication No. 292964/1993 and rat proteasome constituents are disclosed in Japanese Unexamined Patent Publication Nos. 268957/1993 and 317059/1993. However, no human 26S proteasome constituents are known. Therefore, the present inventors made a further search for human 26S proteasome constituents and successfully obtained two novel human 26S proteasome constituents, namely human 26S proteasome constituent P42 protein and human S26 proteasome constituent P27 protein, and performed cloning and DNA sequencing of the corresponding genes in the following manner.

(1) Purification of Human 26S Proteasome Constituents P42 Protein and P27 Protein Human proteasome was purified using about 100 g of fresh human kidney and following the method of purifying human proteasome as described in Japanese Unexamined Patent Publication No. 292964/1993, namely by column chromatography using BioGel A-1.5 m (5×90 cm, Bio-Rad), hydroxyapatite (1.5×15 cm, Bio-Rad) and Q-Sepharose (1.5×15 cm, Pharmacia) and glycerol density gradient centrifugation.

The thus-obtained human proteasome was subjected to reversed phase high performance liquid chromatography (HPLC) using a Hitachi model L6200 HPLC system. A Shodex RS Pak D4-613 (0.6×15 cm, Showa Denko) was used and gradient elution was performed with the following two solutions:

First solution: 0.06% trifluoroacetic acid;

Second solution: 0.05% trifluoroacetic acid, 70% acetonitrile.

An aliquot of each eluate fraction was subjected to 8.5% SDS-polyacrylamide electrophoresis under conditions of reduction with dithiothreitol. The P42 protein and P27 protein thus detected were isolated and purified.

The purified P42 and P27 proteins were respectively digested with 1 μg of trypsin in 0.1 M Tris buffer (pH 7.8) containing 2 M urea at 37° C. for 8 hours and the partial peptide fragments obtained were separated by reversed phase HPLC and their sequences were determined by Edman degradation. The results obtained are as shown below in Table 2.

TABLE 2

| Partial protein | Amino acid sequence |
|---|---|
| P42 (1) | VLNISLW (SEQ ID NO:46) |
| (2) | TLMELLNQMDGFDTLHR (SEQ ID NO:47) |
| (3) | AVSDFVVSEYXMXA (SEQ ID NO:48) |
| (4) | EVDPLVYNX (SEQ ID NO:49) |
| (5) | HGEIDYEAIVK (SEQ ID NO:50) |
| (6) | LSXGFNGADLRNVXTEAGMFAIXAD (SEQ ID NO:51) |
| (7) | MIMATNRPDTLDPALLRPGXL (SEQ ID NO:52) |
| (8) | IHIDLPNEQARLDILK (SEQ ID NO:53) |
| (9) | ATNGPRYVVVG (SEQ ID NO:54) |
| (10) | EIDGRLK (SEQ ID NO:55) |
| (11) | ALQSVGQIVGEVLK (SEQ ID NO:56) |
| (12) | ILAGPITK (SEQ ID NO:57) |
| (13) | XXVIELPLTNPELFQG (SEQ ID NO:58) |
| (14) | VVSSSLVDK (SEQ ID NO:59) |
| (15) | ALQDYRK (SEQ ID NO:60) |
| (16) | EHREQLK (SEQ ID NO:61) |
| (17) | KLESKLDYKPVR (SEQ ID NO:62) |
| P27 (1) | LVPTR (SEQ ID NO:63) |
| (2) | AKEEEIEAQIK (SEQ ID NO:64) |
| (3) | ANYEVLESQK (SEQ ID NO:65) |
| (4) | VEDALHQLHAR (SEQ ID NO:66) |
| (5) | DVDLYQVR (SEQ ID NO:67) |
| (6) | QSQGLSPAQAFAK (SEQ ID NO:68) |
| (7) | AGSQSGGSPEASGVTVSDVQE (SEQ ID NO:69) |
| (8) | GLLGXNIIPLQR (SEQ ID NO:70) |

(2) cDNA Library Screening, Clone Isolation and cDNA Nucleotide Sequence Determination As mentioned in Example 1 (1), the present inventors have a database comprising about 30,000 cDNA data as constructed based on large-scale DNA sequencing using human fetal brain, arterial blood vessel and placenta cDNA libraries.

Based on the amino acid sequences obtained as mentioned above in (1), computer searching was performed with the FASTA program (search for homology between said amino acid sequences and the amino acid sequences estimated from the database). As regards P42, a clone (GEN-331G07) showing identity with regard to two amino acid sequences [(2) and (7) shown in table 2] was screened out and, as regards P27, a clone (GEN-163D09) showing identity with regard to two amino acid sequences [(1) and (8) shown in Table 2] was found.

For each of these clones, the 5' side sequence was determined by 5' RACE and the whole sequence was determined, in the same manner as in Example 2 (2).

As a result, it was revealed that the above-mentioned P42 clone GEN-331G07 comprises a 1,566-nucleotide sequence as shown under SEQ ID NO:15, inclusive of a 1,167-nucleotide open reading frame as shown under SEQ ID NO:14, and that the amino acid sequence encoded thereby is the one shown under SEQ ID NO:13 and comprises 389 amino acid residues.

The results of computer homology search revealed that the P42 protein is significantly homologous to the AAA (ATPase associated with a variety of cellular activities) protein family (e.g. P45, TBP1, TBP7, S4, MSS1, etc.). It was thus suggested that it is a new member of the AAA protein family.

As for the P27 clone GEN-163D09, it was revealed that it comprises a 1,128-nucleotide sequence as shown under SEQ ID NO:18, including a 669-nucleotide open reading frame as shown under SEQ ID NO:17 and that the amino acid sequence encoded thereby is the one shown under SEQ ID NO:16 and comprises 223 amino acid residues.

As regards the P27 protein, homology search using a computer failed to reveal any homologous gene among public databases. Thus, the gene in question is presumably a novel gene having an unknown function.

Originally, the above-mentioned P42 and P27 gene products were both purified as regulatory subunit components of proteasome complex. Therefore, these are expected to play an important role in various biological functions through proteolysis, for example a role in energy supply through decomposition of ATP and, hence, they are presumably useful not only in studying the function of human 26S proteasome but also in the diagnosis and treatment of various diseases caused by lowering of said biological functions, among others.

Example 6

BNAP Gene (1) BNAP Gene Cloning and DNA Sequencing

The nucleosome composed of DNA and histone is a fundamental structure constituting chromosomes in eukaryotic cells and is well conserved over borders among species. This structure is closely associated with the processes of replication and transcription of DNA. However, the nucleosome formation is not fully understood as yet. Only certain specific factors involved in nucleosome assembly (NAPs) have been identified. Thus, two acidic proteins, nucleoplasmin and N1, are already known to facilitate nucleosome construction [Kleinschmidt, J. A., et al., J. Biol. Chem., 260, 1166–1176 (1985); Dilworth, S. M., et al., Cell, 51, 1009–1018 (1987)].

A yeast gene, NAP-I, was isolated using a monoclonal antibody and recombinant proteins derived therefrom were tested as to whether they have nucleosome assembling activity in vivo.

More recently, a mouse NAP-I gene, which is a mammalian homolog of the yeast NAP-I gene was cloned (Okuda, A.; registered in database under the accession number D12618). Also cloned were a mouse gene, DN38 [Kato, K., Eur. J. Neurosci., 2, 704–711 (1990)] and a human nucleosome assembly protein (hNRP) [Simon, H. U., et al., Biochem. J., 297, 389–397 (1994)]. It was shown that the hNRP gene is expressed in many tissues and is associated with T lymphocyte proliferation.

The present inventors performed sequence analysis of cDNA clones arbitrarily chosen from a human fetal brain cDNA library in the same manner as in Example 1 (1), followed by searches among databases and, as a result, made it clear that a 1,125-nucleotide cDNA clone (free of poly (A)), GEN-078D05, is significantly homologous to the mouse NAP-I gene, which is a gene for a nucleosome assembly protein (NAP) involved in nucleosome construction, a mouse partial cDNA clone, DN38, and hNRP.

Since said clone GEN-078D05 was lacking in the 5' region, 5' RACE was performed in the same manner as in Example 2 (2) to obtain the whole coding region. For this 5' RACE, primers P1 and P2 respectively having the nucleotide sequences shown below in Table 3.

TABLE 3

| Primer | Nucleotide sequence |
|---|---|
| Primer P1 | 5'-TTGAAGAATGATGCATTAGGAACCAC-3' (SEQ ID NO:71) |
| Primer P2 | 5'-CACTCGAGTGGCTGGATTTCAATTTCTCCAGTAG-3' (SEQ ID NO:72) |

After the first 5' RACE, a single band corresponding to a sequence length of 1,300 nucleotides was obtained. This product was inserted into pT7Blue(R) T-Vector and several clones appropriate in insert size were selected.

Ten 5' RACE clones obtained from two independent PCR reactions were sequenced and the longest clone GEN-078D05TA13 (about 1,300 nucleotides long) was further analyzed.

Both strands of the two overlapping cDNA clones GEN-078D05 and GEN-078D05TA13 were sequenced, whereby it was confirmed that the two clones did not yet cover the whole coding region. Therefore, a further second 5' RACE was carried out. For the second 5' RACE, two primers, P3 and P4, respectively having the sequences shown below in Table 4 were used.

TABLE 4

| Primer | Nucleotide sequence | |
|---|---|---|
| Primer P3 | 5'-GTCGAGCTAGCCATCTCCTCTTCG-3' | (SEQ ID NO:73) |
| Primer P4 | 5'-CATGGGCGACAGGTTCCGAGACC-3' | (SEQ ID NO:74) |

A clone, GEN-078D0508, obtained by the second 5' RACE was 300 nucleotides long. This clone contained an estimable initiation codon and three preceding in-frame termination codons. From these three overlapping clones, it became clear that the whole coding region comprises 2,636 nucleotides. This gene was named brain-specific nucleosome assembly protein (BNAP) gene.

The BNAP gene contains a 1,518-nucleotide open reading frame shown under SEQ ID NO:20. The amino acid encoded thereby comprises 506 amino acid residues, as shown under SEQ-ID NO:19, and the nucleotide sequence of the whole cDNA clone of BNAP is as shown under SEQ ID NO:21.

As shown under SEQ ID NO:21, the 5' noncoding region of said gene was found to be generally rich in GC. Candidate initiation codon sequences were found at nucleotides Nos. 266–268, 287–289 and 329–331. These three sequences all had well conserved sequences in the vicinity of the initiation codons [Kozak, M., J. Biol. Chem., 266, 19867–19870 (1991)].

According to the scanning model, the first ATG (nucleotides Nos. 266–268) of the cDNA clone may be the initiation codon. The termination codon was located at nucleotides Nos. 1784–1786.

The 3' noncoding redion was generally rich in AT and two polyadenylation signals (AATAAA) were located at nucleotides Nos. 2606–2611 and 2610–2615, respectively.

The longest open reading frame comprised 1,518 nucleotides coding for 506 amino acid residues and the calculated molecular weight of the BNAP gene product was 57,600 daltons.

Hydrophilic plots indicated that BNAP is very hydrophilic, like other NAPs.

For recombinant BNAP expression and purification and for eliminating the possibility that the BNAP gene sequence might give three chimera clones in the step of 5' RACE, RT-PCR was performed using a sequence comprising nucleotides Nos. 326–356 as a sense primer and a sequence comprising nucleotides Nos. 1758–1786 as an antisenses primer.

As a result, a single product of about 1,500 bp was obtained and it was thus confirmed that said sequence is not a chimera but a single transcript.

(2) Comparison Between BNAP and NAPs

The amino acid sequence deduced from BNAP showed 46% identity and 65% similarity to hNRP.

The deduced BNAP gene product had motifs characteristic of the NAPs already reported and of BNAP. In general, half of the C terminus was well conserved in humans and yeasts.

The first motif (domain I) is KGIPDYWLI (corresponding to amino acid residues Nos. 309–317 of SEQ ID NO:19). This was observed also in hNRP (KGIPSFWLT SEQ ID NO:75) and in yeast NAP-I (KGIPEFWLT SEQ ID NO:76).

The second motif (domain II) is ASFFNFFSPP (corresponding to amino acid residues Nos. 437–446of SEQ ID NO:19) and this was expressed as DSFFNFFAPP (SEQ ID NO:77) in hNRP and as ESFFNFFSP (SEQ ID NO:78) in yeast NAP-I.

These two motifs were also conserved in the deduced mouse NAP-I and DN38 peptides. Both conserved motifs were each a hydrophilic cluster, and the Cys in position 402 was also found conserved.

Half of the N terminus had no motifs strictly conserved from yeasts to mammalian species, while motifs conserved among mammalian species were found.

For instance, HDLERKYA (corresponding to amino acid residues Nos. 130 to 137 of SEQ ID NO:19) and IINAEYEPTEEECEW (corresponding to amino acid residues Nos. 150–164 of SEQ ID NO:19), which may be associated with mammal-specific functions, were found strictly conserved.

NAPs had acidic stretches, which are believed to be readily capable of binding to histone or other basic proteins. All NAPs had three acidic stretches but the locations thereof were not conserved.

BNAP has no such three acidic stretches but, instead, three repeated sequences (corresponding to amino acid residues Nos. 194–207, 208–221 and 222–235) with a long acidic cluster, inclusive of 41 amino acid residues out of 98 amino acid residues, the consensus sequence being ExxKExPEVKxEEK (SEQ ID NO:79 each x being a nonconserved, mostly hydrophobic, residue).

Furthermore, it was revealed that the BNAP sequence had several BNAP-specific motifs. Thus, an extremely serine-rich doamin (corresponding to amino acid residues Nos. 24–72) with 33 (67%) of 49 amino acid residues being serine residues was found in the N-terminus portion. On the nucleic acid level, they were reflected as incomplete repetitions of AGC.

Following this serine-rich region, there appeared a basic domain (corresponding to amino acid residues Nos. 71–89) comprising 10 basic amino acid residues among 19 residues.

BNAP is supposed to be localized in the nucleus. Two possible signals localized in the nucleus were observed (NLSs). The first signal was found in the basic domain of BNAP and its sequence YRKKR (corresponding to amino acid residues Nos. 75–79 of SEQ ID NO:19) was similar to NLS (GRKKR (SEQ ID NO:81)) of Tat of HIV-1. The second signal was located in the C terminus and its sequence KKYRK (corresponding to amino acid residues Nos. 502–506 of SEQ ID NO:19) was similar to NLS (KKKRK (SEQ ID NO:81),of the large T antigen of SV40. The presence of these two presumable NLSs suggested the localization of BNAP in the nucleus. However the possibility that other basic clusters might act as NLSs could not be excluded.

BNAP has several phosphorylation sites and the activity of BNAP may be controlled through phosphorylation thereof.

(3) Northern Blot Analysis

Northern blot analysis was performed as described in Example 1 (2). Thus, the clone GEN-078D05TA13 (corresponding to nucleotides Nos. 323 to 1558 in the BNAP gene sequence) was amplified by PCR, the PCR product was purified and labeled with [$^{32}$P]-dCTP (random-primed DNA labeling kit, Boehringer Mannheim), and the expression of BNAP mRNA in normal human tissues was examined using an MTN blot with the labeled product as a probe.

As a result of Northern blot analysis, a 3.0 kb transcript of BNAP was detected (8-hour exposure) in the brain among eight human adult tissues tested, namely heart, brain, placenta, lung, liver, skeletal muscle, kidney and pancreas and, after longer exposure (24 hours), a dim band of the same size was detected in the heart.

BNAP was found equally expressed in several sites of brain tested whereas, in other tissues, no signal was detected at all even after 72 hours of exposure. hNRP mRNA was found expressed everywhere in the human tissues tested whereas the expression of BNAP mRNA was tissue-specific.

(4) Radiation Hubrid Mapping

Chromosomal mapping of the BNAP clone was performed by means of radiation hibrid mapping [Cox, D. R., et al., Science, 250, 245–250 (1990)].

Thus, a total human genome radiation hybrid clone (G3RH) panel was purchased from Research Genetics, Inc., AL, USA and PCR was carried out for chromosomal mapping analysis according to the product manual using two primers, A1 and A2, respectively having the nucleotide sequences shown in Table 5.

TABLE 5

| Primer | Nucleotide sequence | |
|---|---|---|
| A1 primer | 5'-CCTAAAAAGTGTCTAAGTGCCAGTT-3' | (SEQ ID NO:82) |
| A2 primer | 5'-TCAGTGAAAGGGAAGGTAGAACAC-3' | (SEQ ID NO:83) |

The results obtained were analyzed utilizing softwares usable on the Internet [Boehnke, M., et al., Am. J. Hum. Genet., 46, 581–586 (1991)].

As a result, the BNAP gene was found strongly linked to the marker DXS990 (LOD=1000, cR8000=–0.00). Since DXS990 is a marker localized on the chromosome Xq21.3-q22, it was established that BNAP is localized to the chromosomal locus Xq21.3-q22 where genes involved in several signs or symptoms of X-chromosome-associated mental retardation are localized.

The nucleosome is not only a fundamental chromosomal structural unit characteristic of eukaryotes but also a gene expression regulating unit. Several results indicate that genes with high transcription activity are sensitive to nuclease treatment, suggesting that the chromosome structure changes with the transcription activity [Elgin, S. C. R., J. Biol. Chem., 263, 19259–19262 (1988)].

NAP-I has been cloned in yeast, mouse and human and is one of the factors capable of promoting nucleosome construction in vivo. In a study performed on their sequences, NAPs containing the epitope of the specific antibody 4A8 were detected in human, mouse, frog, Drosophila and yeast (*Saccharomyces cerevisiae*) [Ishimi, Y., et al., Eur. J. Biochem., 162, 19–24 (1987)].

In these experiments, NAPs, upon SDS-PAGE analysis, electrophoretically migrated to positions corresponding to a molecular weight between 50 and 60 kDa, whereas the recombinant BNAP slowly migrated to a position of about 80 kDa. The epitope of 4A8 was shown to be localized in the second, well-conserved, hydrophobic motif. And, it was simultaneously shown that the triplet FNF is important as a part of the epitope [Fujii-Nakata, T., et al., J. Biol. Chem., 267, 20980–20986 (1992)].

BNAP also contained this consensus motif in domain II. The fact that domain II is markedly hydrophobic and the fact that domain II can be recognized by the immune system suggest that it is probably presented on the BNAP surface and is possibly involved in protein-protein interactions.

Domain I, too, may be involved in protein-protein interactions. Considering that these are conserved generally among NAPs, though to a relatively low extent, it is conceivable that they must be essential for nucleosome construction, although the functional meaning of the conserved domains is still unknown.

The hNRP gene is expressed in thyroid gland, stomach, kidney, intestine, leukemia, lung cancer, mammary cancer and so on [Simon, H. U., et al., Biochem. J., 297, 389–397 (1994)]. Like that, NAPs are expressed everywhere and are thought to be playing an important role in fundamental nucleosome formation.

BNAP may be involved in brain-specific nucleosome formation and an insufficiency thereof may cause neurological diseases or mental retardation as a result of deviated functions of neurons.

BNAP was found strongly linked to a marker on the X-chromosome q21.3-q22 where sequences involved in several symptoms of X-chromosome-associated mental retardation are localized. This center-surrounding region of X-chromosome was rich in genes responsible for a-thalassemia, mental retardation (ATR-X) or some other forms of mental retardation [Gibbons, R. J., et al., Cell, 80, 837–845 (1995)]. Like the analysis of the ATR-X gene which seems to regulate the nucleosome structure, the present inventors suppose that BNAP may be involved in a certain type of X-chromosome-linked mental retardation.

According to this example, the novel BNAP gene is provided and, when said gene is used, it is possible to detect the expression of said gene in various tissues and to produce the BNAP protein by the technology of genetic engineering. Through these, it is possible to study the brain nucleosome formation deeply involved, as mentioned above, in variegated activities essential to cells as well as the functions of cranial nerve cells and to diagnose various neurological diseases or mental retardation in which these are involved and screen out and evaluate drugs for the treatment or prevention of such diseases.

Example 7

Human Skeletal Muscle-specific Ubiquitin-conjugating Enzyme Gene (UBE2G Gene)

The ubiquitin system is a group of enzymes essential for cellular processes and is conserved from yeast to human. Said system is composed of ubiquitin-activating enzymes (UBAs), ubiquitin-conjugating enzymes (UBCs), ubiquitin protein ligases (UBRs) and 26S proteasome particles.

Ubiquitin is transferred from the above-mentioned UBAs to several UBCs, whereby it is activated. UBCs transfer ubiquitins to target proteins with or without the participation of UBRs. These ubiquitin-conjugated target proteins are said to induce a number of cellular responses, such as protein degradation, protein modification, protein translocation, DNA repair, cell cycle control, transcription control, stress responses, etc. and immunological responses [Jentsch, S., et al., Biochim. Biophys. Acta, 1089, 127–139 (1991); Hershko, A. and Ciechanover, A., Annu. Rev. Biochem., 61, 761–807 (1992); Jentsch, S., Annu. Rev. Genet., 26, 179–207 (1992); Ciechanover, A., Cell, 79, 13–21 (1994)].

UBCs are key components of this system and seem to have distinct substrate specificities and modulate different functions. For example, *Saccharomyces cerevisiae* UBC7 is induced by cadmium and involved in resistance to cadmium poisoning [Jungmann, J., et al., Nature, 361, 369–371 (1993)]. Degradation of MAT-α2 is also executed by UBC7 and UBC6 [Chen, P., et al., Cell, 74, 357–369 (1993)].

The novel gene obtained in this example is UBC7-like gene strongly expressed in human skeletal muscle. In the following, cloning and and DNA sequencing thereof are described.

(1) Cloning and DNA Sequencing of Human Skeletal Muscle-specific Ubiquitin-conjugating Enzyme Gene (UBE2G Gene)

Following the same procedure as in Example 1 (1), cDNA clones were arbitrarily selected from a human fetal brain cDNA library and subjected to sequence analysis, and database searches were performed. As a result, a cDNA clone, GEN-423A12, was found to have a significantly high level of homology to the genes coding for ubiquitin-conjugating enzymes (UBCs) in various species.

Since said GEN-423A12 clone was lacking in the 5' side, 5' RACE was performed in the same manner as in Example 2 (2) to obtain an entire coding region.

For said 5' RACE, two primers, P1 and P2, respectively having the nucleotide sequences shown in Table 6 were used.

TABLE 6

| Primer | Nucleotide sequence |
| --- | --- |
| P1 primer | 5'-TAATGAATTTCATTTTAGGAGGTCGG-3' (SEQ ID NO:84) |
| P2 primer | 5'-ATCTTTTGGGAAAGTAAGATGAGCC-3' (SEQ ID NO:85) |

The 5' RACE product was inserted into pT7Blue(R) T-Vector and clones with an insert proper in size were selected.

Four of the 5' RACE clones obtained from two independent PCR reactions contained the same sequence but were different in length.

By sequencing the above clones, the coding sequence and adjacent 5'- and 3'-flanking sequences of the novel gene were determined.

As a result, it was revealed that the novel gene has a total length of 617 nucleotides. This gene was named human skeletal muscle-specific ubiquitin-conjugating enzyme gene (UBE2G gene).

To exclude the conceivable possibility that this sequence was a chimera clone, RT-PCR was performed in the same manner as in Example 6 (1) using the sense primer to amplify said sequence from the human fetal brain cDNA library. As a result, a single PCR product was obtained, whereby it was confirmed that said sequence is not a chimera one.

The UBE2G gene contains an open reading frame of 510 nucleotides, which is shown under SEQ ID NO:23, the amino acid sequence encoded thereby comprises 170 amino acid residues, as shown under SEQ ID NO:22, and the nucleotide sequence of the entire UBE2G cDNA is as shown under SEQ ID NO:24.

As shown under SEQ ID NO:24, the estimable initiation codon was located at nucleotides Nos. 19–21, corresponding to the first ATG triplet of the cDNA clone. Since no preceding in-frame termination codon was found, it was deduced that this clone contains the entire open reading frame on the following grounds.

Thus, (a) the amino acid sequence is highly homologous to *S. cerevisiae* UBC7 and said initiation codon agrees with that of yeast UBC7, supporting said ATG as such. (b) The sequence AGGATGA is similar to the consensus sequence (A/G)CCATGG around the initiation codon [Kozak, M., J. Biol. Chem., 266, 19867–19870 (1991)].

(2) Comparison in Amino Acid Sequence Between UBE2G and UBCs

Comparison in amino acid sequence between UBE2G and UBCs suggested that the active site cystein capable of binding to ubiquitin should be the 90th residue cystein. The peptides encoded by these genes seem to belong to the same family.

(3) Northern Blot Analysis

Northern blot analysis was carried out as described in Example 1 (2). Thus, the entire sequence of UBE2G was amplified by PCR, the PCR product was purified and labeled with [$^{32}$P]-dCTP (random-primed DNA labeling kit, Boehringer. Mannheim) and the expression of UBE2G mRNA in normal human tissues using the labeled product as a probe. The membrane used was an MTN blot.

As a result of the Northern blot analysis, 4.4 kb, 2.4 kb and 1.6 kb transcripts could be detected in all 16 human adult tissues, namely heart, brain, placenta, lung, liver, skeletal muscle, kidney, pancreas, spleen, thyroid gland, urinary bladder, testis, ovary, small intestine, large intestine and peripheral blood leukocye, after 18 hours of exposure. Strong expression of these transcripts was observed in skeletal muscle.

(4) Radiation Hybrid Mapping

Chromosomal mapping of the UBE2G clone was performed by radiation hybrid mapping in the same manner as in Example 6 (4).

The primers C1 and C4 used in PCR for chromosomal mapping analysis respectively correspond to nucleotides Nos. 415–435 and nucleotides Nos. 509–528 in the sequence shown under SEQ ID NO:24 and their nucleotide sequences are as shown below in Table 7.

TABLE 7

| Primer | Nucleotide sequence |
|---|---|
| C1 primer | 5'-GGAGACTCACCTGCTAATGTT-3' (SEQ ID NO:86) |
| C4 primer | 5'-CTCAAAAGCAGTCTCTTGGC-3' (SEQ ID NO:87) |

As a result, the UBE2G gene was found linked to the markers D1S446 (LOD=12.52, cR8000=8.60) and D1S235 (LOD=9.14, cR8000=22.46). These markers are localized to the chromosome bands 1q42.13-q42.3.

UBE2G was expressed strongly in skeletal muscle and very weakly in all other tissues examined. All other UBCs are involved in essential cellular functions, such as cell cycle control, and those UBCs are expressed ubiquitously. However, the expression pattern of UBE2G might suggest a muscle-specific role thereof.

While the three transcripts differing in size were detected, attempts failed to identify which corresponds to the cDNA clone. The primary structure of the UBE2G product showed an extreme homology to yeast UBC7. On the other hand, nematode UBC7 showed strong homology to yeast UBC7. It is involved in degradation of the repressor and further confers resistance to cadmium in yeasts. The similarities among these proteins suggest that they belong to the same family.

It is speculated that UBE2G is involved in degradation of muscle-specific proteins and that a defect in said gene could lead to such diseases as muscular dystrophy. Recently, another proteolytic enzyme, calpain 3, was found to be responsible for limb-girdle muscular dystrophy type 2A [Richard, I., et al., Cell, 81, 27–40 (1995)]. At the present, the chromosomal location of UBE2G suggests no significant relationship with any hereditary muscular disease but it is likely that a relation to the gene will be unearthed by linkage analysis in future.

In accordance with this example, the novel UBE2G gene is provided and the use of said gene enables detection of its expression in various tissues and production of the UBE2G protein by the technology of genetic engineering. Through these, it becomes possible to study the degradation of muscle-specific proteins deeply involved in basic activities variegated and essential to cells, as mentioned above, and the functions of skeletal muscle, to diagnose various muscular diseases in which these are involved and further to screen out and evaluate drugs for the treatment and prevention of such diseases.

Example 8

TMP-2 Gene (1) TMP-2 Gene Cloning and DNA Sequencing

Following the procedure of Example 1 (1), cDNA clones were arbitrarily selected from a human fetal brain cDNA library and subjected to sequence analysis, and database searches were performed. As a result, a clone (GEN-092E10) having a cDNA sequence highly homologous to a transmembrane protein gene (accession No.: U19878) was found out.

Membrane protein genes have so far been cloned in frog (*Xenopus laevis*) and human. These are considered to be a gene for a transmembrane type protein having a follistatin module and an epidermal growth factor (EGF) domain (accession No.: U19878).

The sequence information of the above protein gene indicated that the GEN-092E10 clone was lacking in the 5' region, so that the λgt10 cDNA library (human fetal brain 5'-STRETCH PLUS cDNA; Clontech) was screened using the GEN-092E10 clone as a probe, whereby a cDNA clone containing a further 5' upstream region was isolated.

Both strands of this cDNA clone were sequenced, whereby the sequence covering the entire coding region became clear. This gene was named TMP-2 gene.

The TMP-2 gene was found to contain an open reading frame of 1,122 nucleotides, as shown under SEQ ID NO:26, encoding an amino acid sequence of 374 residues, as shown under SEQ ID NO:25. The nucleotide sequence of the entire TMP-2 cDNA clone comprises 1,721 nucleotides, as shown under SEQ ID NO:27.

As shown under SEQ ID NO:27, the 5' noncoding region was generally rich in GC. Several candidates for the initiation codon were found but, according to the scanning model, the 5th ATG of the cDNA clone (bases Nos. 368–370) was estimated as the initiation codon. The termination codon was located at nucleotides Nos. 1490–1492. The polyadenylation signal (AATAAA) was located at nucleotides Nos. 1703–1708. The calculated molecular weight of the TMP-2 gene product was 41,400 daltons.

As mentioned above, the transmembrane genes have a follistatin module and an EGF domain. These motifs were also found conserved in the novel human gene of the present invention.

The TMP-2 gene of the present invention presumably plays an important role in cell proliferation or intercellular communication, since, on the amino acid level, said gene shows homology, across the EGF domain, to TGF-α (transforming growth factor-α; Derynck, R., et al., Cell, 38, 287–297 (1984)], beta-cellulin [Igarashi, K. and Folkman, J., Science, 259, 1604–1607 (1993)], heparin-binding EGF-like growth factor [Higashiyama, S., et al., Science, 251, 936–939 (1991)] and schwannoma-derived growth factor [Kimura, H., et al., Nature, 348, 257–260 (1990)].

(2) Northern Blot Analysis

Northern blot analysis was carried out as described in Example 1 (2). Thus, the clone GEN-092E10 was amplified by PCR, the PCR product was purified and labeled with [$^{32}$P]-dCTP (random-primed DNA labeling kit, Boehringer Mannheim), and the expression of TMP-2 mRNA in normal human tissues was examined using an MTN blot with the labeled product as a probe.

As a result, high levels of expression were detected in brain and prostate gland. Said TMP-2 gene mRNA was about 2 kb in size.

According to the present invention, the novel human TMP-2 gene is provided and the use of said gene makes it possible to detect the expression of said gene in various tissues or produce the human TMP-2 protein by the technology of genetic engineering and, through these, it becomes possible to study brain tumor and prostatic cancer, which are closely associated with cell proliferation or intercellular communication, as mentioned above, to diagnose these diseases and to screen out and evaluate drugs for the treatment and prevention of such diseases.

Example 9

Human NPIK Gene (1) Human NPIK Gene Cloning and DNA Sequencing

Following the procedures of Example 1 and Example 2, cDNA clones were arbitrarily selected from a human fetal brain cDNA library and subjected to sequence analysis, and database searches were performed. As a result, two cDNA clones highly homologous to the gene coding for an amino acid sequence conserved in phosphatidylinositol 3 and 4 kinases [Kunz, J., et al., Cell, 73, 585–596 (1993)] were obtained. These were named GEN-428B12c1 and GEN-428B12c2 and the entire sequences of these were determined as in the foregoing examples.

As a result, the GEN-428B12c1 cDNA clone and the GEN-428B12c2 clone were found to have coding sequences differing by 12 amino acid residues at the 5' terminus, the GEN-428B12c1 cDNA clone being longer by 12 amino acid residues.

The GEN-428B12c1 cDNA sequence of the human NPIK gene contained an open reading frame of 2,487 nucleotides, as shown under SEQ ID NO:32, encoding an amino acid sequence comprising 829 amino acid residues, as shown under SEQ ID NO:31. The nucleotide sequence of the full-length cDNA clone comprised 3,324 nucleotides as shown under SEQ ID NO:33.

The estimated initiation codon was located, as shown under SEQ ID NO:33, at nucleotides Nos. 115–117 corresponding to the second ATG triplet of the cDNA clone. The termination codon was located at nucleotides Nos. 2602–2604 and the polyadenylation signal (AATAAA) at Nos. 3305–3310.

On the other hand, the GEN-428B12c2 cDNA sequence of the human NPIK gene contained an open reading frame of 2,451 nucleotides, as shown under SEQ ID NO:29. The amino acid sequence encoded thereby comprised 817 amino acid residues, as shown under SEQ ID NO:28. The nucleotide sequence of the full-length cDNA clone comprised 3,602 nucleotides, as shown under SEQ ID NO:30.

The estimated initiation codon was located, as shown under SEQ ID NO:30, at nucleotides Nos. 429–431 corresponding to the 7th ATG triplet of the cDNA clone. The termination codon was located at nucleotides Nos. 2880–2882 and the polyadenylation signal (AATAAA) at Nos. 3583–3588.

(2) Northern Blot Analysis

Northern blot analysis was carried out as described in Example 1 (2). Thus, the entire sequence of human NPIK was amplified by PCR, the PCR product was purified and labeled with [$^{32}$P]-dCTP (random-primed DNA labeling kit, Boehringer Mannheim), and normal human tissues were examined for expression of the human NPIK mRNA using the MTN blot membrane with the labeled product as a probe.

As a result, the expression of the human NPIK gene was observed in 16 various human adult tissues examined and an about 3.8 kb transcript and an about 5 kb one could be detected.

Using primer A having the nucleotide sequence shown below in Table 8 and containing the initiation codon of the GEN-428B12c2 cDNA and primer B shown in table 8 and containing the termination codon, PCR was performed with Human Fetal Brain Marathon-Ready cDNA (Clontech) as a template, and the nucleotide sequence of the PCR product was determined.

TABLE 8

| Primer | Nucleotide sequence |
|---|---|
| Primer A | 5'-ATGGGAGATACAGTAGTGGAGC-3' (SEQ ID NO:88) |
| Primer B | 5'-TCACATGATGCCGTTGGTGAG-3' (SEQ ID NO:89) |

As a result, it was found that the human NPIK mRNA expressed included one lacking in nucleotides Nos. 1060–1104 of the GEN-428B12c1 cDNA sequence (SEQ ID NO:33) (amino acids Nos. 316–330 of the amino acid sequence under SEQ ID NO:31) and one lacking in nucleotides Nos. 1897–1911 of the GEN-428B12c1 cDNA sequence (SEQ ID NO:33) (amino acids Nos. 595–599 of the amino acid sequence under SEQ ID NO:31).

It was further revealed that polymorphism existed in this gene (428B12c1.fasta), as shown below in Table 9, in the region of bases Nos. 1941–1966 of the GEN-428B12c1 cDNA sequence shown under SEQ ID NO:33, whereby a mutant protein was encoded which resulted from the mutation of IQDSCEITT (amino acid residues Nos. 610–618 in the amino acid sequence (SEQ ID NO:31) encoded by GEN-428B12cl) into YKILVISA.

TABLE 9

```
                                               1930       1940       1950     1959
                                               TGGATCAAGCCAATACAAGATTCTTGTGAA
                                               ||||||||||| ||||||||||||||||
            TCCATTTGGAACAGGAGCGAGTGCCCCTTTAGGATCAAGCC-ATACAAGATTCTTGTG--
            1900       1910       1920       1930       1940       1950

1960       1970       1980
```

TABLE 9-continued

```
ATTACGACTGATAGTGGCATG (SEQ ID NO:90)
||| || ||||||||||||||
ATTTCGGCTGATAGTGGCATGATTGAACCAGTGGTCAATGCTGTGTCCATCCATCAGGTG (SEQ ID
NO:91)
   1960      1970      1980      1990      2000      2010
```

(3) Chromosomal Mapping of Human NPIK Gene by FISH

Chromosomal mapping of the human NPIK gene was carried out by FISH as described in Example 1 (3).

As a result, it was found that the locus of the human NPIK gene is in the chromosomal position 1q21.1-q21.3.

The human NPIK gene, a novel human gene, of the present invention included two cDNAs differing in the 5' region and capable of encoding 829 and 817 amino acid residues, as mentioned above. In view of this and further in view of the findings that the mRNA corresponding to this gene includes two deletable sites and there occurs polymorphism in a specific region corresponding to amino acid residues Nos. 610–618 of the GEN-428B12c1 amino acid sequence (SEQ ID NO:31), whereby a mutant protein is encoded, it is conceivable that human NPIK includes species resulting from a certain number of combinations, namely human NPIK, deletion-containing human NPIK, human NPIK mutant and/or deletion-containing human NPIK mutant.

Recently, several proteins belonging to the family including the above-mentioned PI3 and 4 kinases have protein kinase activity [Dhand, R., et al., EMBO J., 13, 522–533 (1994); Stack, J. H. and Emr, S. D., J. Biol. Chem., 269, 31552–31562 (1994); Hartley, K. O., et al., Cell, 82, 848–856 (1995)].

It was also revealed that a protein belonging to this family is involved in DNA repair [Hartley, K. O., et al., Cell, 82, 849–856 (1995)] and is a causative gene of ataxia [Savitsky, K., et al., Science, 268, 1749–1753 (1995)].

It can be anticipated that the human NPIK gene-encoded protein highly homologous to the family of these PI kinases is a novel enzyme phosphorylating lipids or proteins.

According to this example, the novel human NPIK gene is provided. The use of said gene makes it possible to detect the expression of said gene in various tissues and manufacture the human NPIK protein by the technology of genetic engineering and, through these, it becomes possible to study lipid- or protein-phosphrylating enzymes such as mentioned above, study DNA repairing, study or diagnose diseases in which these are involved, for example cancer, and screen out and evaluate drugs for the treatment or prevention thereof.

(4) Construction of an Expression Vector for Fusion Protein

To subclone the coding region for a human NPIK gene (GEN-428B12c2), first of all, two primers, C1 and C2, having the sequences shown below in Table 10 were formed based on the information on the DNA sequences obtained above in (1).

Both of the primers C1 and C2 have a BglII site, and primer C2 is an antisense primer.

Using these two primers, cDNA derived from human fetal brain mRNA was amplified by PCR to provide a product having a length of about 2500 bases. The amplified cDNA was precipitated from ethanol and inserted into pT7BlueT-Vector (product of Novagen) and subcloning was completed. The entire sequence was determined in the same manner as above in Examples. As a result, it was revealed that this gene had polymorphism shown above in Table 9.

The above cDNA was cleaved by BglII and subjected to agarose gel electrophoresis. The cDNA was then excised from agarose gel and collected using GENECLEAN II KIT (product of Bio 101). The cDNA was inserted into pBlueBacHis2B-Vector (product of Invitrogen) at the BqlII cleavage site and subcloning was completed.

The fusion vector thus obtained had a BglII cleavage site and was an expression vector for a fusion protein of the contemplated gene product (about 91 kd) and 38 amino acids derived from pBlueBacHis2B-Vector and containing a polyhistidine region and an epitope recognizing Anti-Xpress™ antibody (product of Invitrogen).

(5) Transfection Into Insect Cell Sf-9

The human NPIK gene was expressed according to the Baculovirus expression system. Baculovirus is a cyclic double-stranded insect-pathogenic virus and can produce large amounts of inclusion bodies named polyhedrins in the cells of insects. Using Bac-N-Blue™ Transfection Kit utilizing this characteristic of Baculovirus and developed by Invitrogen, the Baculovirus expression was carried out.

Stated more specifically, 4 $\mu$g of pBlueBacHis2B containing the region of the human NPIK gene and 1 $\mu$g of Bac-N-Blue™ DNA (product of Invitrogen) were co-transfected into Sf-9 cells in the presence of Insectin™ liposomes (product of Invitrogen).

Prior to co-transfection, LacZ gene was incorporated into Bac-N-Blue™ DNA, so that LacZ would be expressed only when homologous recombination took place between the Bac-N-Blue™ DNA and pBlueBacHis2B. Thus when the co-transfected Sf-9 cells were incubated on agar medium, the plaques of the virus expressing the contemplated gene were easily detected as blue plaques.

The blue plaques were excised from each agar and suspended in 400 $\mu$l of medium to disperse the virus thereon. The suspension was subjected to centrifugation to give a supernatant containing the virus. Sf-9 cells were infected with the virus again to increase the titre and to obtain a large amount of infective virus solution.

TABLE 10

| Primer | Nucleotide sequence |
|---|---|
| Primer C1 | 5'-CTCAGATCTATGGGAGATACAGTAGTGGAGC-3' (SEQ ID NO:92) |
| Primer C2 | 5'-TCGAGATCTTCACATGATGCCGTTGGTGAG-3' (SEQ ID NO:93) |

(6) Preparation of Human NPIK

The expression of the contemplated human NPIK gene was confirmed three days after infection with the virus as follows.

Sf-9 cells were collected and washed with PBS. The cells were boiled with a SDS-PAGE loading buffer for 5 minutes and SDS-PAGE was performed. According to the western blot technique using Anti-Xpress as an antibody, the contemplated protein was detected at the position of its presumed molecular weight. By contrast, in the case of control cells uninfected with the virus, no band corresponding to human NPIK was observed in the same test.

Stated more specifically, three days after the infection of 15 flasks (175-cm$^2$, FALCON) of semi-confluent Sf-9 cells, the cells were harvested and washed with PBS, followed by resuspension in a buffer (20 mM Tris/HCl (pH 7.5), 1 mM EDTA and 1 mM DTT). The suspended cells were lysed by 4 time-sonications for 30 seconds at 4° C. with 30 seconds intervals. The sonicated cells were subjected to centrifugation and the supernatant was collected. The protein in the supernatant was immunoprecipitated using an Anti-Xpress antibody and obtained as a slurry of protein A-Sepharose beads. The slurry was boiled with a SDS-PAGE loading buffer for 5 minutes. SDS-PAGE was performed for identification and quantification of NPIK. The slurry itself was subjected to the following assaying.

(7) Confirmation of PI4 Kinase Activity

NPIK was expected to have the activity of incorporation phosphoric acid at the 4-position of the inositol ring of phosphatidylinositol (PI), namely, PI4 Kinase activity.

PI4 Kinase activity of NPIK was assayed according to the method of Takenawa, et al. (Yamakawa, A. and Takenawa, T., J. Biol. Chem., 263, 17555–17560 (1988)) as shown below.

First prepared was a mixture of 10 μl of a NPIK slurry (20 mM Tris/HCl (pH 7.5), 1 mM EDTA, 1 mM DTT and 50% protein A beads), 10 μl of a PI solution (prepared by drying 5 mg of a PI-containing commercial chloroform solution in a stream of nitrogen onto a glass tube wall, adding 1 ml of 20 mM Tris/HCl (pH 7.5) buffer and forming micelles by sonication), 10 μl of an applied buffer (210 mM Tris/HCl (pH 7.5), 5 mM EGTA and 100 mM $MgCl_2$) and 10 μl of distilled water. Thereto was added 10 μl of an ATP solution (5 μl of 500 μM ATP, 4.9 μl of distilled water and 0.1 μl of γ-$^{32}$P ATP (6000 Ci/mmol, product of NEN Co., Ltd.)). The reaction was started at 30° C. and continued for 2, 5, 10 and 20 minutes. The time 10 minutes was set as incubation time because a straight-line increase was observed around 10 minutes in incorporation of phosphoric acid into PI in the assaying process described below.

After completion of the reaction, PI was fractionated by the solvent extraction method and finally re-suspended in chloroform. The suspension was developed by thin layer chromatography (TLC) and the radioactivity of the reaction product at the PI4P-position was assayed using an analyzer (trade name: Bio-Image; product of Fuji Photo Film Co., Ltd.).

FIG. 1 shows the results. FIG. 1 is an analytical diagram of the results of assaying the radioactivity based on TLC as mentioned above. The right lane (2) is the fraction of Sf-9 cell cytoplasm infected with the NPIK-containing virus, whereas the left lane (1) is the fraction of uninfected Sf-9 cell cytoplasm.

Also, predetermined amounts of Triton X-100 and adenosine were added to the above reaction system to check how such addition would affect the PI4 Kinase activity. The PI4 Kinase activity was assayed in the same manner as above.

Figure 2:
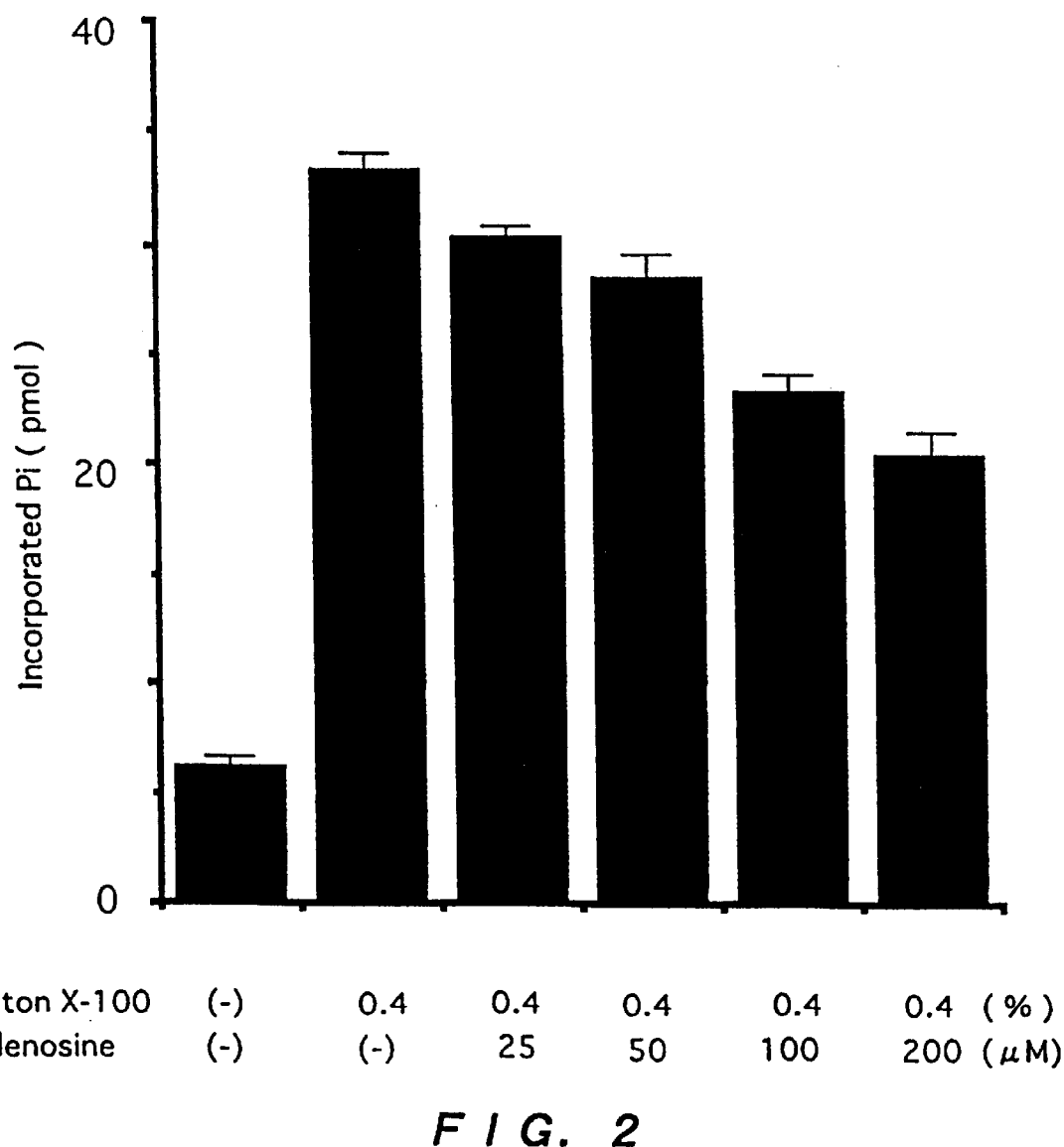
FIG. 2 shows the effect of Triton X-100 and adenosine on NPIK activity.

FIG. 2 shows the results. The results confirmed that NPIK had a typical PI4 Kinaze activity accelerated by Triton X-100 and inhibited by adenosine.

Example 10

Nel-related Protein Type 1 (NRP1) Gene and Nel-related Protein Type 2 (NRP2) Gene (1) Cloning and DNA Sequencing of NRP1 Gene and NRP2 Gene EGF-like repeats have been found in many membrane proteins and in proteins related to growth regulation and differentiation. This motif seems to be involved in protein-protein interactions.

Recently, a gene encoding nel, a novel peptide containing five EGF-like repeats, was cloned from a chick embryonic cDNA library [Matsuhashi, S., et al., Dev. Dynamics, 203, 212–222 (1995)]. This product is considered to be a transmembrane molecule with its EGF-like repeats in the extracellular domain. A 4.5 kb transcript (nel mRNA) is expressed in various tissues at the embryonic stage and exclusively in brain and retina after hatching.

Following the procedure of Example 1 (1), cDNA clones were randomly selected from a human fetal brain cDNA library and subjected to sequence analysis, followed by database searching. As a result, two cDNA clones with significantly high homology to the above-mentioned nel were found and named GEN-073E07 and GEN-093E05, respectively.

Since both clones were lacking in the 5' portion, 5' RACE was performed in the same manner as in Example 2 (2) to obtain the entire coding regions.

As for the primers for 5' RACE, primers having an arbitrary sequence obtained from the cDNA sequences of the above clones were synthesized while the anchor primer attached to a commercial kit was used as such.

5' RACE clones obtained from the PCR were sequenced and the sequences seemingly covering the entire coding regions of both genes were obtained. These genes were respectively named nel-related protein type 1 (NRP1) gene and nel-related protein type 2 (NRP2) gene.

The NRP1 gene contains an open reading frame of 2,430 nucleotides, as shown under SEQ ID NO:35, the amino acid sequence deduced therefrom comprises 810 amino acid residues, as shown under SEQ ID NO:34, and the nucleotide sequence of the entire cDNA clone of said NRP1 gene comprises 2,977 nucleotides, as shown under SEQ ID NO:36.

On the other hand, the NRP2 gene contains an open reading frame of 2,448 nucleotides, as shown under SEQ ID NO:38, the amino acid sequence deduced therefrom comprises 816 amino acid residues, as shown under SEQ ID NO:37, and the nucleotide sequence of the entire cDNA clone of said NRP2 gene comprises 3,198 nucleotides, as shown under SEQ ID NO:39.

Furthermore, the coding regions were amplified by RT-PCR to exclude the possibility that either of the sequences obtained was a chimeric cDNA.

The deduced NRP1 and NRP2 gene products both showed highly hydrophobic N termini capable of functioning as signal peptides for membrane insertion. As compared with chick embryonic nel, they both appeared to have no hydrophobic transmembrane domain. Comparison among NRP1, NRP2 and nel with respect to the deduced peptide sequences revealed that NRP2 has 80% homology on the amino acid level and is more closely related to nel than NRP1 having 50% homology. The cysteine residues in cysteine-rich domains and EGF-like repeats were found completely conserved.

The most remarkable difference between the NRPs and the chick protein was that the human homologs lack the putative transmembrane domain of nel. However, even in this lacking region, the nucleotide sequences of NRPs were very similar to that of nel. Furthermore, the two NRPs each possessed six EGF-like repeats, whereas nel has only five.

Other unique motifs of nel as reported by Matsuhashi et al. [Matsuhashi, S., et al., Dev. Dynamics, 203, 212–222 (1995)] were also found in the NRPs at equivalent positions. Since as mentioned above, it was shown that the two deduced NRP peptides are not transmembrane proteins, the NRPs might be secretory proteins or proteins anchored to membranes as a result of posttranslational modification.

The present inventors speculate that NRPs might function as ligands by stimulating other molecules such as EGF receptors. The present inventors further found that an extra EGF-like repeat could be encoded in nel upon frame shifting of the membrane domain region of nel.

When paralleled and compared with NRP2 and nel, the frame-shifted amino acid sequence showed similarities over the whole range of NRP2 and of nel, suggesting that NRP2 might be a human counterpart of- nel. In contrast, NRP1 is considered to be not a human counterpart of nel but a homologous gene.

(2) Northern Blot Analysis

Northern blot analysis was carried out as described in Example 1 (2). Thus, the entire sequences of both clones cDNAs were amplified by PCR, the PCR products were purified and labeled with [$^{32}$P]-dCTP (random-primed DNA labeling kit, Boehringer Mannheim) and human normal tissues were examined for NRP mRNA expression using an MTN blot with the labeled products as two probes.

Sixteen adult tissues and four human fetal tissues were examined for the expression pattern of two NRPs.

As a result of the Northern blot analysis, it was found that a 3.5 kb transcript of NRP1 was weakly expressed in fetal and adult brain and kidney. A 3.6 kb transcript of NRP2 was strongly expressed in adult and fetal brain alone, with weak expression thereof in fetal kidney as well.

This suggests that NRPs might play a brain-specific role, for example as signal molecules for growth regulation. In addition, these genes might have a particular function in kidney.

(3) Chromosomal Mapping of NRP1 Gene and NRP2 Gene by FISH

Chromosomal mapping of the NRP1 gene and NRP2 gene was performed by FISH as described in Example 1 (3).

As a result, it was revealed that the chromosomal locus of the NRP1 gene is localized to 11p15.1-p15.2 and the chromosomal locus of the NRP2 gene to 12q13.11-q13.12.

According to the present invention, the novel human NRP1 gene and NRP2 gene are provided and the use of said genes makes it possible to detect the expression of said genes in various tissues and produce the human NRP1 and NRP2 proteins by the technology of genetic engineering. They can further be used in the study of the brain neurotransmission system, diagnosis of various diseases related to neurotransmission in the brain, and the screening and evaluation of drugs for the treatment and prevention of such diseases. Furthermore, the possibility is suggested that these EGF domain-containing NRPs act as growth factors in brain, hence they may be useful in the diagnosis and treatment of various kinds of intracerebral tumor and effective in nerve regeneration in cases of degenerative nervous diseases.

Example 11

GSPT1-related Protein (GSPT1-TK) Gene (1) GSPT1-TK Gene Cloning and DNA Sequencing The human GSPT1 gene is one of the human homologous genes of the yeast GST1 gene that encodes the GTP-binding protein essential for the G1 to S phase transition in the cell cycle. The yeast GST1 gene, first identified as a protein capable of complementing a temperature-sensitive gst1 (G1-to-S transition) mutant of *Saccharomyces cerevisiae*, was isolated from a yeast genomic library [Kikuchi, Y., Shimatake, H. and Kikuchi, A., EMBO J., 7, 1175–1182 (1988)] and encoded a protein with a target site of cAMP-dependent protein kinases and a GTPase domain.

The human GSPT1 gene was isolated from a KB cell cDNA library by hybridization using the yeast GST1 gene as a probe [Hoshino, S., Miyazawa, H., Enomoto, T., Hanaoka, F., Kikuchi, Y., Kikuchi, A. and Ui, M., EMBO J., 8, 3807–3814 (1989)]. The deduced protein of said GSPT1 gene, like yeast GST1, has a GTP-binding domain and a GTPase activity center, and plays an important role in cell proliferation.

Furthermore, a breakpoint for chromosome rearrangement has been observed in the GSPT1 gene located in the chromosomal locus 16p13.3 in patients with acute nonlymphocytic leukemia (ANLL) [Ozawa, K., Murakami, Y., Eki, T., Yokoyama, K. Soeda, E., Hoshino, S. Ui, M. and Hanaoka, F., Somatic Cell and Molecular Genet., 18, 189–194 (1992)].

cDNA clones were randomly selected from a human fetal brain cDNA library and subjected to sequence analysis as described in Example 1 (1) and database searching was performed and, as a result, a clone having a 0.3 kb cDNA sequence highly homologous to the above-mentioned GSPT1 gene was found and named GEN-077A09. The GEN-077A09 clone seemed to be lacking in the 5' region, so that 5' RACE was carried out in the same manner as in Example 2 (2) to obtain the entire coding region.

The primers used for the 5' RACE were P1 and P2 primers respectively having the nucleotide sequences shown in Table 11 as designed based on the known cDNA sequence of the above-mentioned cDNA, and the anchor primer used was the one attached to the commercial kit. Thirtyfive cycles of PCR were performed under the following conditions: 94° C. for 45 seconds, 58° C. for 45 seconds and 72° C. for 2 minutes. Finally, elongation reaction was carried out at 72° C. for 7 minutes.

TABLE 11

| Primer | Nucleotide sequence |
| --- | --- |
| P1 primer | 5'-GATTTGTGCTCAATAATCACTATCTGAA-3' (SEQ ID NO:94) |
| P2 primer | 5'-GGTTACTAGGATCACAAAGTATGAATTCTGGAA-3' (SEQ ID NO:95) |

Several of the 5' RACE clones obtained from the above PCR were sequenced and the base sequence of that cDNA clone showing overlapping between the 5' RACE clones and the GEN-077A09 clone was determined to thereby reveal the sequence regarded as covering the entire coding region. This was named GSPT1-related protein "GSPT1-TK gene".

The GSPT1-TK gene was found to contain an open reading frame of 1,497 nucleotides, as shown under SEQ ID NO:41. The amino acid sequence deduced therefrom contained 499 amino acid residues, as shown under SEQ ID NO:40.

The nucleotide sequence of the whole cDNA clone of the GSPTI-TK gene was found to comprise 2,057 nucleotides, as shown under SEQ ID NO:42, and the molecular weight was calculated at 55,740 daltons.

The first methionine code (ATG) in the open reading frame had no in-frame termination codon but this ATG was surrounded by a sequence similar to the Kozak consensus sequence for translational initiation. Therefore, it was concluded that this ATG triplet occurring in positions 144–146 of the relevant sequence is the initiation codon.

Furthermore, a polyadenylation signal, AATAAA, was observed 13 nucleotides upstream from the polyadenylation site.

Human GSPT1-TK contains a glutamic acid rich region near the N terminus, and 18 of 20 glutamic acid residues occurring in this region of human GSPT1-TK are conserved and align perfectly with those of the human GSPT1 protein. Several regions (G1, G2, G3, G4 and G5) of GTP-binding proteins that are responsible for guanine nucleotide binding and hydrolysis were found conserved in the GSPT1-TK protein just as in the human GSPT1 protein.

Thus, the DNA sequence of human GSPT1-TK was found 89.4% identical, and the amino acid sequence deduced therefrom 92.4% identical, with the corresponding sequence of human GSPT1 which supposedly plays an important role in the G1 to S phase transition in the cell cycle. Said amino acid sequence showed 50.8% identity with that of yeast GST1.

(2) Northern Blot Analysis

Northern blot analysis was carried out as described in Example 1 (2). Thus, the GEN-077A09 cDNA clone was amplified by PCR, the PCR product was purified and labeled with [$^{32}$P]-dCTP (random-primed DNA labeling kit, Boehringer Mannheim), and normal human tissues were examined for the expression of GSPT1-TK mRNA therein using an MTN blot with the labeled product as a probe.

As a result of the Northern blot analysis, a 2.7 kb major transcript was detected in various tissues. The level of human GSPT1-TK expression seemed highest in brain and in testis.

(3) Chromosome Mapping of GSPT1-TK Gene by FISH

Chromosome mapping of the GSPT1-TK gene was performed by FISH as described in Example 1 (3).

As a result, it was found that the GSPT1-TK gene is localized at the chromosomal locus 19p13.3. In this chromosomal localization site, reciprocal location has been observed very frequently in cases of acute lymphocytic leukemia (ALL) and acute myeloid leukemia (AML). In addition, it is reported that acute non-lymphocytic leukemia (ANLL) is associated with rearrangements involving the human GSPT1 region [Ozawa, K., Murakami, Y., Eki, T., Yokoyama, K., Soeda, E., Hoshino, S., Ui, M. and Hanaoka, F., Somatic Cell and Molecular Genet., 18, 189–194 (1992)].

In view of the above, it is suggested that this gene is the best candidate gene associated with ALL and AML.

In accordance with the present invention, the novel human GSPT1-TK gene is provided and the use of said gene makes it possible to detect the expression of said gene in various tissues and produce the human GSPT1-TK protein by the technology of genetic engineering. These can be used in the studies of cell proliferation, as mentioned above, and further make it possible to diagnose various diseases associated with the chromosomal locus of this gene, for example acute myelocytic leukemia. This is because translocation of this gene may result in decomposition of the GSPT1-TK gene and further some or other fused protein expressed upon said translocation may cause such diseases.

Furthermore, it is expected that diagnosis and treatment of said diseases can be made possible by producing antibodies to such fused protein, revealing the intracellular localization of said protein and examining its expression specific to said diseases. Therefore, it is also expected that the use of the gene of the present invention makes it possible to screen out and evaluate drugs for the treatment and prevention of said diseases.

What is claimed is:

1. A method for detecting the expression of human skeletal muscle-specific ubiquitin-conjugating enzyme in biological tissue, comprising the steps of:
   a) providing a biological tissue sample to be tested;
   b) extracting RNA from said sample;
   c) contacting said RNA with a DNA probe, said probe comprising a polynucleotide sequence comprising all or part of the sequence of SEQ ID NO:24 which is complementary to a human skeletal muscle-specific ubiquitin-conjugating enzyme messenger RNA; and
   d) determining the presence of hybrid molecules comprising said probe as an indication of the expression of human skeletal muscle-specific ubiquitin-conjugating enzyme.

2. A primer comprising a nucleotide sequence of at least a 20-nucleotide subsequence of SEQ ID NO:24.

* * * * *